(12) United States Patent
Connor

(10) Patent No.: US 12,721,524 B2
(45) Date of Patent: Sep. 1, 2026

(54) BIOMETRIC WEARABLE DEVICE (E.G. FINGER RING OR SMART WATCH) WITH OPTICAL SENSORS AND BODY-FACING PROTRUSIONS

(71) Applicant: Robert A. Connor, Wyoming, MN (US)

(72) Inventor: Robert A. Connor, Wyoming, MN (US)

(73) Assignee: Medibotics LLC, Ham Lake, MN (US)

( * ) Notice: Subject to any disclaimer, the term of this patent is extended or adjusted under 35 U.S.C. 154(b) by 0 days.

(21) Appl. No.: 18/977,825

(22) Filed: Dec. 11, 2024

(65) Prior Publication Data

US 2025/0134381 A1 May 1, 2025

Related U.S. Application Data

(63) Continuation-in-part of application No. 18/929,026, filed on Oct. 28, 2024, which is a continuation-in-part of application No. 18/885,728, filed on Sep. 15, 2024, application No. 18/977,825 is a continuation-in-part of application No. 18/885,728, filed on Sep. 15, 2024, and a continuation-in-part of application No. 18/775,128, filed on Jul. 17, 2024, now Pat. No. 12,405,211, said application No. 18/929,026 is a continuation-in-part of application No. 18/775,128, filed on Jul. 17, 2024, now Pat. No. 12,405,211, said application No. 18/885,728 is a continuation-in-part of application No. 18/775,128, filed on Jul. 17, 2024, now Pat. No. 12,405,211, which is a continuation-in-part of application No. 18/617,950, filed on Mar. 27, 2024, application No. 18/977,825 is a continuation-in-part of application No. 18/617,950, filed on Mar. 27, 2024, said application No. 18/885,728 is a continuation-in-part of application No. 18/617,950, filed on Mar. 27, 2024, and a (Continued)

(51) Int. Cl.
*A61B 5/00* (2006.01)

(52) U.S. Cl.
CPC .......... *A61B 5/0075* (2013.01); *A61B 5/6826* (2013.01); *A61B 2562/043* (2013.01)

(58) Field of Classification Search
CPC ................ A61B 5/0075; A61B 5/6826; A61B 2562/043; A61B 2562/146
See application file for complete search history.

(56) References Cited

U.S. PATENT DOCUMENTS 7,350,377 B2 * 4/2008 Kaplan .................... A44C 9/00 63/15
8,725,226 B2 5/2014 Isaacson (Continued)

FOREIGN PATENT DOCUMENTS

CN 210644034 U * 6/2020

*Primary Examiner* — Jacqueline Cheng
*Assistant Examiner* — Tho Q Tran

(57) ABSTRACT

A biometric wearable device (e.g. finger ring or smart watch) has optical sensors to measure body oxygenation level, hydration level, glucose level, heart rate, heart rate variability, and/or blood pressure. Light from light emitters is transmitted through body tissue and changes in the light are analyzed. In an example, the device can include body-facing protrusions where the light emitters and/or the light receivers are located.

2 Claims, 3 Drawing Sheets

Related U.S. Application Data continuation-in-part of application No. 18/121,841, filed on Mar. 15, 2023, now abandoned, said application No. 18/775,128 is a continuation-in-part of application No. 18/121,841, filed on Mar. 15, 2023, now abandoned, said application No. 18/617,950 is a continuation-in-part of application No. 18/121,841, filed on Mar. 15, 2023, now abandoned, said application No. 18/929,026 is a continuation-in-part of application No. 18/121,841, filed on Mar. 15, 2023, now abandoned, application No. 18/977,825 is a continuation-in-part of application No. 18/121,841, filed on Mar. 15, 2023, now abandoned, which is a continuation-in-part of application No. 17/903,746, filed on Sep. 6, 2022, now abandoned, and a continuation-in-part of application No. 17/239,960, filed on Apr. 26, 2021, now abandoned, said application No. 17/903,746 is a continuation-in-part of application No. 17/239,960, filed on Apr. 26, 2021, now abandoned, and a continuation-in-part of application No. 16/737,052, filed on Jan. 8, 2020, now Pat. No. 11,754,542, said application No. 17/239,960 is a continuation-in-part of application No. 16/737,052, filed on Jan. 8, 2020, now Pat. No. 11,754,542, said application No. 18/121,841 is a continuation-in-part of application No. 16/737,052, filed on Jan. 8, 2020, now Pat. No. 11,754,542, which is a continuation-in-part of application No. 16/568,580, filed on Sep. 12, 2019, now Pat. No. 11,478,158, said application No. 17/903,746 is a continuation-in-part of application No. 16/568,580, filed on Sep. 12, 2019, now Pat. No. 11,478,158, said application No. 16/737,052 is a continuation-in-part of application No. 15/963,061, filed on Apr. 25, 2018, now Pat. No. 10,772,559, said application No. 16/568,580 is a continuation-in-part of application No. 15/963,061, filed on Apr. 25, 2018, now Pat. No. 10,772,559, and a continuation-in-part of application No. 15/944,746, filed on Apr. 3, 2018, now abandoned, said application No. 16/737,052 is a continuation-in-part of application No. 15/725,330, filed on Oct. 5, 2017, now Pat. No. 10,607,507, said application No. 16/568,580 is a continuation-in-part of application No. 15/725,330, filed on Oct. 5, 2017, now Pat. No. 10,607,507, said application No. 16/737,052 is a continuation-in-part of application No. 15/431,769, filed on Feb. 14, 2017, now abandoned, said application No. 15/725,330 is a continuation-in-part of application No. 15/431,769, filed on Feb. 14, 2017, now abandoned, said application No. 16/568,580 is a continuation-in-part of application No. 15/431,769, filed on Feb. 14, 2017, now abandoned, and a continuation-in-part of application No. 15/418,620, filed on Jan. 27, 2017, now abandoned, said application No. 15/431,769 is a continuation-in-part of application No. 15/294,746, filed on Oct. 16, 2016, now Pat. No. 10,627,861, said application No. 16/737,052 is a continuation-in-part of application No. 15/294,746, filed on Oct. 16, 2016, now Pat. No. 10,627,861, said application No. 15/431,769 is a continuation-in-part of application No. 15/206,215, filed on Jul. 8, 2016, now abandoned, said application No. 15/963,061 is a continuation-in-part of application No. 14/992,073, filed on Jan. 11, 2016, now abandoned, said application No. 15/431,769 is a continuation-in-part of application No. 14/992,073, filed on Jan. 11, 2016, now abandoned, said application No. 15/206,215 is a continuation-in-part of application No. 14/951,475, filed on Nov. 24, 2015, now Pat. No. 10,314,492, said application No. 15/418,620 is a continuation-in-part of application No. 14/951,475, filed on Nov. 24, 2015, now Pat. No. 10,314,492, said application No. 15/294,746 is a continuation-in-part of application No. 14/951,475, filed on Nov. 24, 2015, now Pat. No. 10,314,492, said application No. 15/725,330 is a continuation-in-part of application No. 14/951,475, filed on Nov. 24, 2015, now Pat. No. 10,314,492, said application No. 15/206,215 is a continuation-in-part of application No. 14/948,308, filed on Nov. 21, 2015, now abandoned, said application No. 14/992,073 is a continuation-in-part of application No. 14/562,719, filed on Dec. 7, 2014, now Pat. No. 10,130,277, said application No. 14/948,308 is a continuation-in-part of application No. 14/550,953, filed on Nov. 22, 2014, now abandoned, said application No. 15/963,061 is a continuation-in-part of application No. 14/550,953, filed on Nov. 22, 2014, now abandoned, said application No. 14/948,308 is a continuation-in-part of application No. 14/449,387, filed on Aug. 1, 2014, now abandoned, said application No. 15/431,769 is a continuation-in-part of application No. 14/330,649, filed on Jul. 14, 2014, now abandoned, said application No. 14/948,308 is a continuation-in-part of application No. 14/132,292, filed on Dec. 18, 2013, now Pat. No. 9,442,100, said application No. 14/951,475 is a continuation-in-part of application No. 14/071,112, filed on Nov. 4, 2013, now abandoned, and a continuation-in-part of application No. 13/901,131, filed on May 23, 2013, now Pat. No. 9,536,449, said application No. 14/948,308 is a continuation-in-part of application No. 13/901,099, filed on May 23, 2013, now Pat. No. 9,254,099, said application No. 14/992,073 is a continuation-in-part of application No. 13/616,238, filed on Sep. 14, 2012, now abandoned, said application No. 14/330,649 is a continuation-in-part of application No. 13/523,739, filed on Jun. 14, 2012, now Pat. No. 9,042,596.

(60) Provisional application No. 63/542,077, filed on Oct. 2, 2023, provisional application No. 63/279,773, filed on Nov. 16, 2021, provisional application No. 63/171,838, filed on Apr. 7, 2021, provisional application No. 62/930,013, filed on Nov. 4, 2019, provisional application No. 62/857,942, filed on Jun. 6, 2019, provisional application No. 62/814,692, filed on Mar. 6, 2019, provisional application No. 62/814,713, filed on Mar. 6, 2019, provisional application No. 62/800,478, filed on Feb. 2, 2019, provisional application No. 62/549,587, filed on Aug. 24, 2017, provisional application No. 62/439,147, filed on Dec. 26, 2016, provisional application No. 62/349,277, filed on Jun. 13, 2016, provisional application No. 62/311,462, filed on Mar. 22, 2016, provisional application No. 62/997,827, filed on Feb. 20, 2016, provisional application No. 62/245,311, filed on Oct. 23, 2015, provisional application No. 61/932,517, filed on Jan. 28, 2014.

(56) References Cited

U.S. PATENT DOCUMENTS 8,868,149 B2 10/2014 Eisen et al.
9,149,216 B1 10/2015 Eisen et al.
9,314,197 B2 4/2016 Eisen et al.
9,392,946 B1* 7/2016 Sarantos ............ A61B 5/14552
9,498,158 B2 11/2016 Isaacson
9,582,034 B2 2/2017 Von Badinski et al.
9,642,578 B2 5/2017 Newberry
9,730,622 B2 8/2017 Eisen et al.
9,861,314 B2 1/2018 Haverinen et al.
9,980,676 B2 5/2018 Newberry
10,102,342 B1 10/2018 Vleugels et al.
10,139,859 B2 11/2018 von Badinski et al.
10,156,867 B2 12/2018 von Badinski et al.
10,317,200 B1 6/2019 Han et al.
10,321,860 B2 6/2019 Newberry
10,331,168 B2 6/2019 von Badinski et al.
10,349,847 B2 7/2019 Kwon et al.
10,357,165 B2 7/2019 Yoon
10,373,716 B2 8/2019 Vleugels et al.
10,401,800 B2 9/2019 Cardinali et al.
10,423,045 B2 9/2019 Roberts et al.
10,444,834 B2 10/2019 Vescovi
10,496,131 B2 12/2019 von Badinski et al.
10,739,820 B2 8/2020 Wang et al.
10,768,666 B2 9/2020 von Badinski et al.
10,790,054 B1 9/2020 Vleugels et al.
10,842,429 B2 11/2020 Kinnunen et al.
10,884,455 B2 1/2021 von Badinski et al.
10,893,833 B2 1/2021 Haverinen et al.
10,901,460 B2 1/2021 von Badinski et al.
10,952,670 B2 3/2021 Mori et al.
11,188,124 B2 11/2021 von Badinski et al.
11,188,160 B1 11/2021 Liu
11,275,453 B1 3/2022 Tham et al.
11,291,378 B2 4/2022 Laakkonen et al.
11,462,107 B1 10/2022 Sanchez
11,479,258 B1 10/2022 Sanchez
11,540,599 B1 1/2023 Yokoyama et al.
11,580,300 B1 2/2023 Tham et al.
11,599,147 B2 3/2023 von Badinski et al.
11,660,228 B2 5/2023 Goff et al.
11,666,230 B1 6/2023 Piccinini et al.
11,714,494 B2 8/2023 D'Amone et al.
11,733,790 B2 8/2023 Beyhs et al.
11,829,831 B1 11/2023 Ershov et al.
11,850,069 B1 12/2023 Mars et al.
11,862,037 B1 1/2024 Seymore et al.
11,864,871 B2 1/2024 Kang et al.
11,868,178 B2 1/2024 von Badinski et al.
11,868,179 B2 1/2024 von Badinski et al.
11,874,701 B2 1/2024 von Badinski et al.
11,874,702 B2 1/2024 von Badinski et al.
11,895,383 B2 2/2024 Prushinskiy et al.
11,902,791 B2 2/2024 Mars et al.
11,911,181 B1 2/2024 Huttunen et al.
11,916,900 B2 2/2024 Mars et al.
11,925,441 B1 3/2024 Rantanen et al.
11,937,905 B2 3/2024 Singleton et al.
11,949,673 B1 4/2024 Sanchez
11,980,439 B2 5/2024 Koskela et al.
12,007,727 B2 6/2024 Leith et al.
12,013,725 B2 6/2024 von Badinski et al.
12,042,258 B2 7/2024 Laakkonen et al.
12,074,637 B2 8/2024 Vallius et al.
12,076,142 B2 9/2024 Venugopal et al.
2002/0169381 A1* 11/2002 Asada ................ A61B 5/14552 600/500
2011/0082355 A1 4/2011 Eisen et al.
2013/0131475 A1 5/2013 Eisen et al.
2014/0058226 A1 2/2014 Chernobro et al.
2014/0200423 A1 7/2014 Eisen et al.
2014/0255882 A1 9/2014 Hadad et al.
2015/0105638 A1 4/2015 Eisen et al.
2015/0220109 A1 8/2015 von Badinski et al.
2016/0097716 A1* 4/2016 Gulati .................. A61B 5/1495 250/340
2016/0146726 A1 5/2016 Aggarwal
2016/0166161 A1* 6/2016 Yang .................. A61B 5/02427 600/476
2016/0206251 A1 7/2016 Kwon et al.
2016/0246326 A1 8/2016 Von Badinski et al.
2016/0262673 A1 9/2016 Skorich et al.
2016/0278676 A1 9/2016 Eisen et al.
2016/0292563 A1 10/2016 Park
2016/0338601 A1 11/2016 Yang
2016/0350581 A1 12/2016 Manuel et al.
2017/0071518 A1 3/2017 Xavier Da Silveira
2017/0156634 A1 6/2017 Li et al.
2017/0196493 A1 7/2017 Isaacson
2017/0209095 A1 7/2017 Wagner et al.
2017/0220772 A1 8/2017 Vleugels et al.
2017/0224263 A1 8/2017 Lobbestael et al.
2017/0231566 A1 8/2017 Klimek et al.
2017/0235332 A1 8/2017 von Badinski et al.
2017/0235933 A1 8/2017 von Badinski et al.
2017/0249445 A1 8/2017 Devries et al.
2017/0292908 A1 10/2017 Wilk et al.
2017/0303788 A1 10/2017 Xavier Da Silveira
2017/0311823 A1 11/2017 Rausch et al.
2017/0319131 A1 11/2017 Xavier Da Silveira
2017/0325742 A1 11/2017 Prior et al.
2018/0020979 A1 1/2018 Wagner et al.
2018/0042554 A1 2/2018 Wagner et al.
2018/0055449 A1 3/2018 Ko et al.
2018/0070850 A1 3/2018 Stafford et al.
2018/0074010 A1 3/2018 Wang et al.
2018/0074012 A1 3/2018 Wang et al.
2018/0078209 A1 3/2018 Wagner et al.
2018/0103883 A1 4/2018 Darty et al.
2018/0103902 A1 4/2018 Haverinen et al.
2018/0123629 A1 5/2018 Wetzig
2018/0136042 A1 5/2018 Goldring et al.
2018/0140237 A1 5/2018 Rajan et al.
2018/0140238 A1 5/2018 Johnson et al.
2018/0143073 A1 5/2018 Goldring et al.
2018/0143150 A1 5/2018 Bezemer et al.
2018/0214077 A1 8/2018 Dunki-Jacobs
2018/0220906 A1 8/2018 LeBoeuf et al.
2018/0252580 A2 9/2018 Goldring et al.
2018/0271448 A1 9/2018 Bynam et al.
2018/0300458 A1 10/2018 Vleugels et al.
2018/0317786 A1 11/2018 Kulach et al.
2018/0325431 A1 11/2018 Guarin et al.
2018/0333107 A1 11/2018 Sada et al.
2018/0353137 A1* 12/2018 Balajadia .............. A61B 5/681
2019/0013368 A1 1/2019 Chung et al.
2019/0025120 A1 1/2019 Lee et al.
2019/0033130 A1 1/2019 Goldring et al.
2019/0033132 A1 1/2019 Goldring et al.
2019/0033217 A1 1/2019 Kim
2019/0041265 A1 2/2019 Rosen et al.
2019/0049296 A1 2/2019 Cho et al.
2019/0067257 A1 2/2019 Yeon et al.
2019/0069843 A1 3/2019 Chatterjee et al.
2019/0104942 A1 4/2019 Peru et al.
2019/0113387 A1 4/2019 Lee et al.
2019/0117140 A1 4/2019 Al-Ali et al.
2019/0120689 A1 4/2019 Leem et al.
2019/0133469 A1 5/2019 Just et al.
2019/0142313 A1 5/2019 Abou Ismail et al.
2019/0150746 A1 5/2019 Kim
2019/0154584 A1 5/2019 Ahn et al.
2019/0155385 A1 5/2019 Lim et al.
2019/0159703 A1 5/2019 Aggarwal et al.
2019/0167170 A1 6/2019 Varsavsky et al.
2019/0167190 A1 6/2019 Choi et al.
2019/0167201 A1 6/2019 Xavier Da Silveira
2019/0200883 A1 7/2019 Moon et al.
2019/0204865 A1 7/2019 von Badinski et al.
2019/0216322 A1 7/2019 Anikanov et al.

(56) References Cited

U.S. PATENT DOCUMENTS

2019/0216340 A1 7/2019 Holz et al.
2019/0236465 A1 8/2019 Vleugels
2019/0244541 A1 8/2019 Hadad et al.
2019/0244704 A1 8/2019 Kim et al.
2019/0246977 A1 8/2019 Miller et al.
2019/0252569 A1 8/2019 Jo et al.
2019/0290172 A1 9/2019 Hadad et al.
2019/0333634 A1 10/2019 Vleugels et al.
2019/0384354 A1 12/2019 von Badinski et al.
2020/0000351 A1* 1/2020 Rauhala ............... A61B 5/6831
2020/0089272 A1 3/2020 von Badinski et al.
2020/0294645 A1 9/2020 Vleugels
2020/0381101 A1 12/2020 Vleugels
2020/0401183 A1 12/2020 von Badinski et al.
2021/0072833 A1 3/2021 Mutlu et al.
2021/0089126 A1 3/2021 Nickerson
2021/0204815 A1 7/2021 Koskela et al.
2021/0289897 A1 9/2021 Hsu et al.
2021/0307686 A1 10/2021 Catani et al.
2021/0350920 A1 11/2021 Vleugels et al.
2022/0012467 A1 1/2022 Kuo et al.
2022/0057832 A1 2/2022 von Badinski et al.
2022/0085841 A1 3/2022 Gretarsson et al.
2022/0091683 A1 3/2022 Beyhs et al.
2022/0296117 A1 9/2022 Laakkonen et al.
2022/0334639 A1 10/2022 Sanchez
2022/0383741 A1 12/2022 Sanchez
2022/0386885 A1 12/2022 Lee et al.
2022/0407550 A1 12/2022 Gretarsson et al.
2022/0409072 A1 12/2022 Kang et al.
2023/0000405 A1 1/2023 Lee et al.
2023/0007884 A1 1/2023 Kang et al.
2023/0008487 A1 1/2023 Caizzone et al.
2023/0021838 A1 1/2023 Tse et al.
2023/0034807 A1 2/2023 McDaniel et al.
2023/0043018 A1 2/2023 Wai et al.
2023/0053252 A1 2/2023 Jung
2023/0056434 A1 2/2023 Jang et al.
2023/0070636 A1 3/2023 Kang et al.
2023/0072436 A1 3/2023 Sanchez
2023/0079736 A1 3/2023 Makinen
2023/0081794 A1 3/2023 Makinen et al.
2023/0085555 A1 3/2023 Nomvar et al.
2023/0113714 A1 4/2023 Vallius et al.
2023/0118067 A1 4/2023 Chang et al.
2023/0143293 A1 5/2023 Sanchez
2023/0153416 A1 5/2023 Sanchez
2023/0157645 A1 5/2023 Lee et al.
2023/0174114 A1 6/2023 Sanchez
2023/0178213 A1 6/2023 Haertel et al.
2023/0190118 A1 6/2023 Park et al.
2023/0190197 A1 6/2023 Huttunen
2023/0190201 A1 6/2023 Singleton et al.
2023/0200744 A1 6/2023 Choi et al.
2023/0205170 A1 6/2023 Sanchez
2023/0205325 A1 6/2023 Khan
2023/0213970 A1 7/2023 von Badinski et al.
2023/0218192 A1 7/2023 Eom et al.
2023/0225671 A1 7/2023 Kosman et al.
2023/0225676 A1 7/2023 Halpern et al.
2023/0233084 A1 7/2023 Moon et al.
2023/0297858 A1 9/2023 Vleugels et al.
2023/0301540 A1 9/2023 Jung et al.
2023/0309844 A1 10/2023 Jang et al.
2023/0324293 A1 10/2023 Lee
2023/0350492 A1 11/2023 Nickerson
2023/0350503 A1 11/2023 D'Amone et al.
2023/0359291 A1 11/2023 Beyhs et al.
2023/0361588 A1 11/2023 Sanchez
2023/0376071 A1 11/2023 von Badinski et al.
2023/0376072 A1 11/2023 von Badinski et al.
2023/0380692 A1 11/2023 Huttunen et al.
2023/0384827 A1 11/2023 von Badinski et al.
2023/0409080 A1 12/2023 von Badinski et al.
2024/0000328 A1 1/2024 Kangas et al.
2024/0000380 A1 1/2024 Fei et al.
2024/0000387 A1 1/2024 Realubit et al.
2024/0012479 A1 1/2024 Qiu et al.
2024/0045473 A1 2/2024 Lee et al.
2024/0046505 A1 2/2024 Liu et al.
2024/0048675 A1 2/2024 Choi et al.
2024/0058686 A1 2/2024 Bhandarkar et al.
2024/0065631 A1 2/2024 Brooks
2024/0081663 A1 3/2024 Park et al.
2024/0112563 A1 4/2024 Norman et al.
2024/0115212 A1 4/2024 Jang et al.
2024/0122548 A1 4/2024 Kangas et al.
2024/0122550 A1 4/2024 Syrjala et al.
2024/0125915 A1 4/2024 Au et al.
2024/0126328 A1 4/2024 von Badinski et al.
2024/0126329 A1 4/2024 von Badinski et al.
2024/0126330 A1 4/2024 von Badinski et al.
2024/0126382 A1 4/2024 Yoo
2024/0134417 A1 4/2024 von Badinski et al.
2024/0138721 A1 5/2024 Eom et al.
2024/0143027 A1 5/2024 von Badinski et al.
2024/0143028 A1 5/2024 von Badinski et al.
2024/0146350 A1 5/2024 Gretarsson et al.
2024/0168521 A1 5/2024 von Badinski et al.
2024/0172945 A1 5/2024 Park et al.
2024/0176425 A1 5/2024 Wang et al.
2024/0179550 A1 5/2024 Au et al.
2024/0188834 A1 6/2024 Kwon et al.
2024/0188881 A1 6/2024 Bonificio et al.
2024/0201736 A1 6/2024 von Badinski et al.
2024/0237904 A1 7/2024 Makinen et al.
2024/0241541 A1 7/2024 Makinen
2024/0293084 A1 9/2024 Huttunen et al.
2024/0298966 A1 9/2024 Ariza-Zambrano et al.
2024/0364420 A1 10/2024 Vallius et al.

* cited by examiner

BIOMETRIC WEARABLE DEVICE (E.G. FINGER RING OR SMART WATCH) WITH OPTICAL SENSORS AND BODY-FACING PROTRUSIONS

CROSS-REFERENCE TO RELATED APPLICATIONS

This application is a continuation-in-part of U.S. patent application Ser. No. 18/929,026 filed on 2024 Oct. 28. This application is a continuation-in-part of U.S. patent application Ser. No. 18/885,728 filed on 2024 Sep. 15. This application is a continuation-in-part of U.S. patent application Ser. No. 18/775,128 filed on 2024 Jul. 17. This application is a continuation-in-part of U.S. patent application Ser. No. 18/617,950 filed on 2024 Mar. 27. This application is a continuation-in-part of U.S. patent application Ser. No. 18/121,841 filed on 2023 Mar. 15.

U.S. patent application Ser. No. 18/929,026 was a continuation-in-part of U.S. patent application Ser. No. 18/885,728 filed on 2024 Sep. 15. U.S. patent application Ser. No. 18/929,026 was a continuation-in-part of U.S. patent application Ser. No. 18/775,128 filed on 2024 Jul. 17. U.S. patent application Ser. No. 18/929,026 was a continuation-in-part of U.S. patent application Ser. No. 18/121,841 filed on 2023 Mar. 15.

U.S. patent application Ser. No. 18/885,728 was a continuation-in-part of U.S. patent application Ser. No. 18/775,128 filed on 2024 Jul. 17. U.S. patent application Ser. No. 18/885,728 was a continuation-in-part of U.S. patent application Ser. No. 18/617,950 filed on 2024 Mar. 27. U.S. patent application Ser. No. 18/885,728 claimed the priority benefit of U.S. provisional application 63/542,077 filed on 2023 Oct. 2. U.S. patent application Ser. No. 18/885,728 was a continuation-in-part of U.S. patent application Ser. No. 18/121,841 filed on 2023 Mar. 15.

U.S. patent application Ser. No. 18/775,128 was a continuation-in-part of U.S. patent application Ser. No. 18/617,950 filed on 2024 Mar. 27. U.S. patent application Ser. No. 18/775,128 was a continuation-in-part of U.S. patent application Ser. No. 18/121,841 filed on 2023 Mar. 15.

U.S. patent application Ser. No. 18/617,950 claimed the priority benefit of U.S. provisional application 63/542,077 filed on 2023 Oct. 2. U.S. patent application Ser. No. 18/617,950 was a continuation-in-part of U.S. patent application Ser. No. 18/121,841 filed on 2023 Mar. 15.

U.S. patent application Ser. No. 18/121,841 was a continuation-in-part of U.S. patent application Ser. No. 17/903,746 filed on 2022 Sep. 6. U.S. patent application Ser. No. 18/121,841 was a continuation-in-part of U.S. patent application Ser. No. 17/239,960 filed on 2021 Apr. 26. U.S. patent application Ser. No. 18/121,841 was a continuation-in-part of U.S. patent application Ser. No. 16/737,052 filed on 2020 Jan. 8.

U.S. patent application Ser. No. 17/903,746 was a continuation-in-part of U.S. patent application Ser. No. 16/568,580 filed on 2019 Sep. 12. U.S. patent application Ser. No. 17/903,746 was a continuation-in-part of U.S. patent application Ser. No. 16/737,052 filed on 2020 Jan. 8. U.S. patent application Ser. No. 17/903,746 was a continuation-in-part of U.S. patent application Ser. No. 17/239,960 filed on 2021 Apr. 26. U.S. patent application Ser. No. 17/903,746 claimed the priority benefit of U.S. provisional application 63/279,773 filed on 2021 Nov. 16.

U.S. patent application Ser. No. 17/239,960 claimed the priority benefit of U.S. provisional application 63/171,838 filed on 2021 Apr. 7. U.S. patent application Ser. No. 17/239,960 was a continuation-in-part of U.S. patent application Ser. No. 16/737,052 filed on 2020 Jan. 8.

U.S. patent application Ser. No. 16/737,052 claimed the priority benefit of U.S. provisional application 62/930,013 filed on 2019 Nov. 4. U.S. patent application Ser. No. 16/737,052 claimed the priority benefit of U.S. provisional application 62/857,942 filed on 2019 Jun. 6. U.S. patent application Ser. No. 16/737,052 claimed the priority benefit of U.S. provisional application 62/814,713 filed on 2019 Mar. 6. U.S. patent application Ser. No. 16/737,052 claimed the priority benefit of U.S. provisional application 62/814,692 filed on 2019 Mar. 6. U.S. patent application Ser. No. 16/737,052 claimed the priority benefit of U.S. provisional application 62/800,478 filed on 2019 Feb. 2. U.S. patent application Ser. No. 16/737,052 was a continuation-in-part of U.S. patent application Ser. No. 16/568,580 filed on 2019 Sep. 12. U.S. patent application Ser. No. 16/737,052 was a continuation-in-part of U.S. patent application Ser. No. 15/963,061 filed on 2018 Apr. 25 which issued as U.S. Pat. No. 10,772,559 on 2020 Sep. 15. U.S. patent application Ser. No. 16/737,052 was a continuation-in-part of U.S. patent application Ser. No. 15/725,330 filed on 2017 Oct. 5 which issued as U.S. Pat. No. 10,607,507 on 2020 Mar. 31. U.S. patent application Ser. No. 16/737,052 was a continuation-in-part of U.S. patent application Ser. No. 15/431,769 filed on 2017 Feb. 14. U.S. patent application Ser. No. 16/737,052 was a continuation-in-part of U.S. patent application Ser. No. 15/294,746 filed on 2016 Oct. 16 which issued as U.S. Pat. No. 10,627,861 on 2020 Apr. 21.

U.S. patent application Ser. No. 16/568,580 claimed the priority benefit of U.S. provisional application 62/857,942 filed on 2019 Jun. 6. U.S. patent application Ser. No. 16/568,580 claimed the priority benefit of U.S. provisional application 62/814,713 filed on 2019 Mar. 6. U.S. patent application Ser. No. 16/568,580 claimed the priority benefit of U.S. provisional application 62/814,692 filed on 2019 Mar. 6. U.S. patent application Ser. No. 16/568,580 was a continuation-in-part of U.S. patent application Ser. No. 15/963,061 filed on 2018 Apr. 25 which issued as U.S. Pat. No. 10,772,559 on 2020 Sep. 15. U.S. patent application Ser. No. 16/568,580 was a continuation-in-part of U.S. patent application Ser. No. 15/725,330 filed on 2017 Oct. 5 which issued as U.S. Pat. No. 10,607,507 on 2020 Mar. 31. U.S. patent application Ser. No. 16/568,580 was a continuation-in-part of U.S. patent application Ser. No. 15/431,769 filed on 2017 Feb. 14. U.S. patent application Ser. No. 16/568,580 was a continuation-in-part of U.S. patent application Ser. No. 15/418,620 filed on 2017 Jan. 27. U.S. patent application Ser. No. 16/568,580 was a continuation-in-part of U.S. patent application Ser. No. 15/294,746 filed on 2016 Oct. 16 which issued as U.S. Pat. No. 10,627,861 on 2020 Apr. 21.

U.S. patent application Ser. No. 15/963,061 was a continuation-in-part of U.S. patent application Ser. No. 14/992,073 filed on 2016 Jan. 11. U.S. patent application Ser. No. 15/963,061 was a continuation-in-part of U.S. patent application Ser. No. 14/550,953 filed on 2014 Nov. 22.

U.S. patent application Ser. No. 15/725,330 claimed the priority benefit of U.S. provisional application 62/549,587 filed on 2017 Aug. 24. U.S. patent application Ser. No. 15/725,330 claimed the priority benefit of U.S. provisional application 62/439,147 filed on 2016 Dec. 26. U.S. patent application Ser. No. 15/725,330 was a continuation-in-part of U.S. patent application Ser. No. 15/431,769 filed on 2017 Feb. 14. U.S. patent application Ser. No. 15/725,330 was a continuation-in-part of U.S. patent application Ser. No. 14/951,475 filed on 2015 Nov. 24 which issued as U.S. Pat. No. 10,314,492 on 2019 Jun. 11.

U.S. patent application Ser. No. 15/431,769 claimed the priority benefit of U.S. provisional application 62/439,147 filed on 2016 Dec. 26. U.S. patent application Ser. No. 15/431,769 claimed the priority benefit of U.S. provisional application 62/349,277 filed on 2016 Jun. 13. U.S. patent application Ser. No. 15/431,769 claimed the priority benefit of U.S. provisional application 62/311,462 filed on 2016 Mar. 22. U.S. patent application Ser. No. 15/431,769 was a continuation-in-part of U.S. patent application Ser. No. 15/294,746 filed on 2016 Oct. 16 which issued as U.S. Pat. No. 10,627,861 on 2020 Apr. 21. U.S. patent application Ser. No. 15/431,769 was a continuation-in-part of U.S. patent application Ser. No. 15/206,215 filed on 2016 Jul. 8. U.S. patent application Ser. No. 15/431,769 was a continuation-in-part of U.S. patent application Ser. No. 14/992,073 filed on 2016 Jan. 11. U.S. patent application Ser. No. 15/431,769 was a continuation-in-part of U.S. patent application Ser. No. 14/330,649 filed on 2014 Jul. 14.

U.S. patent application Ser. No. 15/418,620 claimed the priority benefit of U.S. provisional application 62/297,827 filed on 2016 Feb. 20. U.S. patent application Ser. No. 15/418,620 was a continuation-in-part of U.S. patent application Ser. No. 14/951,475 filed on 2015 Nov. 24 which issued as U.S. Pat. No. 10,314,492 on 2019 Jun. 11.

U.S. patent application Ser. No. 15/294,746 claimed the priority benefit of U.S. provisional application 62/349,277 filed on 2016 Jun. 13. U.S. patent application Ser. No. 15/294,746 claimed the priority benefit of U.S. provisional application 62/245,311 filed on 2015 Oct. 23. U.S. patent application Ser. No. 15/294,746 was a continuation-in-part of U.S. patent application Ser. No. 14/951,475 filed on 2015 Nov. 24 which issued as U.S. Pat. No. 10,314,492 on 2019 Jun. 11.

U.S. patent application Ser. No. 15/206,215 claimed the priority benefit of U.S. provisional application 62/349,277 filed on 2016 Jun. 13. U.S. patent application Ser. No. 15/206,215 was a continuation-in-part of U.S. patent application Ser. No. 14/951,475 filed on 2015 Nov. 24 which issued as U.S. Pat. No. 10,314,492 on 2019 Jun. 11. U.S. patent application Ser. No. 15/206,215 was a continuation-in-part of U.S. patent application Ser. No. 14/948,308 filed on 2015 Nov. 21.

U.S. patent application Ser. No. 14/992,073 was a continuation-in-part of U.S. patent application Ser. No. 14/562,719 filed on 2014 Dec. 7 which issued as U.S. Pat. No. 10,130,277 on 2018 Nov. 20. U.S. patent application Ser. No. 14/992,073 was a continuation-in-part of U.S. patent application Ser. No. 13/616,238 filed on 2012 Sep. 14.

U.S. patent application Ser. No. 14/951,475 was a continuation-in-part of U.S. patent application Ser. No. 14/071,112 filed on 2013 Nov. 4. U.S. patent application Ser. No. 14/951,475 was a continuation-in-part of U.S. patent application Ser. No. 13/901,131 filed on 2013 May 23 which issued as U.S. Pat. No. 9,536,449 on 2017 Jan. 3.

U.S. patent application Ser. No. 14/948,308 was a continuation-in-part of U.S. patent application Ser. No. 14/550,953 filed on 2014 Nov. 22. U.S. patent application Ser. No. 14/948,308 was a continuation-in-part of U.S. patent application Ser. No. 14/449,387 filed on 2014 Aug. 1. U.S. patent application Ser. No. 14/948,308 was a continuation-in-part of U.S. patent application Ser. No. 14/132,292 filed on 2013 Dec. 18 which issued as U.S. Pat. No. 9,442,100 on 2016 Sep. 13. U.S. patent application Ser. No. 14/948,308 was a continuation-in-part of U.S. patent application Ser. No. 13/901,099 filed on 2013 May 23 which issued as U.S. Pat. No. 9,254,099 on 2016 Feb. 9.

U.S. patent application Ser. No. 14/562,719 claimed the priority benefit of U.S. provisional application 61/932,517 filed on 2014 Jan. 28.

U.S. patent application Ser. No. 14/330,649 was a continuation-in-part of U.S. patent application Ser. No. 13/523,739 filed on 2012 Jun. 14 which issued as U.S. Pat. No. 9,042,596 on 2015 May 26.

The entire contents of these applications are incorporated herein by reference.

FEDERALLY SPONSORED RESEARCH

Not Applicable

SEQUENCE LISTING OR PROGRAM

Not Applicable

BACKGROUND—FIELD OF INVENTION

This invention relates to wearable devices for measuring biometric parameters.

INTRODUCTION

Biometric wearable devices such as smart finger rings and smart watches with optical sensors have advantages over mobile handheld devices (such as cellphones) and non-mobile devices (such as stationary medical equipment) for monitoring a person's biometric parameters: to diagnosis adverse health conditions; to provide an alert in case of an adverse health event; to provide a feedback and/or control loop for the operation of implanted medical devices; and to help people maintain their health and prevent illness. Due to their consistent proximity to a person's body and their easily transportable nature, these devices can monitor biometric parameters more broadly and consistently than handheld devices. There are also challenges in the development of biometric wearable devices. For example, they are relatively small, which can make it difficult for them to house complex components. Also, they can shift or rotate on a person's finger, wrist, or arm. However, these challenges are not insurmountable and are addressed by some of the innovative designs disclosed herein.

REVIEW OF THE RELEVANT ART

U.S. patent application No. 20140058226 (Chernobro et al., Feb. 27, 2014, "Method and Apparatus for In Vivo Optical Measurement of Blood Glucose Concentration") discloses using differential scattering spectroscopy and Doppler microscopy to measure blood glucose. U.S. Pat. No. 8,725,226 (Isaacson, May 13, 2014, "Optical Sensor Path Selection") discloses a device with multiple possible pairings of light emitters and detectors to scan different tissue depths for biometric measurement.

U.S. Pat. No. 8,868,149 (Eisen et al., Oct. 21, 2014, "Photoplethysmography Device and Method") and U.S. Pat. No. 9,149,216 (Eisen et al., Oct. 6, 2015, "Photoplethysmography Device and Method") and U.S. patent applications 20110082355 (Eisen et al., Apr. 7, 2011, "Photoplethysmography Device and Method"), 20130131475 (Eisen et al., May 23, 2013, "Photoplethysmography Device and Method"), and 20150105638 (Eisen et al., Apr. 16, 2015, "Photoplethysmography Device and Method") disclose using photoplethysmography and dynamic light scattering for biometric measurement.

U.S. patent application No. 20150220109 (von Badinski et al., Aug. 6, 2015, "Wearable Computing Device") and U.S. Pat. No. 9,582,034 (von Badinski et al., Feb. 28, 2017, "Wearable Computing Device") disclose a finger ring comprising an interior wall, an exterior wall, a flexible circuit board, and a window that facilitates data transmission, battery recharge, and/or status indication. U.S. Pat. No. 9,314,197 (Eisen et al., Apr. 19, 2016, "Wearable Pulse Oximetry Device") and U.S. patent application 20140200423 (Eisen et al., Jul. 17, 2014, "Wearable Pulse Oximetry Device") disclose a wrist-worn pulse oximetry device which is worn over the ulna. U.S. patent application No. 20160146726 (Aggarwal, May 26, 2016, "Wearable Device for Detection of Contaminants and Method Thereof") discloses a wearable spectrometer for analyzing the chemical composition of substances.

U.S. patent application No. 20160206251 (Kwon et al., Jul. 21, 2016, "Apparatus for Detecting Bio-Information") and U.S. Pat. No. 10,349,847 (Kwon et al., Jul. 6, 2019, "Apparatus for Detecting Bio-Information") disclose an apparatus with a light-emitting diode (LED), a laser diode (LD), and an optical detector. U.S. patent application No. 20160246326 (von Badinski et al., Aug. 25, 2016, "Wearable Computing Device") discloses a device charger which directs artificial light toward a device. U.S. patent application 20160262673 (Skorich et al., Sep. 15, 2016, "Segmented Sensor") discloses an optical biometric sensor with a planar substrate. U.S. patent application No. 20160292563 (Park, Oct. 6, 2016, "Smart Ring") discloses systems and methods for pairing a smart ring with a primary device.

U.S. Pat. No. 9,498,158 (Isaacson, Nov. 22, 2016, "Optical Sensor Path Selection") discloses a device with multiple light emitters to scan different tissue depths for biometric measurement. U.S. patent application No. 20160338601 (Yang, 2016 Nov. 24, "Optical Fiber Continuous Detecting Blood Sensor and Wearing Apparatus Thereof") discloses using optical fibers and spectroscopic sensors to measure blood pressure. U.S. patent application No. 20160350581 (Manuel et al., Dec. 1, 2016, "Smart Ring with Biometric Sensor") discloses a ring comprising a ring body and a biometric sensor. U.S. patent application No. 20170071518 (Xavier Da Silveira et al., Mar. 16, 2017, "Apparatus and Method for Optical Tissue Detection") discloses optical discrimination between body tissue and non-tissue materials.

U.S. Pat. No. 9,642,578 (Newberry, May 9, 2017, "System and Method for Health Monitoring Using a Non-Invasive, Multi-Band Biosensor") and U.S. Pat. No. 9,980,676 (Newberry, May 29, 2018, "System and Method for Health Monitoring Using a Non-Invasive, Multi-Band Biosensor") disclose a PPG sensor which uses multiple wavelengths. U.S. patent application No. 20170156634 (Li et al., Jun. 8, 2017, "Wearable Device and Method for Monitoring Eating") and U.S. Pat. No. 10,499,833 (Li et al., Dec. 10, 2019, "Wearable Device and Method for Monitoring Eating") disclose a wearable device with an acceleration sensor to monitor eating. U.S. patent application No. 20170196493 (Isaacson, Jul. 13, 2017, "Optical Sensor Path Selection") discloses a device with multiple optical elements and detectors to measure a biometric parameter.

U.S. patent application No. 20170209095 (Wagner et al., Jul. 27, 2017, "Optical Physiological Sensor Modules with Reduced Signal Noise") discloses an optical sensor module with light guides which have outwardly-diverging axial directions. U.S. patent application No. 20170224263 (Lobbestael et al., Aug. 10, 2017, "Tissue Site Detection") discloses an optical biometric sensor which identifies a particular tissue site. U.S. Pat. No. 9,730,622 (Eisen et al., Aug. 15, 2017, "Wearable Pulse Oximetry Device") and U.S. patent application No. 20160278676 (Eisen et al., Sep. 29, 2016, "Wearable Pulse Oximetry Device") disclose a wearable pulse oximetry device with two light emitters with two different wavelengths. U.S. patent application No. 20170231566 (Klimek et al., Aug. 17, 2017, "Tissue Interface") discloses a garment with a sensor module for biometric measurement. U.S. patent application No. 20170235332 (von Badinski et al., Aug. 17, 2017, "Wearable Computing Device") discloses a wearable computing device with a photovoltaic element and a base assembly with a concentrated light source directed at the photovoltaic element.

U.S. patent application No. 20170235933 (von Badinski et al., Aug. 17, 2017, "Wearable Computing Device") and U.S. Pat. No. 10,156,867 (von Badinski et al., Dec. 18, 2018, "Wearable Computing Device") disclose a method for using a finger ring to identify an authorized user by illuminating a portion of the user's skin, imaging the portion, and then generating a capillary map. U.S. patent application No. 20170249445 (Devries et al., Aug. 31, 2017, "Portable Devices and Methods for Measuring Nutritional Intake") discloses a nutritional intake monitoring system with biosensors. U.S. patent applications 20170292908 (Wilk et al., Oct. 12, 2017, "Spectrometry System Applications") and 20180143073 (Goldring et al., May 24, 2018, "Spectrometry System Applications") disclose a spectrometer system to determine spectra of an object.

U.S. patent application No. 20170303788 (Xavier Da Silveira et al., Oct. 26, 2017, "Wearable Device for Tissue Monitoring with Effective Ambient Light Blocking") discloses an optical biometric device with a shield to block ambient light. U.S. patent application No. 20170311823 (Rausch et al., Nov. 2, 2017, "Optical Trigger for Measurement") discloses detecting and using feature in a photoplethysmogram signal for biometric measurement. U.S. patent application No. 20170319131 (Xavier Da Silveira et al., Nov. 9, 2017, "Method and Device for Hydration Monitoring") discloses using three different wavelengths to measure hydration. U.S. patent application No. 20170325742 (Prior et al., Nov. 16, 2017, "Universal Fingertip Sensor") discloses a finger-tip-worn optical biometric sensor device. U.S. Pat. No. 9,861,314 (Haverinen et al., Jan. 9, 2018, "Wearable Electronic Device and Method for Manufacturing Thereof") discloses a wearable electronic device including a molded body part made of a moldable ceramic material.

U.S. patent application No. 20180020979 (Wagner et al., Jan. 25, 2018, "Optical Adapters for Wearable Monitoring Devices") discloses a wearable optical biometric sensor with stabilizing members. U.S. patent application No. 20180042554 (Wagner et al., Feb. 15, 2018, "Optical Monitoring Apparatus and Methods") discloses a biometric device with a digital camera and a photoplethysmography (PPG) sensor. U.S. patent application No. 20180055449 (Ko et al., Mar. 1, 2018, "Wearable Measurement Apparatus") discloses a wearable biometric device with elastic portions. U.S. patent application No. 20180070850 (Stafford et al., Mar. 15, 2018, "Apparatus and Method for Detecting Body Composition and Correlating It With Cognitive Efficiency") discloses a biometric device to measure body hydration and correlate it with cognitive efficiency.

U.S. patent applications 20180074010 (Wang et al., Mar. 15, 2018, "Application of Electrochemical Impedance Spectroscopy in Sensor Systems, Devices, and Related Methods" and 20180074011 (Wang et al., Mar. 15, 2018, "Application of Electrochemical Impedance Spectroscopy in Sensor Systems, Devices, and Related Methods"), and 20180074012 (Wang et al., Mar. 15, 2018, "Application of Electrochemical Impedance Spectroscopy in Sensor Systems, Devices, and Related Methods") disclose using electrochemical impedance spectroscopy to measure glucose level. U.S. patent application 20180078209 (Wagner et al., Mar. 22, 2018, "Stabilized Sensor Modules and Monitoring Devices Incorporating Same") discloses a wearable optical biometric sensor with stabilizing protrusions. U.S. patent application No. 20180103883 (Darty et al., Apr. 19, 2018, "Systems and Methods for Measuring Tissue Oxygenation") discloses using images with different spectral bands to measure tissue oxygenation.

U.S. patent application No. 20180103902 (Haverinen et al., Apr. 19, 2018, "Wearable Electronic Device and Method for Manufacturing Thereof") and U.S. Pat. No. 10,893,833 (Haverinen et al., Jan. 19, 2021, "Wearable Electronic Device and Method for Manufacturing Thereof") disclose a wearable electronic device made from non-ceramic material. U.S. patent application No. 20180123629 (Wetzig, May 3, 2018, "Smart-Ring Methods and Systems") discloses a computerized smart ring which is embedded with electronics, software, sensors wherein the ring can be electronically connected to another computing system. U.S. patent application No. 20180136042 (Goldring et al., May 17, 2018, "Spectrometry System with Visible Aiming Beam") discloses a handheld spectrometer with a visible aiming beam.

U.S. patent application No. 20180140237 (Rajan et al., May 24, 2018, "Device and Method for Determining Biological Indicator Levels in Tissue") discloses using at least two light emitters to measure a biological parameter. U.S. patent application No. 20180140238 (Johnson et al., May 24, 2018, "Regional Oximetry Sleeve for Mobile Device") discloses a mobile computing device with a sleeve. U.S. patent application No. 20180143150 (Bezemer et al., May 24, 2018, "Apparatus and Methods That Use Magnetic Induction Spectroscopy to Monitor Tissue Fluid Content") discloses using magnetic induction spectroscopy to measure tissue fluid. U.S. patent application No. 20180214077 (Dunki-Jacobs, Aug. 2, 2018, "Meal Detection Devices and Methods") and U.S. Pat. No. 10,791,988 (Dunki-Jacobs, Aug. 2, 2018, "Meal Detection Devices and Methods") disclose using biometric sensors to detect meal intake and control a therapeutic device. U.S. patent application No. 20180220906 (LeBoeuf et al., Aug. 9, 2018, "Physiological Monitoring Apparatus and Networks") discloses ear-worn devices for biometric and environmental monitoring.

U.S. patent application No. 20180252580 (Goldring et al., Sep. 6, 2018, "Low-Cost Spectrometry System for End-User Food Analysis") discloses a compact spectrometer that can be used in mobile devices such as smart phones. U.S. patent application No. 20180271448 (Bynam et al., Sep. 27, 2018, "Method of Enabling Feature Extraction for Glucose Monitoring Using Near-Infrared (NIR) Spectroscopy") discloses using near-infrared (NIR) spectroscopy to measure blood glucose. U.S. patent application No. 20180317786 (Kulach et al., Nov. 8, 2018, "Pulse Spectroscopy") discloses a wearable photoplethysmogram (PPG) sensor. U.S. patent application No. 20180325431 (Guarin et al., Nov. 15, 2018, "Electromagnetic Wave Sensor for Determining a Hydration Status of a Body Tissue In Vivo") discloses using an electromagnetic wave sensor to measure body tissue hydration.

U.S. patent application No. 20180333107 (Garcia Sada et al., Nov. 22, 2018, "Non-Invasive Wearable Device, Process and Systems with Adjustable Operation") discloses a wearable device with a flexible housing and an array of sensors. U.S. Pat. No. 10,139,859 (von Badinski et al., Nov. 27, 2018, "Wearable Computing Device") discloses a wearable ring computing device with a curved battery, a photovoltaic element, and a charging assembly with a concentrated light source. U.S. patent application No. 20190013368 (Chung et al., Jan. 10, 2019, "Near-Infrared Light Organic Sensors, Embedded Organic Light Emitting Diode Panels, and Display Devices Including the Same") discloses an OLED panel which is embedded with a near-infrared organic photosensor, wherein this structure enables biometric recognition.

U.S. patent application No. 20190025120 (Lee et al., Jan. 24, 2019, "Spectrometer and Spectrum Measurement Method Utilizing Same") discloses a spectrometer with a first unit spectral filter which absorbs or reflects light in a part of a wavelength band of a light spectrum of an incident target, a second unit spectral filter which absorbs or reflects light in a wavelength band different from the part of the wavelength band, a first light detector configured to detect a first light spectrum passing through the first unit spectral filter, a second light detector configured to detect a second light spectrum passing through the second unit spectral filter, and a processing unit. U.S. patent application No. 20190033130 (Goldring et al., Jan. 31, 2019, "Spectrometry Systems, Methods, and Applications") discloses a hand held spectrometer with wavelength multiplexing.

U.S. patent application No. 20190033132 (Goldring et al., Jan. 31, 2019, "Spectrometry System with Decreased Light Path") discloses a spectrometer with a plurality of isolated optical channels. U.S. patent application No. 20190033217 (Kim, Jan. 31, 2019, "Spectrum Measurement Apparatus and Spectrum Measurement Method") discloses a spectrum measurement apparatus with a plurality of light sources which emit light at different wavelengths, a light detector, and a processor. U.S. patent application No. 20190041265 (Rosen et al., Feb. 7, 2019, "Spatially Variable Filter Systems and Methods") discloses a compact spectrometer system with a spatially variable filter. U.S. patent application 20190049296 (Cho et al., Feb. 14, 2019, "Light Filter and Spectrometer Including the Light Filter") discloses a spectrometer with different spectrum modulation portions. U.S. patent application 20190067257 (Yeon et al., Feb. 28, 2019, "Light-Emitting Diode (LED) Device") discloses a multi-color display includes a plurality of light-emitting cells at least partially defined by a partition layer.

U.S. patent application No. 20190069843 (Chatterjee et al., Mar. 7, 2019, "Wearable Personal Information System") discloses a wearable optical device with a shield to block ambient light. U.S. patent application No. 20190104942 (Peru et al., Apr. 11, 2019, "Spectroscopic System and Method Therefor") discloses probe which analyzes saliva for biometric measurement. U.S. patent application No. 20190113387 (Lee et al., Apr. 18, 2019, "Spectrometric Sensor Control Method and Electronic Device for Supporting Same") discloses spectroscopic sensor with multiple wavelength bands. U.S. patent application 20190117140 (Al-Ali et al., Apr. 25, 2019, "Advanced Pulse Oximetry Sensor") discloses a pulse oximetry sensor with a light diffuser and light concentrator. U.S. patent application No. 20190120689 (Leem et al., Apr. 25, 2019, "Combination Sensors and Electronic Devices") discloses a biometric device with stacked infrared sensors.

U.S. patent application No. 20190133469 (Just et al., May 9, 2019, "Physiological Monitoring Devices Having Sensing Elements Decoupled from Body Motion") discloses a biometric measuring device with multiple bands to reduce motion artifacts. U.S. patent application No. 20190142313 (Abou Ismail et al., May 16, 2019, "System and Method for Non-Invasive Continuous Real-Time Blood Glucose Monitoring") discloses using an impedance sensor and permittivity to measure blood glucose. U.S. patent application No. 20190150746 (Kim, May 23, 2019, "Bio-Information Measuring Apparatus and Bio-Information Measuring Method") discloses a biometric spectroscopy device with a pressure sensor. U.S. patent application No. 20190154584 (Ahn et al., May 23, 2019, "Spectroscopy Apparatus, Spectroscopy Method, and Bio-Signal Measuring Apparatus") discloses a spectroscopy apparatus with a dispersive element which divides an incident light into a plurality of lights having different output angles.

U.S. patent application No. 20190155385 (Lim et al., May 23, 2019, "Smart Ring Providing Multi-Mode Control in a Personal Area Network") discloses a smart ring which provides multi-mode control in a personal area network. U.S. patent application No. 20190159703 (Aggarwal et al., May 30, 2019, "System and Method for Obtaining Blood Glucose Concentration Using Temporal Independent Component Analysis (ICA)") discloses using near infrared spectroscopy (NIR) to measure blood glucose. U.S. patent application No. 20190167170 (Varsavsky et al., Jun. 6, 2019, "Methods and Systems for Improving the Reliability of Orthogonally Redundant Sensors") discloses using orthogonally redundant sensors to measure glucose level. U.S. patent application 20190167190 (Choi et al., Jun. 6, 2019, "Healthcare Apparatus and Operating Method Thereof") discloses a healthcare apparatus with a plurality of light sources which emit light of different wavelengths, a light detector, and a processor configured to obtain a blood glucose level.

U.S. patent application No. 20190167201 (Xavier Da Silveira et al., Jun. 6, 2019, "Wearable Athletic Monitoring Using Digital Modulation") discloses a wearable spectroscopic sensor with digital modulation. U.S. Pat. No. 10,317,200 (Han et al., Jun. 11, 2019, "Multi-Mode Sensor for Surface Orientation") discloses a wearable device with an orientation sensor and multiple pairings between light emitters and light detectors. U.S. Pat. No. 10,321,860 (Newberry, Jun. 18, 2019, "System and Method for Glucose Monitoring") discloses a glucose biosensor with optical fibers. U.S. Pat. No. 10,331,168 (von Badinski et al., Jun. 25, 2019, "Wearable Computing Device") discloses a timepiece computing system which sends command media player instructions to a second computing device. U.S. patent application No. 20190200883 (Moon et al., Jul. 4, 2019, "Bio-Signal Measuring Apparatus and Operating Method Thereof") discloses a bio-signal measuring apparatus with a photodetector and an array of light sources around the photodetector.

U.S. patent application No. 20190204865 (von Badinski et al., Jul. 4, 2019, "Wearable Computing Device") discloses a wearable smart ring with a curved rechargeable battery, an accelerometer, a gyroscope, a heart rate sensor, an internal measurement unit, and an electrocardiogram sensor. U.S. Pat. No. 10,349,847 (Kwon et al., Jul. 6, 2019, "Apparatus for Detecting Bio-Information") and U.S. patent application No. 20160206251 (Kwon et al., Jul. 21, 2016, "Apparatus for Detecting Bio-Information") disclose using a two-dimensional optical array to measure biometric parameters. U.S. patent application No. 20190216322 (Anikanov et al., Jul. 18, 2019, "Compact Spectrometer System for Non-Invasive Measurement of Absorption and Transmission Spectra in Biological Tissue Samples") discloses a spectrometer for analyzing an inhomogeneous scattering medium. U.S. patent application No. 20190216340 (Holz et al., Jul. 18, 2019, "Sensor Device") discloses a multi-dimensional optical sensor for biometric measurements.

U.S. Pat. No. 10,357,165 (Yoon, Jul. 23, 2019, "Method and Apparatus for Acquiring Bioinformation and Apparatus for Testing Bioinformation") discloses a biometric sensor analyzing laser speckle patterns. U.S. patent application No. 20190236465 (Vleugels, Aug. 1, 2019, "Activation of Ancillary Sensor Systems Based on Triggers from a Wearable Gesture Sensing Device") discloses an eating monitor with gesture recognition. U.S. patent application No. 20190244704 (Kim et al., Aug. 8, 2019, "Dietary Habit Management Apparatus and Method") discloses a dietary habit management apparatus using biometric measurements.

U.S. patent applications 20190244541 (Hadad et al., Aug. 8, 2019, "Systems and Methods for Generating Personalized Nutritional Recommendations"), 20140255882 (Hadad et al., Sep. 11, 2014, "Interactive Engine to Provide Personal Recommendations for Nutrition, to Help the General Public to Live a Balanced Healthier Lifestyle"), and 20190290172 (Hadad et al., Sep. 26, 2019, "Systems and Methods for Food Analysis, Personalized Recommendations, and Health Management") disclose methods to provide nutrition recommendations based on a person's preferences, habits, medical and activity. U.S. patent application No. 20190246977 (Miller et al., Aug. 15, 2019, "Optical Sensor for Wearable Devices") discloses methods, systems, apparatuses, and/or devices which emit light into a body, receive light from a depth below a surface of the body, and determine a physiological condition of the body.

U.S. patent application No. 20190252569 (Jo et al., Aug. 15, 2019, "Near-Infrared Light Sensors Including 2-Dimensional Insulator") discloses a near infrared light sensor with a 2D material semiconductor layer on a substrate. U.S. Pat. No. 10,401,800 (Cardinali et al., Sep. 3, 2019, "Indicators for Wearable Electronic Devices") discloses a wearable device with a biometric sensor and illuminated biometric status indicator. U.S. Pat. No. 10,423,045 (Roberts et al., Sep. 24, 2019, "Electro-Optical Diffractive Waveplate Beam Shaping System") discloses optical beam shaping systems with a diffractive waveplate diffuser. U.S. Pat. No. 10,444,834 (Vescovi, Oct. 15, 2019, "Devices, Methods, and User Interfaces for a Wearable Electronic Ring Computing Device") discloses an electronic device with a finger-ring-mounted touchscreen.

U.S. patent application No. 20190333634 (Vleugels et al., Oct. 31, 2019, "Method and Apparatus for Tracking of Food Intake and Other Behaviors and Providing Relevant Feedback"), 20170220772 (Vleugels et al., Aug. 3, 2017, "Method and Apparatus for Tracking of Food Intake and Other Behaviors and Providing Relevant Feedback"), and 20180300458 (Vleugels et al., Oct. 18, 2018, "Method and Apparatus for Tracking of Food Intake and Other Behaviors and Providing Relevant Feedback"), as well as U.S. Pat. No. 10,102,342 (Vleugels et al., Oct. 16, 2018, "Method and Apparatus for Tracking of Food Intake and Other Behaviors and Providing Relevant Feedback") and U.S. Pat. No. 10,373,716 (Vleugels et al., Aug. 6, 2019, "Method and Apparatus for Tracking of Food Intake and Other Behaviors and Providing Relevant Feedback"), disclose a method for detecting, identifying, analyzing, quantifying, tracking, processing and/or influencing food consumption.

U.S. Pat. No. 10,496,131 (von Badinski et al., Dec. 3, 2019, "Wearing Computing Device") discloses a charger for an wearable ring. U.S. patent application No. 20190384354 (von Badinski et al., Dec. 19, 2019, "Wearable Computing Device") discloses a wearable smart ring which unlocks a person's computing device. U.S. patent application No. 20200089272 (von Badinski et al., Mar. 19, 2020, "Wearable Computing Device") and U.S. Pat. No. 10,901,460 (von Badinski et al., Jan. 26, 2021, "Wearable Computing Device") disclose a wearable smart ring which identifies an authorized user by scanning the person's blood vessels. U.S. Pat. No. 10,739,820 (Wang et al., Aug. 11, 2020, "Expandable Ring Device") discloses a ring device including force sensors, ultrasonic sensors, inertial measurement units, optical sensors, touch sensors, and other components. U.S. Pat. No. 10,768,666 (von Badinski et al., Sep. 8, 2020, "Wearable Computing Device") discloses a smart ring which unlocks a client computing device, wherein the ring includes an accelerometer, a gyroscope, and/or other motion sensor.

U.S. patent application No. 20200294645 (Vleugels, Sep. 17, 2020, "Gesture-Based Detection of a Physical Behavior Event Based on Gesture Sensor Data and Supplemental Information from at Least One External Source") discloses an automated medication dispensing system which recognizes gestures. U.S. Pat. No. 10,790,054 (Vleugels et al., Sep. 29, 2020, "Method and Apparatus for Tracking of Food Intake and Other Behaviors and Providing Relevant Feedback") discloses a computer-based method of detecting gestures. U.S. Pat. No. 10,842,429 (Kinnunen et al., Nov. 24, 2020, "Method and System for Assessing a Readiness Score of a User") discloses a method and a system for assessing the readiness of a user based on their movements.

U.S. patent applications 20200381101 (Vleugels, Dec. 3, 2020, "Method and Apparatus for Tracking of Food Intake and Other Behaviors and Providing Relevant Feedback") and 20210350920 (Vleugels et al., Nov. 11, 2021, "Method and Apparatus for Tracking of Food Intake and Other Behaviors and Providing Relevant Feedback") disclose methods for detecting, identifying, analyzing, quantifying, tracking, processing and/or influencing the intake of food, eating habits, eating patterns, and/or triggers for food intake events, eating habits, or eating patterns. U.S. patent application No. 20200401183 (von Badinski et al., Dec. 24, 2020, "Wearable Computing Device"), U.S. Pat. No. 11,188,124 (von Badinski et al., Nov. 30, 2021, "Wearable Computing Device"), and U.S. patent application No. 20220057832 (von Badinski et al., Feb. 24, 2022, "Wearable Computing Device") disclose a smart ring with a curved housing having a U-shape interior, a motion sensor, a memory, a transceiver, a temperature sensor, and a processor.

U.S. Pat. No. 10,884,455 (von Badinski et al., Jan. 5, 2021, "Wearable Device and Data Transmission Method") discloses wearable computing device which activates a transceiver based on (EKG) sensor data. U.S. patent application No. 20210072833 (Mutlu et al., Mar. 11, 2021, "Self-Mixing Interferometry-Based Gesture Input System Including a Wearable or Handheld Device") discloses a device with one or more SMI sensors which emit beams of electromagnetic radiation, wherein each beam is emitted in a different direction. U.S. Pat. No. 10,952,670 (Mori et al., Mar. 23, 2021, "Meal Detection Method, Meal Detection System, and Storage Medium") discloses meal detection by analyzing arm motion data and heart rate data. U.S. patent application No. 20210089126 (Nickerson, Mar. 25, 2021, "Smart Ring") discloses a smart ring with a capacitive touch sensor.

U.S. patent application No. 20210204815 (Koskela et al., Jul. 8, 2021, "An Optical Sensor System of a Wearable Device, A Method for Controlling Operation of an Optical Sensor System and Corresponding Computer Program Product") discloses a wearable optical sensor system including at least two photo transmitters, a photoreceiver, receiving electronics, and a microcontroller. U.S. patent application No. 20210289897 (Hsu et al., Sep. 23, 2021, "Smart Ring") discloses a smart ring with an antenna chip and a metal ring which functions as an antenna. U.S. patent application No. 20210307686 (Catani et al., Oct. 7, 2021, "Methods and Systems to Detect Eating") discloses methods and systems for automated eating detection comprising a continuous glucose monitor (CGM) and an accelerometer. U.S. Pat. No. 11,188,160 (Liu, Nov. 30, 2021, "Wireless Controlling System Implemented with Smart Ring and Wireless Controlling Method Thereof") a wireless controlling system including a smart ring and an identification program installed in a mobile device.

U.S. patent application No. 20220012467 (Kuo et al., Jan. 13, 2022, "Multi-Sensor Analysis of Food") discloses a method for estimating food composition by 3D imaging and millimeter-wave radar. U.S. Pat. No. 11,275,453 (Tham et al., Mar. 15, 2022, "Smart Ring for Manipulating Virtual Objects Displayed By a Wearable Device") discloses systems, devices, media, and methods for using a ring to manipulate a virtual object displayed by smart eyewear. U.S. patent applications 20220085841 (Gretarsson et al., Mar. 17, 2022, "Smart Ring") and 20220407550 (Gretarsson et al., Dec. 22, 2022, "Smart Ring") disclose a wearable device which detects inputs, gestures, and/or biometric parameters. U.S. patent application No. 20220091683 (Beyhs et al., Mar. 24, 2022, "Ring Input Device with Pressure-Sensitive Input") and U.S. Pat. No. 11,733,790 (Beyhs et al., Aug. 22, 2023, "Ring Input Device with Pressure-Sensitive Input") disclose a ring with a pressure-sensitive input mechanism.

U.S. patent application No. 20220296117 (Laakkonen et al., Sep. 22, 2022, "Apparatus and Method for Measuring Photoplethysmogram") and U.S. Pat. No. 11,291,378 (Laakkonen et al., Apr. 5, 2022, "Apparatus and Method for Measuring Photoplethysmogram") and U.S. Pat. No. 12,042,258 (Laakkonen et al., Jul. 23, 2024, "Apparatus and Method for Measuring Photoplethysmogram") disclose a wearable smart for photoplethysmogram measurement. U.S. patent applications 20220334639 (Sanchez, Oct. 20, 2022, "Projection System for Smart Ring Visual Output") and U.S. patent application 20220383741 (Sanchez, Dec. 1, 2022, "Non-Visual Outputs for a Smart Ring"), and U.S. Pat. No. 11,462,107 (Sanchez, Oct. 4, 2022, "Light Emitting Diodes and Diode Arrays for Smart Ring Visual Output"), disclose a smart ring system for displaying information concerning driving conditions. U.S. Pat. No. 11,479,258 (Sanchez, Oct. 25, 2022, "Smart Ring System for Monitoring UVB Exposure Levels and Using Machine Learning Technique to Predict High Risk Driving Behavior") discloses systems and methods determine a driver's fitness to safely operate a moving vehicle based on UVB exposure.

U.S. patent application No. 20220386885 (Lee et al., Dec. 8, 2022, "Wearable Electronic Device Measuring Blood Pressure and Method for Operating The Same") discloses a wearable electronic device with a memory, a first sensor, a second sensor, and a processor. U.S. patent application 20220409072 (Kang et al., Dec. 29, 2022, "Apparatus and Method for Estimating Bio-Information") discloses an apparatus to estimate biometric parameters using a pulse wave sensor with channels in an isotropic shape. U.S. Pat. No. 11,540,599 (Yokoyama et al., Jan. 3, 2023, "Watch Band with Adjustable Fit") discloses shape-memory tensioning elements which respond to a stimulus in order to adjust the fit of a watch band. U.S. patent application No. 20230000405 (Lee et al., Jan. 5, 2023, "Apparatus and Method for Estimating Bio-Information Based on Bio-Impedance") discloses an apparatus to estimate biometric parameters using an impedance sensor, including a pair of input electrodes and a pair of receiving electrodes.

U.S. patent application No. 20230007884 (Kang et al., Jan. 12, 2023, "Apparatus and Method for Estimating Bio-Information") discloses an apparatus to estimate biometric parameters which measures pulse wave signals from an object. U.S. patent application No. 20230008487 (Caizzone et al., Jan. 12, 2023, "System and Method for Smart Rings Employing Sensor Spatial Diversity") discloses a ring for photoplethysmographic sensing which uses sensor spatial diversity to enhance the quality and the reliability of measurements. U.S. patent application No. 20230021838 (Tse et al., Jan. 26, 2023, "Wearable Electronic Device") discloses a wearable electronic device with conductive areas on both inner and outer surfaces. U.S. patent application No. 20230034807 (McDaniel et al., Feb. 2, 2023, "Systems and Methods Including a Device for Personalized Activity Monitoring Involving the Hands") discloses a wearable device for activity monitoring involving the use of hands.

U.S. patent application No. 20230043018 (Wai et al., Feb. 9, 2023, "Smart Ring for Use with a User Device and Wi-Fi Network") discloses a smart ring with a battery, a memory, processing circuitry, a plurality of sensors, and a plurality of antennas. U.S. Pat. No. 11,580,300 (Tham et al., Feb. 14, 2023, "Ring Motion Capture and Message Composition System") discloses systems, devices, media, and methods for composing and sharing a message based on the motion of a ring. U.S. patent application No. 20230053252 (Jung, Feb. 16, 2023, "Electronic Device Adjusting Oxygen Saturation and Method for Controlling the Same") discloses a device with a first sensor which detects movement and a second sensor which measures oxygen saturation.

U.S. patent applications 20230056434 (Jang et al., Feb. 23, 2023, "Apparatus and Method for Estimating Blood Pressure") and 20230070636 (Kang et al., Mar. 9, 2023, "Apparatus and Method for Estimating Blood Pressure") disclose an apparatus for estimating blood pressure using a pulse wave sensor. U.S. Pat. No. 11,599,147 (von Badinski et al., Mar. 7, 2023, "Wearable Computing Device") discloses a smart ring with a curved housing having a U-shape interior, a semi-flexible PCB, a motion sensor, a memory, a transceiver, a temperature sensor, and a processor. U.S. patent application No. 20230072436 (Sanchez, Mar. 9, 2023, "Harvesting Energy for a Smart Ring Via Piezoelectric Charging") discloses a smart ring which harvests mechanical energy using piezoelectricity. U.S. patent application No. 20230085555 (Nomvar et al., Mar. 16, 2023, "A Non-Invasive Continuous Blood Glucose Monitor") discloses a non-invasive device for measuring glucose levels.

U.S. patent applications 20230079736 (Makinen, Mar. 16, 2023, "Wearing Detection Techniques for Wearable Devices") and 20230081794 (Makinen et al., Mar. 16, 2023, "Wearing Detection Techniques for Wearable Devices") disclose a method of directing light from a light source to a light detector using an optical light guide of an wearable device. U.S. patent application 20230113714 (Vallius et al., Apr. 13, 2023, "Configurable Photoplethysmogram System"), U.S. Pat. No. 12,074,637 (Vallius et al., Aug. 27, 2024, "Configurable Photoplethysmogram System"), and U.S. patent application No. 20240364420 (Vallius et al., Oct. 31, 2024, "Configurable Photoplethysmogram System") disclose a wearable electronic device with optical sensors (including transmitter sensors and/or receiver sensors) and protrusions on an inner surface of the wearable electronic device. U.S. patent application No. 20230118067 (Chang et al., Apr. 20, 2023, "Electronic Device and Method to Measure Bioelectrical Impedance") discloses an electronic device with a plurality of electrodes, a sensor connected to the electrodes, a memory, and a processor which obtains contact impedances through the sensor.

U.S. patent applications 20230143293 (Sanchez, May 11, 2023, "Biometric Authentication Using a Smart Ring") and U.S. patent application No. 20230153416 (Sanchez, May 18, 2023, "Proximity Authentication Using a Smart Ring") discloses systems and methods for performing biometric authentication using a smart ring. U.S. patent application No. 20230157645 (Lee et al., May 25, 2023, "Apparatus and Method for Estimating Bio-Information") discloses an apparatus to estimate biometric parameters using a spectrometer. U.S. Pat. No. 11,660,228 (Goff et al., May 30, 2023, "Positional Obstructive Sleep Apnea Detection System") discloses an obstructive sleep apnea detection device which uses an optical engagement surface adapted to engage a user's skin. U.S. Pat. No. 11,666,230 (Piccinini et al., Jun. 6, 2023, "Electronic Device and Method for Noninvasive, Continuous Blood Pressure Monitoring") discloses an electronic device and method for continuous noninvasive blood pressure monitoring.

U.S. patent application No. 20230174114 (Sanchez, Jun. 8, 2023, "Smart Ring System for Measuring Stress Levels and Using Machine Learning Techniques to Predict High Risk Driving Behavior") discloses systems and methods determine a driver's fitness to safely operate a moving vehicle based on their stress level. U.S. patent application No. 20230178213 (Haertel et al., Jun. 8, 2023, "Automatic Tracking of Probable Consumed Food Items") discloses a method for detecting information associated with consumed food. U.S. patent application No. 20230190118 (Park et al., Jun. 22, 2023, "Apparatus and Method for Estimating Blood Pressure") discloses an apparatus for estimating blood pressure which extracts a cardiac output feature, a first candidate total peripheral resistance feature, and a second candidate peripheral resistance feature. U.S. patent application 20230190197 (Huttunen, Jun. 22, 2023, "Adjustable Sensor in Wearable Device") discloses a wearable device with an adjustment mechanism which moves a sensor component.

U.S. patent application No. 20230190201 (Singleton et al., Jun. 22, 2023, "Techniques for Multiple Wearable Devices") discloses a method of receiving first physiological data from a first wearable device worn at a first position on the user and second physiological data from a second wearable device worn at a second position on the user. U.S. patent application No. 20230200744 (Choi et al., Jun. 29, 2023, "Apparatus and Method for Estimating Target Component") discloses an apparatus for estimating a target component via a spectrometer. U.S. patent application No. 20230205170 (Sanchez, Jun. 29, 2023, "Soft Smart Ring and Method of Manufacture") discloses a smart ring with a body made from flexible material, a first part, a second part removably connected to the first part, and at least one pair of break-away portions disposed within the body.

U.S. patent application No. 20230205325 (Khan, Jun. 29, 2023, "Wearable Apparatus and Control Method Thereof") discloses a wearable apparatus with a display, a strap, at least one sensor configured to acquire posture information, and at least one processor. U.S. patent application 20230213970 (von Badinski et al., Jul. 6, 2023, "Wearable Computing Device") discloses a smart ring with a body having an inner surface and an outer surface, wherein a cavity is formed on the inner surface of the body part and an electronic part is arranged in the cavity. U.S. patent application 20230218192 (Eom et al., Jul. 13, 2023, "Wrist-Type Body Component Measuring Apparatus and Body Component Measuring Method Using the Same") discloses a wrist-worn band with: a first input electrode and a first output electrode disposed on an inside surface of the band; and a second input electrode and a second output electrode disposed on an outside surface of the band.

U.S. patent application No. 20230225671 (Kosman et al., Jul. 20, 2023, "Wearable Health Apparatus for the Collection of Wellness Data and Providing Feedback Therefrom to the Wearer") discloses a ring with replaceable outer shells, as well as hardware and software that allow the user to communicate with a cell phone, cloud provider, table, personal computer or AI assistant. U.S. patent application No. 20230225676 (Halpern et al., Jul. 20, 2023, "Wearable Devices") discloses an wearable annular member with deformable features. U.S. patent application No. 20230233084 (Moon et al., Jul. 27, 2023, "Method and Apparatus for Correcting Error of Optical Sensor, and Apparatus for Estimating Biometric Information") discloses a method of correcting an optical sensor error by adjusting the brightness of a light source. U.S. patent application No. 20230297858 (Vleugels et al., Sep. 21, 2023, "Nutritional Content Determination Based on Gesture Detection Data") discloses techniques for nutritional content determination based on gestures.

U.S. patent application No. 20230301540 (Jung et al., Sep. 28, 2023, "Apparatus and Method of Measuring Bio Signal") discloses a method of measuring a biosignal by positioning electrodes and switching an impedance measurer. U.S. patent applications 20230309844 (Jang et al., Oct. 5, 2023, "Apparatus and Method for Estimating Blood Pressure") and 20240172945 (Park et al., May 30, 2024, "Apparatus and Method for Estimating Blood Pressure") disclose an apparatus and method for estimating blood pressure using a photoplethysmogram (PPG) sensor. U.S. patent application 20230324293 (Lee, Oct. 12, 2023, "Apparatus and Method for Estimating Body Water Status") discloses an apparatus for estimating body hydration level with a near-infrared light spectrometer. U.S. patent application No. 20230350492 (Nickerson, Nov. 2, 2023, "Smart Ring") discloses a smart ring worn which is controlled based on its position.

U.S. patent application No. 20230350503 (D'Amone et al., Nov. 2, 2023, "Ring Input Devices") and U.S. Pat. No. 11,714,494 (D'Amone et al., Aug. 1, 2023, "Ring Input Devices") disclose how a head-mountable device can be operated with a ring input device worn on a finger of a user. U.S. patent application No. 20230359291 (Beyhs et al., Nov. 9, 2023, "Ring Input Device with Variable Rotational Resistance") discloses a ring input device with variable rotational resistance mechanisms which change the rotational friction of a rotating outer band. U.S. patent application No. 20230361588 (Sanchez, Nov. 9, 2023, "Smart Ring Power and Charging") discloses a smart ring with a both a removable power source and an internal power source. U.S. patent application No. 20230376071 (von Badinski et al., Nov. 23, 2023, "Wearable Computing Device") discloses a smart ring comprising an external housing component with an outer circumferential surface and an inner circumferential surface, wherein a portion of the inner circumferential surface contacts a person's finger.

U.S. patent applications 20230376072 (von Badinski et al., Nov. 23, 2023, "Wearable Computing Device") and 20230384827 (von Badinski et al., Nov. 30, 2023, "Wearable Computing Device") disclose a smart ring with a curved housing having a U-shape interior, a curved battery, a semi-flexible PCB, a motion sensor, a memory, a transceiver, a temperature sensor, and a processor. U.S. Pat. No. 11,829,831 (Ershov et al., Nov. 28, 2023, "Electronic System with Ring Device") discloses a wearable electronic device with a coil which is formed from metal traces. U.S. patent application 20230380692 (Huttunen et al., Nov. 30, 2023, "Optimized Structures for Optical Measurement") discloses a wearable device with components which block stray light from an optical sensing path.

U.S. patent application No. 20230409080 (von Badinski et al., Dec. 21, 2023, "Wearable Computing Device") discloses a smart ring with a curved housing with a substantially transparent portion, a curved battery, a semi-flexible PCB, a motion sensor, a memory, a transceiver, a temperature sensor, and a processor. U.S. Pat. No. 11,850,069 (Mars et al., Dec. 26, 2023, "Wearable Device and Methods of Manufacturing") discloses a smart ring with a battery, a PCB, a fingerprint sensor, a temperature sensor, a memory, and a processing unit. U.S. Pat. No. 11,862,037 (Seymore et al., Jan. 2, 2024, "Methods and Devices for Detection of Eating Behavior") discloses systems, devices, and methods using audio data to detect and correct eating behavior. U.S. patent application 20240000328 (Kangas et al., Jan. 4, 2024, "Asymmetric Sensors for Ring Wearable") discloses a wearable device with a first light-emitting component at a first radial position and a second light-emitting component at a second radial position.

U.S. patent application No. 20240000380 (Fei et al., Jan. 4, 2024, "Wearable Device") discloses an annular case with an energy storage unit, an information transmission unit, and an optical identification assembly. U.S. patent application No. 20240000387 (Realubit et al., Jan. 4, 2024, "Finger Wearable Health Monitoring Device") discloses a finger-worn health monitoring device comprising a circular metal shell. U.S. Pat. No. 11,864,871 (Kang et al., Jan. 9, 2024, "Wearable Device and Method of Measuring Bio-Signal") discloses an external light collector, an auxiliary light source, and a light receiver. U.S. Pat. No. 11,868,178 (von Badinski et al., Jan. 9, 2024, "Wearable Computing Device") discloses a smart ring with a curved housing having a U-shape interior, a battery, a semi-flexible PCB, a motion sensor, a memory, a transceiver, a temperature sensor, and a processor.

U.S. Pat. No. 11,868,179 (von Badinski et al., Jan. 9, 2024, "Wearable Computing Device") discloses a smart ring with a curved housing having a U-shape interior, a battery, a semi-flexible PCB, a motion sensor, a memory, a transceiver, a temperature sensor, a processor, an infrared light emitter, and a visible light emitter. U.S. patent application No. 20240012479 (Qiu et al., Jan. 11, 2024, "Ring Enabling Its Wearer to Enter Control Commands") discloses systems and methods, including a smart ring, which enable a user to control electronic devices in a local network. U.S. Pat. No. 11,874,701 (von Badinski et al., Jan. 16, 2024, "Wearable Computing Device") discloses a smart ring with a curved housing having a U-shape interior, a battery, a semi-flexible PCB, a motion sensor, a memory, a transceiver, a temperature sensor, and a processor which identifies gestures based on data from the motion sensor. U.S. Pat. No. 11,874,702 (von Badinski et al., Jan. 16, 2024, "Wearable Computing Device") discloses a smart ring with a curved housing with a substantially transparent portion, a battery, a semi-flexible PCB, a motion sensor, a memory, a transceiver, a temperature sensor, and a processor.

U.S. Pat. No. 11,895,383 (Prushinskiy et al., Feb. 6, 2024, "Electronic Device Including Optical Sensor") discloses an electronic device with a housing which is rotatably arranged and an optical sensor assembly. U.S. patent application No. 20240045473 (Lee et al., Feb. 8, 2024, "Electronic Device and Method for Operating Electronic Device") discloses an electronic device with movable housings, at least one sensor, and one or more electromagnets. U.S. patent application 20240046505 (Liu et al., Feb. 8, 2024, "Electronic Device and Method with Pose Prediction") discloses an electronic device for predicting a pose and a method for operating the electronic device. U.S. patent application No. 20240048675 (Choi et al., Feb. 8, 2024, "Electronic Device and Operation Method Thereof") discloses a device with processors which obtain a rotation angle of the device and determine whether the rotation angle is greater than or equal to a reference rotation angle.

U.S. Pat. No. 11,902,791 (Mars et al., Feb. 13, 2024, "Reader Device with Sensor Streaming Data and Methods") discloses an access control system with a controller having an antenna interface to broadcast identifying data. U.S. patent application No. 20240058686 (Bhandarkar et al., Feb. 22, 2024, "Smart Wearable Device") discloses a smart ring with an electronics unit that is selectively attachable to a coupling mount. U.S. Pat. No. 11,911,181 (Huttunen et al., Feb. 27, 2024, "Flexible Wearable Ring Device") discloses a wearable device made from flexible materials. U.S. Pat. No. 11,916,900 (Mars et al., Feb. 27, 2024, "Authorized Remote Control Device Gesture Control Methods and Apparatus") discloses a method for controlling a remote control device which includes capturing biometric data.

U.S. patent application No. 20240065631 (Brooks, Feb. 29, 2024, "Pressure Adjustment for Biometric Measurement") discloses a user device with a pressure sensor to determine whether the pressure between a user's body and the device is within a proper range. U.S. Pat. No. 11,925,441 (Rantanen et al., Mar. 12, 2024, "Techniques for Determining Blood Pressure Based on Morphological Features of Pulses Preliminary Class") discloses a wearable device with one or more light emitting components, one or more photodetectors, and a controller that couples the light emitting components to the photodetectors. U.S. patent application No. 20240081663 (Park et al., Mar. 14, 2024, "Apparatus for Estimating Bio-Information and Method of Detecting Abnormal Bio-Signal") discloses an apparatus with a photoplethysmogram (PPG) sensor. U.S. Pat. No. 11,937,905 (Singleton et al., Mar. 26, 2024, "Techniques for Leveraging Data Collected by Wearable Devices and Additional Devices") discloses a method comprising receiving physiological data from a wearable device and environmental data from an external device.

U.S. Pat. No. 11,949,673 (Sanchez, Apr. 2, 2024, "Gesture Authentication Using a Smart Ring") discloses systems and methods for multi-factor authentication using a smart ring. U.S. patent application No. 20240112563 (Norman et al., Apr. 4, 2024, "Bluetooth Enabled Smart Ring") discloses a smart ring device with wireless communication with a computing device that transitions between one or more states based on user and/or device inputs. U.S. patent application No. 20240115212 (Jang et al., Apr. 11, 2024, "Apparatus and Method for Estimating Physiological Variables") discloses an apparatus for estimating physiological variables using sensors and a neural-network-based physiological variable estimation model. U.S. patent application No. 20240122548 (Kangas et al., Apr. 18, 2024, "Techniques for Adaptive Sensors of a Wearable Device") discloses selecting one or more optical channels in a wearable device based on a comparison of measurement quality and power consumption metrics.

U.S. patent application No. 20240122550 (Syrjala et al., Apr. 18, 2024, "Techniques for Optimal Parameter Tuning for a Wearable Device") discloses comparing measurement quality metrics, respective power consumption metrics, or both, and selecting a measurement profile to be used to acquire additional physiological data. U.S. patent application No. 20240125915 (Au et al., Apr. 18, 2024, "Method, Apparatus, and System for Wireless Sensing Measurement and Reporting") and U.S. patent application No. 20240179550 (Au et al., May 30, 2024, "Method, Apparatus, and System for Wireless Sensing Measurement and Reporting") disclose methods, devices, and systems for wireless sensing including transmitting a time series of at least one wireless sounding signal (WSS).

U.S. patent application No. 20240126328 (von Badinski et al., Apr. 18, 2024, "Wearable Computing Device") discloses a smart ring with a curved housing having a U-shape interior, a battery, a semi-flexible PCB, a galvanic sensor, light emitters, light receivers, a memory, a transceiver, a temperature sensor, and a processor. U.S. patent application No. 20240126329 (von Badinski et al., Apr. 18, 2024, "Wearable Computing Device") discloses a wearable ring device with a ring-shaped housing, a printed circuit board, and a sensor module with infrared light emitters, visible light emitters, and light receivers. U.S. patent application No. 20240126330 (von Badinski et al., Apr. 18, 2024, "Wearable Computing Device") discloses a wearable ring device with a ring-shaped housing comprising two metallic materials, a printed circuit board, light emitters, and light receivers.

U.S. patent application No. 20240126382 (Yoo, Apr. 18, 2024, "Wearable Device and Method for Controlling Same") discloses a method of controlling a smart ring by sensing contact from a finger on an outer surface electrode on an outer circumference of the ring. U.S. patent application 20240134417 (von Badinski et al., Apr. 25, 2024, "Wearable Computing Device") discloses a wearable ring device with a ring-shaped housing, a thermoelectric generator, a printed circuit board, light emitters, and light receivers. U.S. patent application No. 20240138721 (Eom et al., May 2, 2024, "Apparatus and Method for Estimating Concentration of Analyte Component") discloses an apparatus for estimating a component level using a plurality of light sources with different central wavelengths and at least one light detector. U.S. patent application No. 20240143027 (von Badinski et al., May 2, 2024, "Wearable Computing Device") discloses a wearable ring device with a ring-shaped housing with one or more windows, a printed circuit board, light emitters, and light receivers.

U.S. patent application No. 20240143028 (von Badinski et al., May 2, 2024, "Wearable Computing Device") discloses a wearable ring device with a ring-shaped housing, a printed circuit board, and a sensor module that includes red light emitters, infrared light emitters, and light receivers. U.S. patent application No. 20240146350 (Gretarsson et al., May 2, 2024, "Smart Ring") discloses a ring, band, or necklace with a pressure-sensitive mechanism that receives user input in the form of applied pressure. U.S. Pat. No. 11,980,439 (Koskela et al., May 14, 2024, "Optical Sensor System of a Wearable Device, A Method for Controlling Operation of an Optical Sensor System and Corresponding Computer Program Product") discloses a system comprising at least two photo transmitters, a photoreceiver, receiving electronics, and a microcontroller. U.S. patent application No. 20240168521 (von Badinski et al., May 23, 2024, "Wearable Computing Device") discloses a wearable ring device with a ring-shaped housing, one or more temperature sensors, a printed circuit board, light emitters, and light receivers.

U.S. patent application No. 20240176425 (Wang et al., May 30, 2024, "Method for Controlling Wearable Device and Wearable Device") discloses detecting an abnormal touch event on a display screen of a wearable device and enabling gesture recognition in response to the abnormal touch event. U.S. Pat. No. 12,007,727 (Leith et al., Jun. 11, 2024, "Watch Band with Fit Detection") discloses a watch band with an adjustable capacitor whose capacitance changes when the watch band configuration changes. U.S. patent application No. 20240188834 (Kwon et al., Jun. 13, 2024, "Apparatus and Method for Measuring Blood Pressure") discloses an apparatus for estimating blood pressure using a pulse wave sensor. U.S. patent application No. 20240188881 (Bonificio et al., Jun. 13, 2024, "Wearable Ring Device and Method of Monitoring Sleep Apnea Events") discloses a finger-worn band with a pulse oximetry sensor on an inner surface of the band.

U.S. Pat. No. 12,013,725 (von Badinski et al., Jun. 18, 2024, "Wearable Computing Device") discloses a wearable ring device with a ring-shaped housing, a printed circuit board, a haptic feedback module, red light emitters, infrared light emitters, and light receivers. U.S. patent application No. 20240201736 (von Badinski et al., Jun. 20, 2024, "Wearable Computing Device") discloses a wearable ring device with a ring-shaped housing, a first conductive contact component, a second conductive contact component, a printed circuit board, light emitters, and light receivers. U.S. patent application No. 20240237904 (Makinen et al., Jul. 18, 2024, "Techniques for Measurement Path Multiplexing for a Wearable Device") discloses methods, systems, and devices for measurement multiplexing for a wearable device including selecting a transmission angle from a set of transmission angles and a reception angle from a set of reception angles based on signal quality comparison.

U.S. patent application No. 20240241541 (Makinen, Jul. 18, 2024, "Optical Components and Assembly Techniques") discloses a manufacturing system for assembling optical components onto an inner circumference of a wearable ring. U.S. Pat. No. 12,076,142 (Venugopal et al., Sep. 3, 2024, "Physiological Monitoring System for Measuring Oxygen Saturation") discloses a wearable device with a housing having a plurality of windows through which light emitters emit light and through which light detectors receive light. U.S. patent application No. 20240293084 (Huttunen et al., Sep. 5, 2024, "Flexible Wearable Ring Device") discloses a flexible wearable device that is elastically deformable. U.S. patent application No. 20240298966 (Ariza-Zambrano et al., Sep. 12, 2024, "Method and System for Detecting Food Intake Events from Wearable Devices and Non-Transitory Computer-Readable Storage Medium") discloses a system and method for detecting food intake using wearable devices.

SUMMARY OF THE INVENTION

Disclosed herein is a wearable device (e.g. finger ring or smart watch) with optical sensors for measuring biometric parameter levels. Biometric parameters can include oxygenation level, hydration level, glucose level, heart rate, heart rate variability, and/or blood pressure. Optical sensors on the device include light emitters and light receivers. Light from the light emitters is transmitted through and/or reflected by body tissue and then received by the light receivers. Changes in the light due to its interaction with body tissue are analyzed to measure biometric parameters.

In an example, the angles and/or vectors along which light from light emitters is transmitted through a person's body tissue can be automatically changed by the device in order to scan different tissue regions and/or different tissue depths. In an example, the device can include body-facing protrusions. The light emitters and/or the light receivers can be located on portions of the device which have these protrusions.

BRIEF INTRODUCTION TO THE FIGURES

FIGS. 1 and 2 show two sequential cross-sectional views of a wearable biometric device (e.g. finger ring or smart watch) wherein the angle and/or vector of light from a light emitter is automatically changed by the device to scan different tissue regions and/or depths.

FIG. 3 shows a cross-sectional view of a wearable biometric device (e.g. finger ring or smart watch) with body-facing protrusions, wherein sets of light emitters and light receivers are located on portions of the device which have protrusions.

FIG. 4 shows a cross-sectional view of a wearable biometric device (e.g. finger ring or smart watch) with body-facing protrusions, wherein individual light emitters and light receivers are located on portions of the device which have protrusions.

FIG. 5 shows a cross-sectional view of a wearable biometric device (e.g. finger ring or smart watch) with optical sets, wherein each optical set includes a light emitter, a light receiver, and an intermittently-moving mirror or lens.

FIG. 6 shows a cross-sectional view of a wearable biometric device (e.g. finger ring or smart watch) with optical sets, wherein each optical set includes a light emitter, a light receiver, and an oscillating mirror or lens.

DETAILED DESCRIPTION OF THE FIGURES

Figures 1, 2:
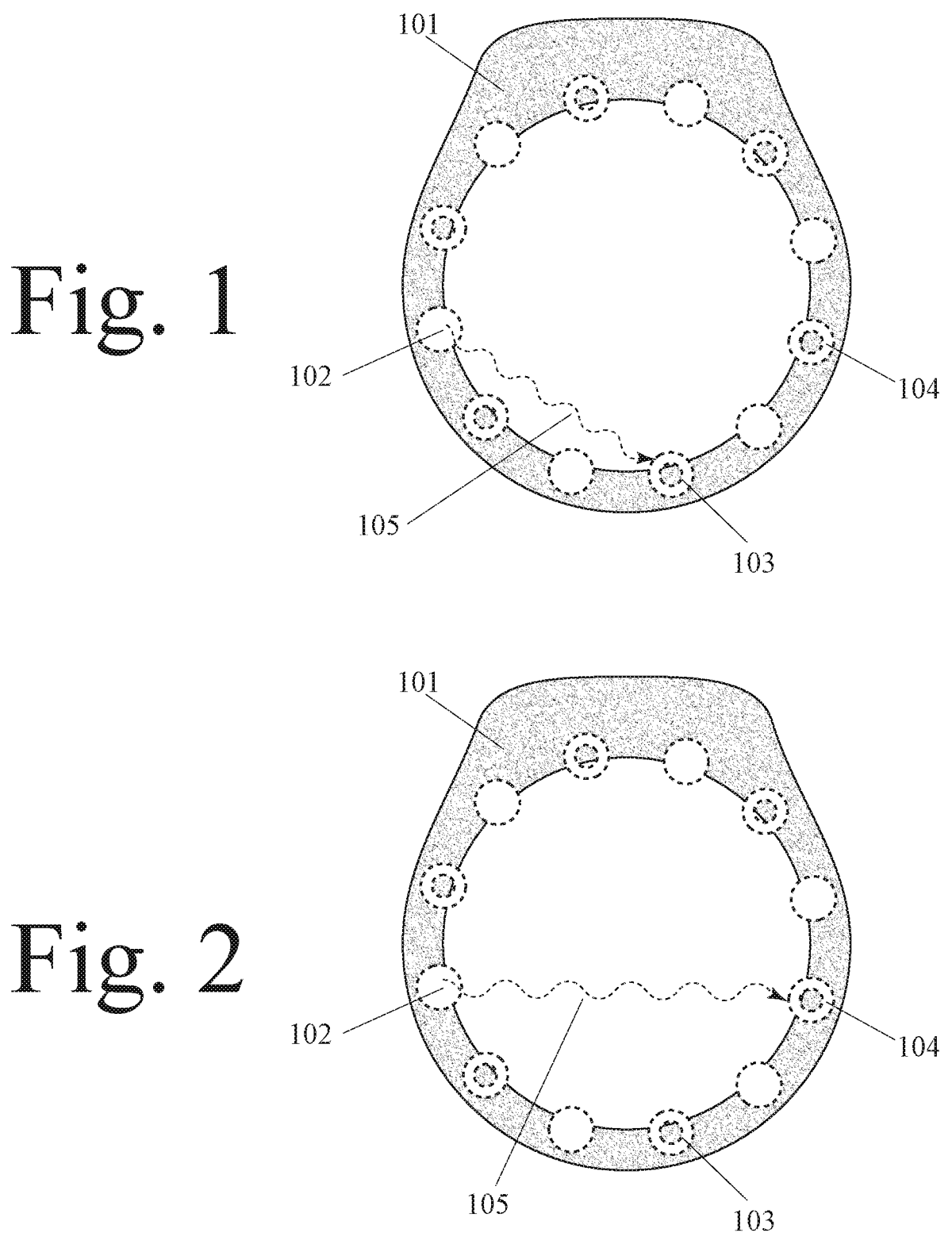

Before discussing the specific embodiments of this invention which are shown in FIGS. 1 through 4, this disclosure provides an introductory section which covers some of the general concepts, components, and methods which comprise this invention. Where relevant, these concepts, components, and methods can be applied as variations to the examples shown in FIGS. 1 through 4 which are discussed afterwards.

In an example, a wearable biometric device can comprise: a ring which is worn on a person's finger; and an array of light emitters and light receivers on the ring. In an example, light energy from the light emitters which has passed through or been reflected by body tissue and has been received by the light receivers can be analyzed in order to measure one or more biometric parameters. In an example, the one or more biometric parameters can be selected from the group consisting of: oxygenation level, hydration level, glucose level, pulse rate, heart rate variability, and blood pressure. In an example, the array of light emitters and light receivers can span at least half of the circumference of the person's finger.

In an example, an angle or vector of light emitted from a light emitter can be automatically changed over time by the device. In an example, a light emitter can emit a beam of light at a first angle or vector at a first time and emit a beam of light at a second angle or vector at a second time. In an example, a beam of light can be passed through or reflected by different regions or depths of body tissue by changing an angle or vector along which the beam of light is emitted. In an example, angles or vectors along which a light emitter emits beams of light can be iteratively varied to scan different regions or depths of body tissue. In an example, angles or vectors along which a light emitter emits beams of light can be automatically oscillated to scan different regions or depths of body tissue.

In an example, an angle or vector of light emitted from a light emitter can be automatically changed over time by the device by moving a light guide (e.g. mirror or lens). In an example, a beam of light can be passed through or reflected by different regions or depths of body tissue by changing an angle or vector along which the beam of light is emitted by moving a light guide (e.g. mirror or lens). In an example, angles or vectors along which a light emitter emits beams of light can be iteratively varied to scan different regions or depths of body tissue by moving a light guide (e.g. mirror or lens). In an example, angles or vectors along which a light emitter emits beams of light can be automatically oscillated to scan different regions or depths of body tissue by moving a light guide (e.g. mirror or lens).

In an example, a wearable biometric device can comprise: a ring which is worn on a person's finger; an array of light emitters and light receivers which are worn around the person's finger; wherein the array of light emitters and light receivers collectively span at least half of the circumference of the person's finger; wherein light energy from the light emitters which has passed through the person's body tissue or been reflected from the person's body tissue and has been received by the light receivers is analyzed in order to measure one or more biometric parameters selected from the group consisting of the person's oxygenation level, hydration level, glucose level, pulse rate, heart rate variability, and blood pressure; and wherein angles or vectors along which a light emitter emits beams of light are automatically oscillated to scan different regions or depths of body tissue.

In an example, a wearable biometric device can comprise: a ring, band, or smart watch which is worn on a person's wrist; and an array of light emitters and light receivers on the ring, band, or smart watch. In an example, light energy from the light emitters which has passed through or been reflected by body tissue and has been received by the light receivers can be analyzed in order to measure one or more biometric parameters. In an example, the one or more biometric parameters can be selected from the group consisting of: oxygenation level, hydration level, glucose level, pulse rate, heart rate variability, and blood pressure. In an example, the array of light emitters and light receivers can collectively span at least half of the circumference of the person's wrist.

In an example, an angle or vector of light emitted from a light emitter can be automatically changed over time by the device. In an example, a light emitter can emit a beam of light at a first angle or vector at a first time and emit a beam of light at a second angle or vector at a second time. In an example, a beam of light can be passed through or reflected by different regions or depths of body tissue by changing an angle or vector along which the beam of light is emitted. In an example, angles or vectors along which a light emitter emits beams of light can be iteratively varied to scan different regions or depths of body tissue. In an example, angles or vectors along which a light emitter emits beams of light can be automatically oscillated to scan different regions or depths of body tissue.

In an example, an angle or vector of light emitted from a light emitter can be automatically changed over time by the device by moving a light guide (e.g. mirror or lens). In an example, a beam of light can be passed through or reflected by different regions or depths of body tissue by changing an angle or vector along which the beam of light is emitted by moving a light guide (e.g. mirror or lens). In an example, angles or vectors along which a light emitter emits beams of light can be iteratively varied to scan different regions or depths of body tissue by moving a light guide (e.g. mirror or lens). In an example, angles or vectors along which a light emitter emits beams of light can be automatically oscillated to scan different regions or depths of body tissue by moving a light guide (e.g. mirror or lens).

In an example, a wearable biometric device can comprise: a ring, band, or smart watch which can be configured to be worn on a person's wrist; an array of light emitters and light receivers which can be configured to be worn around the person's wrist; wherein the array of light emitters and light receivers can be configured to collectively span at least half of the circumference of the person's wrist; wherein light energy from the light emitters which has passed through the person's body tissue or been reflected from the person's body tissue and has been received by the light receivers can be analyzed in order to measure one or more biometric parameters selected from the group consisting of the person's oxygenation level, hydration level, glucose level, pulse rate, heart rate variability, and blood pressure; and In an example, angles or vectors along which a light emitter emits beams of light can be automatically oscillated to scan different regions or depths of body tissue.

In an example, a wearable biometric device can comprise: an arcuate ring which can be configured to be worn around a person's finger, wherein the arcuate ring spans at least two-thirds of the circumference of the person's finger and has a plurality of radial undulations; and at least three optical sensor sets which are held in proximity to the person's finger, wherein the optical sensor sets are located on portions of the ring which protrude toward the surface of the person's finger. In an example, the portions of the ring which protrude toward the surface of the person's finger can comprise protrusions on the ring. In an example, the optical sensor sets can be located at the protrusions on the ring. In an example, the optical sensor sets can collectively span at least two-thirds of the circumference of the person's finger.

In an example, an optical sensor set can further comprise a red light emitter. In an example, a red light emitter can be located at a protrusion of the ring. In an example, an optical sensor set can further comprise an infrared light emitter. In an example, an infrared light emitter can be located at a protrusion of the ring. In an example, an optical sensor set can further comprise a green light emitter. In an example, a green light emitter can be located at a protrusion of the ring. In an example, an optical sensor set can further comprise a light receiver. In an example, a light receiver can be located at a protrusion of the ring.

In an example, each optical sensor set can further comprise a red light emitter, an infrared light emitter, a green light emitter, or a light receiver. In an example, each optical sensor set can further comprise an infrared light emitter and a green light emitter. In an example, each optical sensor set can further comprise a red light emitter and a green light emitter. In an example, each optical sensor set can further comprise a red light emitter, an infrared light emitter, and a green light emitter. In an example, each optical sensor set can further comprise a red light emitter, an infrared light emitter, a green light emitter, and a light receiver.

In an example, a wearable biometric device can comprise: an arcuate band, ring, or smart watch which can be configured to be worn around a person's wrist or finger, wherein the arcuate band, ring, or smart watch spans at least two-thirds of the circumference of the person's wrist or finger, wherein the arcuate band, ring, or smart watch has a plurality of radial undulations; and at least three optical sensor sets which can be held in proximity to the person's wrist or finger, wherein the optical sensor sets can be located on portions of the band, ring, or smart watch which protrude toward the surface of the person's wrist or finger, wherein the optical sensor sets collectively span at least two-thirds of the circumference of the person's wrist or finger, and In an example, each optical sensor set can further comprise at least one infrared light emitter or visible red light emitter, at least one green-light emitter, at least one light receiver. In an example, the portions of the band, ring, or smart watch which protrude toward the surface of the person's wrist or finger can comprise protrusions on the band, ring, or smart watch. In an example, the optical sensor sets can be located at the protrusions on the band, ring, or smart watch.

In an example, a device with light emitters and light receivers for measuring a biometric parameter can be embodied in a finger ring (e.g. smart ring). In an example, a device with light emitters and light receivers for measuring a biometric parameter can be embodied in a finger ring, smart watch, smart watch band, bracelet, bangle, armband, armlet, gauntlet, shirt cuff, or sleeve. In an example, the biometric parameter level which is measured and/or monitored by a biometric wearable device (e.g. finger ring or smart watch) can be blood oxygenation. In an example, the biometric parameter level which is measured and/or monitored by a biometric wearable device (e.g. finger ring or smart watch) can be heart rate. In an example, the biometric parameter level which is measured and/or monitored by a biometric wearable device (e.g. finger ring or smart watch) can be tissue oxygenation level.

In an example, a light emitter can be a Light Emitting Diode (LED). In an example, a light emitter can be a coherent light emitter. In an example, a light emitter can be a laser. In an embodiment, a light emitter can be a Light-Emitting Electrochemical Cell (LEC). In an example, a light emitter can be a Multi-Wavelength Light Emitting Diode (MWLED). In an example, a light emitter can be a Quantum Dot LED (QLED). In an example, a light emitter can be a Single Photon Avalanche Diode (SPAD). In an example, a light emitter can be a Vertical Cavity Surface Emitting Laser (VCSEL). In an example, a light emitter can be an Organic Photovoltaic (OPV). In an example, a light emitter can emit green light and/or be a green-light laser. In an example, one or more light emitters in a biometric wearable device (e.g. finger ring or smart watch) can be near-infrared light emitters. In an example, one or more light emitters in a biometric wearable device (e.g. finger ring or smart watch) can be a green-light lasers.

In an embodiment, a first light emitter in a wearable device (e.g. finger ring or smart watch) can be a red LED and a second light emitter in the device can be a green LED. In an example, a first light emitter in a wearable device (e.g. finger ring or smart watch) can emit red light and a second light emitter in the device can emit green light. In an example, a light emitter can be an ultraviolet light emitter. In an example, a light emitter can emit green visible light. In an example, one light emitter can emit red light, a second light emitter can emit infrared light, and a third light emitter can emit green light. In an example, one or more light emitters can be selected from the group consisting of: white LED, blue LED, red LED, infrared LED, and green LED. In an example, one or more light emitters in a device can be an infrared LED. In an example, one or more light emitters in a device can emit red light.

In an example, a biometric wearable device (e.g. finger ring or smart watch) can have a plurality of light emitter optical modules (e.g. sets), wherein each module includes at least three light emitters, including a red light emitter, an infrared (or near infrared) light emitter, and a green light emitter. In an embodiment, a biometric wearable device (e.g. finger ring or smart watch) can comprise an (approximately-circular) polygonal array of four optical modules (e.g. sets) of red, infrared, and green light emitters and four light receivers on the body-facing side of the housing of a wearable device. In an example, a biometric wearable device (e.g. finger ring or smart watch) can comprise at least three light emitters which emit light at different wavelengths.

In an example, a biometric wearable device (e.g. finger ring or smart watch) can comprise: a device which is configured to be worn around a body member (e.g. finger, wrist, and/or arm), wherein the device spans at least two-thirds of the circumference of the body member; and at least two optical sensor sets which are held in proximity to the body member by the device, wherein the optical sensor sets collectively span at least two-thirds of the circumference of the body member, and wherein each optical sensor set further comprises at least one red-light (e.g. infrared or visible red) emitter, at least one green-light emitter, at least one light receiver, and at least one electromagnetic actuator which automatically adjusts the distance and/or motion, orientation, and/or angle of the optical sensor set relative to the surface of the body member.

In an example, this biometric wearable device (e.g. finger ring or smart watch) can comprise: a device which is configured to be worn around a body member (e.g. finger, wrist, and/or arm), wherein the device spans at least two-thirds of the circumference of the body member; and at least eight optical sensor sets which are held in proximity to the body member by the device, wherein the optical sensor sets collectively span at least two-thirds of the circumference of the body member, and wherein each optical sensor set further comprises at least one red-light (e.g. infrared or visible red) emitter, at least one green-light emitter, at least one light receiver, and at least one electromagnetic actuator which automatically adjusts the distance and/or motion, orientation, and/or angle of the optical sensor set relative to the surface of the body member.

In a variation on this design, a biometric wearable device (e.g. finger ring or smart watch) can comprise: a finger ring which is configured to be worn around a person's finger, wherein the finger ring spans the circumference of the person's finger; and at least eight optical sensor sets which are held in proximity to the person's finger by the finger ring, wherein the optical sensor sets collectively span the circumference of the person's finger, and wherein each optical sensor set further comprises at least one red-light (e.g. infrared or visible red) emitter, at least one green-light emitter, at least one light receiver, and at least one electromagnetic actuator which automatically adjusts the distance and/or motion, orientation, and/or angle of the optical sensor set relative to the surface of the person's finger.

In an example, a biometric wearable device (e.g. finger ring or smart watch) can comprise: a finger ring which is configured to be worn around a person's finger, wherein the finger ring spans the circumference of the person's finger; and at least three optical sensor sets which are held in proximity to the person's finger by the finger ring, wherein the optical sensor sets collectively span the circumference of the person's finger, and wherein each optical sensor set further comprises at least one red-light (e.g. infrared or visible red) emitter, at least one green-light emitter, at least one light receiver, and at least one electromagnetic actuator which automatically adjusts the distance and/or motion, orientation, and/or angle of the optical sensor set relative to the surface of the person's finger.

In an example, a biometric wearable device (e.g. finger ring or smart watch) can comprise: a finger ring which is configured to be worn around a person's finger; and at least three optical sensor sets which are held in proximity to the person's finger, wherein the optical sensor sets collectively span at least two-thirds of the circumference of the person's finger, wherein each optical sensor set further comprises at least one red-light (e.g. infrared or visible red) emitter, at least one green-light emitter, and at least one light receiver, and wherein the at least light receiver in an optical sensor set is nested within an array of the at least one red-light (e.g. infrared or visible red) emitters and the at least one green-light emitters in the optical sensor set.

In an example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, and at least one piezoelectric actuator which automatically adjusts the orientation (and/or angle) of the optical sensor set relative to the surface of the body member to maintain a selected orientation (and/or angle) between the optical sensor set and the body member if the device moves relative to the body member.

In an embodiment, a biometric wearable device (e.g. finger ring or smart watch) can comprise: an arcuate band (or ring) which is configured to be worn around a body member (e.g. finger, wrist, and/or arm); and optical sensor sets which are held in proximity to the body member, wherein there is at least one optical sensor set in each of three quadrants of the circumference of the body member, and wherein each optical sensor set further comprises at least one red-light (e.g. infrared or visible red) emitter, at least one green-light emitter, at least one light receiver, and an actuator which adjusts the orientation (and/or angle) of the set relative to the body member to maintain a selected orientation (and/or angle) of the set relative to the body member.

In an example, a biometric wearable device (e.g. finger ring or smart watch) can include light emitters which emit light of different colors, at different wavelengths, at different frequencies, and/or with different light spectral distributions. In an example, a device with two light emitters which emit light with two different colors and/or wavelengths can be used to measure biometric parameters such as heart rate, heart rate variability, blood pressure, body hydration, and/or blood glucose level. In an example, a first light emitter can emit light with a wavelength in the range of 650 to 750 nm; a second light emitter can emit light with a wavelength in the range of 750 nm to 850 nm; and a third light emitter can emit light with a wavelength in the range of 850 nm to 950 nm.

In an example, a first light emitter can emit near-infrared light and a second light emitter can emit visible light. In an example, a first light emitter in a device can emit light at a wavelength in the range of 600 nm to 690 nm, a second light emitter in the device can emit light at a wavelength in the range of 710 nm to 950 nm, and a third light emitter in the device can emit light at a wavelength in the range of 1000 nm to 1500 nm. In an example, a light emitter can emit light with a wavelength in the range of 300 to 1200 nanometers. In an embodiment, a wearable device (e.g. finger ring or smart watch) can comprise at least three light emitters which emit light energy at different wavelengths.

In an example, an optical (e.g. spectroscopic) sensor can comprise a plurality of light emitters which emit light at different frequencies. In an example, different emitters can emit light with different wavelengths or wavelength ranges. In an example, light from the first light emitter can reflect primarily from a first depth, breadth, location, and/or type of body tissue and light from the second light emitter can reflect primarily from a second depth, breadth, location, and/or type of body tissue. In an example, there can be differences in the wavelengths, colors, and/or spectra of light emitted by light emitters at different circumferential locations in an array.

In an example, a light receiver can be a photodetector. In an example, a light receiver can be a flexible organic photodetector (OPD). In an example, a light receiver can be a thin-film photoreceptor. In an example, a light receiver can be selected from the group consisting of: photodetector, photoresistor, Avalanche Photodiode (APD), Charge-Coupled Device (CCD), Complementary Metal-Oxide Semiconductor (CMOS), infrared detector, infrared photoconductor, infrared photodiode, light dependent resistor (LDR), optoelectric sensor, photoconductor, photodiode, photomultiplier, and phototransistor.

In an embodiment, a biometric wearable device (e.g. finger ring or smart watch) can have a two-dimensional array of optical (e.g. spectroscopic) sensors comprising paired light emitters (or optical modules having light emitters) and light receivers. In an example, this biometric wearable device (e.g. finger ring or smart watch) can comprise one or more ultraviolet light optical (e.g. spectroscopic) sensors. In an example, a biometric wearable device (e.g. finger ring or smart watch) can comprise: a wearable device for measuring biometric parameter level with a close-fitting spectroscopic (e.g. optical) sensor comprising: (a) an attachment member, such as a strap or band, which is configured to span at least a portion of the circumference of a body member (e.g. finger, wrist, and/or arm); (b) an enclosure which is part of (or attached to) the attachment member; and (c) a rotating light-projecting spectroscopic (e.g. optical) sensor, wherein this sensor can be rotated relative to the enclosure and wherein rotation of this sensor relative to the enclosure changes the angle at which the sensor projects light onto the surface of the body member.

In an example, a biometric wearable device can comprise: a wearable device (e.g. finger ring or smart watch) worn around a body member (e.g. finger, wrist, and/or arm); a ring of spectroscopic (e.g. optical) sensor triads around the wearable device, wherein each triad further comprises two light emitters and one light receiver, and wherein light beams emitted by the two light emitters have different spectral ranges, frequencies, and/or colors; wherein a light receiver receives light beams emitted by a light emitter after the light beams have been transmitted through or reflected by the body member. In another example, a device which uses spectroscopic analysis to measure one or more biometric parameters can include one or more mirrors in addition to light emitters and light receivers.

In an example, a spectroscopic (e.g. optical) sensor can be rotated relative to the rest of the device, wherein rotating the spectroscopic (e.g. optical) sensor changes the angle at which the spectroscopic (e.g. optical) sensor projects a light beam onto the surface of a person's body. In an example, a spectroscopic sensor can further comprise one or more light emitters which emit light along different vectors at different times. In an example, a spectroscopic sensor can further comprise one or more light emitters which emit light at time-varying wavelengths. In another example, an optical (e.g. spectroscopic) sensor can comprise a linear array of light emitters which emit light pulses at different times. In a variation on this design, an optical (e.g. spectroscopic) sensor can comprise a plurality of light emitters which emit light at different times.

In an embodiment, an optical (e.g. spectroscopic) sensor can comprise an annular array of light emitters which emit light pulses at different times. In an example, changes in light characteristics (e.g. spectral distribution) caused by interaction of the light with the person's body tissue can be analyzed to measure one or more biometric parameters. In another example, changes in the intensity and/or spectral distribution of light caused by transmission through a body member (e.g. finger, wrist, or arm) can be analyzed to measure and/or monitor a biometric parameter level. In an example, changes, gaps, and/or shifts in selected frequencies in the spectral distribution of light caused by interaction with a person's body tissue and/or fluid can be analyzed to monitor changes in the chemical composition of the person's body tissue and/or fluid.

In another example, light from a light emitter which is received by a light receiver after the light has been reflected from and/or transmitted through body tissue (or fluid) can be analyzed to determine how the spectral distribution of that light has been changed by interaction with the body tissue (or fluid). In an example, rotating a spectroscopic (e.g. optical) sensor can change the angle at which the spectroscopic (e.g. optical) sensor projects a light beam onto the surface of the person's body. In an example, a light emitter in an optical module (e.g. set) can emit light which is transmitted through or reflected by a body member (e.g. finger, wrist, or arm). In an example, light from light emitters on a first side (e.g. left or right) of a biometric wearable device (e.g. finger ring or smart watch) can be received by light receivers on a second side (e.g. the opposite side) of the device after the light has been transmitted through or reflected by a body member (e.g. finger, wrist, or arm).

In an example, light from light emitters in a first quadrant of a biometric wearable device (e.g. finger ring or smart watch) can be received by light receivers in a second quadrant of the device after the light has been transmitted through or reflected by a body member (e.g. finger, wrist, or arm). In an example, optical modules (e.g. sets) in an dorsal-right quadrant of a biometric wearable device (e.g. finger ring or smart watch) can be closer together than those in an ventral-left quadrant of the device.

In an example, a biometric wearable device (e.g. finger ring or smart watch) can comprise a plurality of optical modules (e.g. sets) around the perimeter of the device. In an embodiment, a biometric wearable device (e.g. finger ring or smart watch) can comprise an annular and/or circular array of light emitters and light receivers on the body-facing surface of the circumference of the device. In another example, an array can be a circumferential array of pairs of light emitters and light receivers. In an example, light emitters and receivers in a biometric wearable device (e.g. finger ring or smart watch) can span between 60% and 85% of the perimeter of the device. In another example, light emitters in a circumferential array can be equally spaced and/or distributed around (a portion of) its circumference. In an example, the light emitters and light receiver can be located on the inward-facing (body-facing) side of a housing.

In another example, a biometric wearable device (e.g. finger ring or smart watch) can comprise: a finger ring; and an alternating ring of light emitters and light receivers around the inner (body-facing) circumference of the finger ring; wherein light receivers receive the light beams from the light emitters after the light beams have been transmitted through or reflected by the finger. In an example, a biometric wearable device can comprise: a wearable device (e.g. finger ring or smart watch) worn around a body member (e.g. finger, wrist, and/or arm); an annular array of light emitters and light receivers around the inner circumference of the device; wherein light receivers receive the light beams from the light emitters after the light beams have been transmitted through or reflected by the body member. In an example, a module (e.g. set) of light emitters in a circumferential array of light emitters can be two or more laterally-proximal light emitters which share the same polar coordinates.

In an example, a subset of light receivers in a circumferential array of light receivers can be two or more circumferentially-proximal light receivers with different polar coordinates. In an example, light emitters in an annular array can have polar coordinates which differ by 60 or 90 degrees. In an example, optical (e.g. spectroscopic) sensors in a two-dimensional array can differ in location circumferentially or annularly (e.g. be at different locations around the circumference of a wearable device) and laterally (e.g. be at different locations along axes which are perpendicular to the circumference of the device). In a variation on this design, proximal pairs of optical modules (e.g. sets) of light emitters in a circumferential array can have polar coordinates which differ by 15 degrees. In another example, proximal pairs of optical modules (e.g. sets) of light emitters in a circumferential array can have polar coordinates which differ by 60 degrees.

In an example, a biometric wearable device (e.g. finger ring or smart watch) can comprise a plurality of light emitters which emit light toward a person's body at a plurality of different angles with respect to a proximal surface of a person's body. In another example, a biometric wearable device (e.g. finger ring or smart watch) can comprise: a wearable device worn around (a portion of) a body member (e.g. finger, wrist, and/or arm); a first light emitter at a first radial location on the circumference of the wearable device which directs first light beams at a first angle toward the body member, a second light emitter at a second radial location on circumference of the wearable device which directs second light beams at a second angle toward the body member, a light receiver on the device which receives the first light beams and/or second light beams after the first light beams and/or the second light beams have been transmitted through or reflected by the body member.

In an embodiment, a biometric wearable device (e.g. finger ring or smart watch) can comprise: an attachment member which spans at least a portion of the circumference of a person's wrist (and/or arm); an enclosure (or housing) which is part of and/or attached to the attachment member; a first optical (e.g. spectroscopic) sensor in the enclosure (or housing) which projects a light beam onto the wrist (and/or arm) surface at a first angle relative to the enclosure; and a second optical (e.g. spectroscopic) sensor in the enclosure which projects a light beam onto the wrist (and/or arm) surface at a second angle relative to the enclosure (or housing), wherein the first angle differs from the second angle by at least 10 degrees.

In an example, a biometric wearable device can comprise: a wearable device (e.g. finger ring or smart watch) worn around a body member (e.g. finger, wrist, and/or arm); a first light emitter on the device whose light beams reach the surface of the body member at a first angle of incidence; a second light emitter on the device whose light beams reach the surface of the body member at a second angle of incidence; a light receiver on the device which receives the first light beams and/or second light beams after the first light beams and/or the second light beams have been transmitted through or reflected by the body member.

In an embodiment, a biometric wearable device can comprise: a wearable device (e.g. finger ring or smart watch) worn around a body member (e.g. finger, wrist, and/or arm); an automatically-rotating light emitter on the device whose light beams are directed toward the body member at a first incidence angle at a first time and a second incidence angle at a second time; a light receiver on the device which receives light beams emitted by a light emitter after the light beams have been transmitted through or reflected by the body member. In an example, a first light emitter can emit light along first angle and/or vector with respect to a person's body and a second light emitter in the array can emit light along a second angle and/or vector with respect to the person's body.

In an embodiment, a first light emitter which emits light in a first color can emit light along a first angle and/or vector and a second light emitter which emits light in a second color can emit light along a second angle and/or vector. In an example, an optical (e.g. spectroscopic) sensor can comprise a plurality of light emitters which emit light at different angles. In an example, different light emitters can emit light toward a person's body at different angles. In another example, light beams can be transmitted through or reflected by a body member (e.g. finger, wrist, or arm) along multiple vectors between multiple pairs of optical components.

In an example, a biometric wearable device (e.g. finger ring or smart watch) can have an array, matrix, or grid of four or more optical modules (e.g. sets) of light emitters, each of which is separated from the nearest other module by a (polar and/or angular) distance within the range of 2 degrees to 60 degrees. In another example, a biometric wearable device (e.g. finger ring or smart watch) can have a circular and/or annular array grid of four or more light emitters, each of which is separated from the nearest other light emitter by a (polar and/or angular) distance within the range of 40 degrees to 60 degrees.

In an example, a circumferential or annular array of light receivers can be evenly spaced or distributed, with the same pair-wise distance or number of degrees between adjacent light receivers. In another example, there can be a constant distance between (proximal or adjacent) light emitters in an array and/or configuration of light emitters. In a variation on this design, there can be differences in the distance and/or pressure between different light emitters and a body member (e.g. finger, wrist, or arm).

In an example, this biometric wearable device (e.g. finger ring or smart watch) can comprise a repeating sequence of light emitters and light receivers distributed around the perimeter of the device. In an example, a biometric wearable device (e.g. finger ring or smart watch) can further comprise a repeating (e.g. e1-e2-r) sequence of light emitters and light receivers around (a portion of) the perimeter of the device, wherein (e1) is a near-infrared light emitter, (e2) is a green light emitter, and (r) is a light receiver. In an example, there can be a repeating sequence of light emitters and light receivers around a circumferential line around (at least half of) the circumference of a device and/or around the circumference of a body member (e.g. finger, wrist, or arm). In an example, there can be a repeating sequence of two light emitters and a light detector around a perimeter of a biometric wearable device (e.g. finger ring or smart watch).

In an embodiment, a biometric wearable device (e.g. finger ring or smart watch) can comprise a checkerboard array, grid, and/or matrix of alternating light emitters and receivers. In an example, a biometric wearable device (e.g. finger ring or smart watch) can comprise a sinusoidal array, grid, and/or matrix of alternating light emitters and receivers. In another example, a biometric wearable device (e.g. finger ring or smart watch) can comprise an alternating sequence of light emitters and light receivers along a circumference of the device.

In an example, a biometric wearable device (e.g. finger ring or smart watch) can comprise: a wearable device worn around a body member; two or more concentric arcuate arrays (e.g. rings) of light emitters and light receivers around the device, wherein each arcuate array comprises an alternating sequence of light emitters and light receivers around the device, wherein the light receivers receive light beams from the light emitters after the light beams have been transmitted through or reflected by the body member. In another example, there can be an alternating sequence of light emitters and light receivers around a circumferential line around the circumference of a device and/or around (at least half of) the circumference of a body member (e.g. finger, wrist, or arm). In an example, an array of light emitters and light receivers can have a cylindrical and/or ring shape. In another example, an array of light emitters and light receivers can have a saddle shape. In an example, light emitters can be configured in a radial or hub-and-spoke array and/or configuration.

In an example, a biometric wearable device (e.g. finger ring or smart watch) can comprise a plurality of optical modules (e.g. modules or sets having light emitters and light receivers), wherein each module forms a vertex of an octagon. In a variation on this design, a plurality of light emitters can be configured in a circular or other arcuate array around a light receiver. In an example, a plurality of light emitters can be configured in a polygonal array including a light receiver. In an embodiment, a plurality of light receivers can be configured in a circular or other arcuate array including a light emitter. In another example, a plurality of light receivers can be configured in a polygonal array including a light emitter.

In an example, a substantially circular and/or annular array can be formed from a plurality of (sets of) light emitters and light receivers, wherein each forms a point on the circle. In another example, light emitters can be configured in a circular, annular, and/or nested array and/or configuration. In an example, light emitters can encircle the light receiver. In another example, light receivers can be configured in a polygonal array and/or configuration. In an example, optical modules (e.g. sets) of light emitters can be configured in a circular, annular, and/or nested array and/or configuration. In an example, the array can be a polygonal array.

In an example, a biometric wearable device (e.g. finger ring or smart watch) can comprise a circular or elliptical array, grid, and/or matrix of light emitters and light receivers. In an example, a biometric wearable device (e.g. finger ring or smart watch) can comprise a sunburst and/or radial-spoke array, grid, and/or matrix of light emitters and light receivers. In an example, an optical (e.g. spectroscopic) sensor can comprise light emitters and light receivers in a three-dimensional matrix or grid. In an example, a biometric wearable device (e.g. finger ring or smart watch) can comprise: a wearable device worn on a body member (e.g. finger, wrist, and/or arm); a light emitter on the device whose light beams are directed toward the body member along different incidence vectors at different times; and a light receiver on the device which receives light beams emitted by a light emitter after the light beams have been transmitted through or reflected by the body member.

In a variation on this design, this biometric wearable device can comprise: a wearable device (e.g. finger ring or smart watch) worn around a body member (e.g. finger, wrist, and/or arm); a light emitter on the device which emits light beams directed toward the body member at a first angle at a first time and at a second angle at a second time; wherein the second angle differs from the first angle by between 5 and 25 degrees; a light receiver on the device which receives light beams emitted by a light emitter after the light beams have been transmitted through or reflected by the body member.

In an embodiment, a biometric wearable device can comprise: a wearable device (e.g. finger ring or smart watch) worn around a body member (e.g. finger, wrist, and/or arm); light emitters which direct light beams along a first set of vectors toward the body member at a first time and direct light beams along a second set of vectors toward the body member at a second time; and a light receiver on the device which receives light beams emitted by a light emitter after the light beams have been transmitted through or reflected by the body member. In another example, a depth, breadth, location, and/or type of body tissue or fluid from which light from a light energy emitter is reflected can be changed by adjusting the angle of light emitted from the light energy emitter. In an example, a light emitter can be automatically tilted, rotated, raised, or lowered in order to maintain a selected angle (or angle range) with respect to the surface of a person's body.

In another example, a light emitter can emit light at an angle and/or along a focal vector which varies over time. In an embodiment, a light receiver of a wearable device for measuring a person's biometric parameter can be automatically moved relative to a housing which holds it. In another example, an angle at which light is emitted from a light emitter can be changed over time. In an example, an angle of light emitted from a light energy emitter can be adjusted automatically to maintain accurate measurement of a biometric parameter level even if a device shifts and/or moves relative to the person's body surface. In an embodiment, an angle of light which has been emitted from a light emitter in a ring can be automatically changed.

In an example, an optical (e.g. spectroscopic) sensor can further comprise an optical filter. In an example, different emitters in this array can emit light at different angles based on different biometric parameter levels or physiological conditions. In an example, the angle and/or vector of light which has been emitted from a light emitter can be automatically changed over time by the device. In an example, the angle at which light is emitted from a light emitter leaves a device and/or the angle at which the light intersects the surface of a person's body can be automatically changed over time. In another example, the projection angle of a light beam emitted from a light emitter can be changed in response to specific environmental conditions (e.g. temperature or humidity) and/or specific activities in which the person wearing a device is engaged (e.g. high level of movement, eating, sleeping, etc.).

In an example, a biometric wearable device (e.g. finger ring or smart watch) can comprise: a wearable device worn around a body member (e.g. finger, wrist, and/or arm); light emitters around the wearable device; moving light guides on the device, wherein the light guides change the vectors along which light beams from the light emitters travel in an iterative sinusoidal manner; and light receivers on the device which receive light beams from the light emitters after the light beams have been transmitted through or reflected by the body member. In another example, a biometric wearable device (e.g. finger ring or smart watch) can include one or more light guides, wave guides, and/or optical fibers which direct light from a first location, angle, and/or transmission vector to a second location, angle, and/or transmission vector.

In an example, a device can include dynamic optical components (e.g. movable light guides such as a movable mirrors, lenses, or prisms) which alter the patterns (e.g. transmission directions) of light beams emitted from light emitters. In another example, a device can include movable light guides (e.g. mirrors or lenses) which manipulate the light emission direction of light beams emitted from light emitters, thereby enabling the device to scan a body member (e.g. finger, wrist, or arm) at a selected transmission vector or in a selected sequence of transmission vectors. In an example, a device can include optical components such as mirrors, lenses, or prisms which alter the light patterns of light from light emitters.

In an example, a light beam emitted by a light emitter can be automatically moved by using an actuator to automatically move a light guide through which reflects this beam. In an example, a light beam emitted by a light emitter can be automatically moved by using an actuator to automatically rotate, tilt, raise, or lower a light guide which reflects this beam. In an example, a movable light guide can reflect and/or refract light from a light emitter at different angles (or along different vectors) toward a body member (e.g. finger, wrist, or arm) as the light guide pivots and/or rotates.

In an example, light beams emitted from light emitters can be redirected (e.g. refracted or reflected) by movable lenses or mirrors in order to change the optical paths taken by the light beams as they are transmitted through a body member (e.g. finger, wrist, or arm). In an example, one or more light emitters can deliver light to body tissue, organs, and/or fluid indirectly via one or more light guides, wave guides, and/or optical fibers. In an example, the transmission vectors (e.g. angle, location, and penetration depth) of light beams transmitted through a body member can be adjusted by movable lenses or mirrors which refract or reflect light beams emitted from light emitters.

In an example, a light guide can reflect light from a light emitter. In another example, light from a light emitter can be reflected by a light guide toward a body member (e.g. finger, wrist, or arm). In an embodiment, a light guide can be generally cylindrical and/or columnar. In another example, a light guide can direct light from a light emitter toward body tissue, organs, and/or fluid. In an example, a movable light guide can pivot and/or rotate. In another example, light from a first light emitter can reflected by a first side of a light guide toward a body member (e.g. finger, wrist, or arm) at a first time and light from a second light emitter can be reflected by a second (e.g. opposite) side of the light guide toward the body member (e.g. finger, wrist, or arm) at a second time.

In an example, a biometric wearable device (e.g. finger ring or smart watch) can comprise: a device worn around a body member (e.g. finger, wrist, and/or arm); a light emitter and an automatically tilting or rotating mirror, wherein light beams from the light emitter are directed toward the body member at a first angle at a first time and at a second angle at a second time; wherein the second angle differs from the first angle by between 1 and 90 degrees; and a light receiver on the device which receives light beams emitted by a light emitter after the light beams have been transmitted through or reflected by the body member.

In an example, a biometric wearable device (e.g. finger ring or smart watch) can comprise: a device worn around a body member (e.g. finger, wrist, and/or arm); a motion sensor; a circumferential array of light emitters, micromirrors, hydraulic actuators, and light receivers around the wearable device; wherein the micromirrors are automatically moved by the actuators based on data from the motion sensor; and wherein light receivers receive light beams from the light emitters after the light beams have been reflected by the micromirrors and been transmitted through or reflected by the body member.

In an embodiment, a biometric wearable device (e.g. finger ring or smart watch) can comprise: a device worn around a body member (e.g. finger, wrist, and/or arm); scanning light emitters on the device; moving micromirrors on the device; wherein light beams from the light emitters are directed (back and forth) along changing vectors (in an iterative manner) by the moving micromirrors; and light receivers on the device which receive light beams from the light emitters after the light beams have been transmitted through or reflected by the body member. In an example, a biometric wearable device (e.g. finger ring or smart watch) can comprise: a device worn on a body member (e.g. finger, wrist, and/or arm); a moving micromirror; a scanning light emitter whose light beams are reflected by the micromirror toward the body member along a first vector toward a first location on the body member during a first time interval and along a second vector toward a second location on the body member at during a second time interval; and a light receiver on the device which receives light beams emitted by the scanning light emitter after the light beams have been reflected by the micromirror and transmitted through or reflected by the body member.

In an example, a biometric wearable device (e.g. finger ring or smart watch) can comprise: a wearable device worn around a body member (e.g. finger, wrist, and/or arm); an arcuate array of pressure sensors; an arcuate array of mirrors; an arcuate array of actuators; an arcuate array of light emitters around the wearable device, wherein the light beams from the light emitters are reflected by the mirrors; wherein the mirrors are moved by the actuators based on data from the pressure sensors; an arcuate array of light receivers on the device which receive light beams from the light emitters after the light beams have been transmitted through or reflected by the body member. In another example, a biometric wearable device (e.g. finger ring or smart watch) can comprise: a wearable device worn on a body member (e.g. finger, wrist, and/or arm); a motion sensor on the device; light emitters on the device; moving micromirrors on the device, wherein the micromirrors reflect light beams from the light emitters travel, and wherein the micromirrors are moved based on data from the motion sensor so as to keep light beams from the light emitters directed toward one or more selected locations on the body member despite shifting or rotation of the wearable device relative to the body member; and light receivers on the device which receive light beams from the light emitters after the light beams have been transmitted through or reflected by the body member.

In an example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member, and wherein each optical sensor set further comprises at least one red-light (e.g. infrared or visible red) emitter, at least one green-light emitter, at least one light receiver, at least one micromirror, and at least one electromagnetic actuator which moves the at least one micromirror to redirect the vectors of light beams from light emitters.

In another example, a biometric wearable device can comprise: a wearable device (e.g. finger ring or smart watch) worn around a body member (e.g. finger, wrist, and/or arm); a convex array of light emitters around the wearable device; a convex array of micromirrors around the wearable device, wherein the micromirrors change the incidence angles at which light beams from the light emitters reach the surface of the body member; a convex array of light receivers around the wearable device which receive light beams from the light emitters after the light beams have passed through the micromirrors and been transmitted through or reflected by the body member.

In an embodiment, a biometric wearable device can comprise: a wearable device (e.g. finger ring or smart watch) worn around a body member (e.g. finger, wrist, and/or arm); a motion sensor; actuators; mirrors, wherein the orientations of the mirrors are changed by the actuators; light emitters, wherein light beams from the light emitters are reflected by the mirrors; wherein the vectors along which the light beams hit the body member are maintained, even if the wearable device shifts or rotates around the body member, by changing the orientations of the mirrors based on data from the motion sensor; light receivers which receive light beams from the light emitters after the light beams have been reflected by the mirrors and transmitted through or reflected by the body member.

In an example, a biometric wearable device can comprise: a wearable device (e.g. finger ring or smart watch) worn around a body member (e.g. finger, wrist, and/or arm); light emitters; moving micromirrors which reflect light beams from the light emitters; wherein light beams from the light emitters are reflected by the micromirrors along changing vectors so that the light beams are reflected from the body member at different tissue depths at different times; and light receivers which receive light beams emitted by the light emitters after the light beams have been reflected by the body member. In an example, a device which uses spectroscopic analysis to measure one or more biometric parameters can include one or more rotating and/or pivoting micromirrors which change the vectors of light beams emitted from light emitters.

In an example, a light beam emitted by a light emitter can be automatically moved by using an actuator to automatically move a light reflector (such as a mirror) from which this beam is reflected. In an example, angles and/or vectors of light emitted from light emitters can be automatically changed over time by movement of micromirrors, microprisms, or microlenses. In an example, optical modules (e.g. sets) can further comprise a plurality of movable mirrors which change the vectors of light rays from a plurality of light emitters. In another example, the angle at which light is emitted from a light emitter leaves a device and/or the angle at which the light intersects the surface of a person's body can be automatically changed over time by moving a mirror from which the light is reflected. In an example, a light guide can be a micromirror array. In another example, a light guide can be a moving (e.g. pivoting or rotating) mirror (e.g. micromirror). In an example, a movable light guide can be a pivoting and/or rotating (micro) mirror.

In another example, a device can further comprise one or more optical filters or lenses which change the projection and/or body incidence angle of a light beam emitted by a light energy emitter. In an example, a light beam emitted by a light emitter can be automatically moved by using an actuator to automatically rotate, tilt, raise, or lower a lens through which this beam is transmitted. In an example, an optical (e.g. spectroscopic) sensor can further comprise a lens array. In a variation on this design, a light guide can be a moving (e.g. pivoting or rotating) lens.

In an example, this biometric wearable device (e.g. finger ring or smart watch) can comprise: a wearable device worn around a body member (e.g. finger, wrist, and/or arm); a movable component (e.g. sphere or ball) on the device; a light emitter on the component, wherein light beams from a light emitter are automatically directed toward the body member at a first angle at a first time and at a second angle at a second time by moving the component; and a light receiver on the device which receives light beams emitted by a light emitter after the light beams have been transmitted through or reflected by the body member. In an embodiment, a device can include a light-projecting optical (e.g. spectroscopic) sensor on a rotating component (e.g. ball).

In an example, a light guide can be a moving (e.g. pivoting or rotating) prism which is moved by interaction with a changing electromagnetic field. In another example, a light guide can be a moving (e.g. pivoting or rotating) lens which is moved by interaction with a changing electromagnetic field. In an example, an optical module (e.g. set) can further comprise a movable light guide which is moved by interaction with a changing electromagnetic field. In another example, an optical module (e.g. set) can further comprise two electrodes, wherein transmission of electrical energy through the electrodes creates an electromagnetic field which moves (e.g. pivots or rotates) a light guide, thereby changing the angle at which light from a light emitter is reflected by the light guide into a body member (e.g. finger, wrist, or arm).

In an example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one motion sensor, and at least one piezoelectric actuator which automatically adjusts the orientation (and/or angle) of the optical sensor set relative to the surface of the body member in response to data from the motion sensor.

In another example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one motion sensor, and at least one microhydraulic (or micropneumatic) actuator which automatically adjusts the orientation (and/or angle) of the optical sensor set relative to the surface of the body member in response to data from the motion sensor.

In an example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one motion sensor, and at least one electromagnetic actuator which automatically adjusts the orientation (and/or angle) of the optical sensor set relative to the surface of the body member in response to data from the motion sensor.

In an example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one motion sensor, and at least one microhydraulic (or micropneumatic) actuator which automatically moves the optical sensor set to maintain a selected orientation (and/or angle) between the optical sensor set and the body member if the device moves relative to the body member.

In an example, a biometric wearable device (e.g. finger ring or smart watch) can comprise: an arcuate band (or ring) which is configured to be worn around a body member (e.g. finger, wrist, and/or arm); at least three optical sensor sets which are held in proximity to the body member, wherein the optical sensor sets collectively span at least two-thirds of the circumference of the body member; and wherein each optical sensor set further comprises at least one red-light (e.g. infrared or visible red) emitter, at least one green-light emitter, and at least one light receiver; at least motion sensor; and at least one microhydraulic (or micropneumatic) actuator which automatically adjusts the orientation (and/or angle) of one or more optical sensor sets relative to the body member in response to data from the motion sensor.

In an example, a biometric wearable device (e.g. finger ring or smart watch) can comprise: an arcuate band (or ring) which is configured to be worn around a body member (e.g. finger, wrist, and/or arm); at least three optical sensor sets which are held in proximity to the body member, wherein the optical sensor sets collectively span at least two-thirds of the circumference of the body member; and wherein each optical sensor set further comprises at least one red-light (e.g. infrared or visible red) emitter, at least one green-light emitter, and at least one light receiver; at least motion sensor; and at least one electromagnetic actuator which automatically adjusts the orientation (and/or angle) of one or more optical sensor sets relative to the body member. In an example, a device can include a motion sensor and can automatically change the angle and/or vector of light beams based on data from the motion sensor in order to scan the same local region of a person's body even if the device shifts and/or rotates with respect to the person's body. In an example, an angle and/or vector of a light beam emitted from a light emitter can be automatically changed by the device based on data from the one or more motion sensors.

In an embodiment, a biometric wearable device (e.g. finger ring or smart watch) can comprise: a device worn around a body member (e.g. finger, wrist, and/or arm); scanning light emitters on the device; actuators on the device; wherein light beams from the light emitters are directed along different vectors at different times by the actuators; and light receivers on the device which receive light beams from the light emitters after the light beams have been transmitted through or reflected by the body member.

In another example, a biometric wearable device (e.g. finger ring or smart watch) can comprise: a device worn around a body member (e.g. finger, wrist, and/or arm); scanning light emitters on the device; moving microlenses on the device; wherein light beams from the light emitters are directed along different vectors at different times by the moving microlenses; and light receivers on the device which receive light beams from the light emitters after the light beams have been transmitted through or reflected by the body member.

In a variation on this design, a biometric wearable device (e.g. finger ring or smart watch) can comprise: a wearable device such as a wearable band or finger ring; an arcuate array of scanning light emitters, wherein light beams from the light emitters are directed toward body tissue along different vectors at different times; and an arcuate array of light receivers which receive light beams from the light emitters after the light beams have been transmitted through or reflected by body tissue. In another example, a biometric wearable device (e.g. finger ring or smart watch) can comprise: a wearable device worn on a body member (e.g. finger, wrist, and/or arm); an actuator; a moving mirror which is moved in an iterative pattern by the actuator; a light emitter whose light beams are reflected by the mirror toward the body member along different vectors at different times in order to scan different areas of the body member; and a light receiver which receives light beams emitted by a light emitter after the light beams have been transmitted through or reflected by the body member.

In an example, a biometric wearable device (e.g. finger ring or smart watch) can comprise: a wearable device worn on a body member (e.g. finger, wrist, and/or arm); an array of actuators; an array of iteratively rotating and/or pivoting light emitters on the device which are rotated and/or pivoted by the actuators; and one or more light receivers which receive light beams from the light emitters after the light beams have been transmitted through or reflected by the body member. In another example, a biometric wearable device can comprise: a wearable device (e.g. finger ring or smart watch) worn around a body member (e.g. finger, wrist, and/or arm); a scanning light emitter which emits light beams which sweep over different areas of the surface of the body member along different vectors over time; and a light receiver on the device which receives light beams emitted by a light emitter after the light beams have been transmitted through or reflected by the body member.

In an example, a biometric wearable device can comprise: a wearable device (e.g. finger ring or smart watch) worn around a body member (e.g. finger, wrist, and/or arm); a scanning light emitter whose light beams follow different projection and/or incidence vectors at different times; and a light receiver which receives light beams emitted by a light emitter after the light beams have been transmitted through or reflected by the body member. In an example, a device can automatically vary an angle of light emitted from a light emitter in order to scan through a range of tissue depths, locations, and/or types to obtain more accurate measurement of a biometric parameter level.

In an example, a movable light guide in an optical module (e.g. set) in a biometric wearable device (e.g. finger ring or smart watch) can continuously oscillate (e.g. pivot or rotate) back-and-forth, thereby causing a beam of light from a light emitter to scan back and forth through a section of a body member (e.g. finger, wrist, or arm). In an example, a movable light guide in an optical module (e.g. set) in a biometric wearable device (e.g. finger ring or smart watch) can move (e.g. pivot and/or rotate) with a continuous back-and-forth (e.g. sinusoidal) movement. In an example, an angle and/or vector of light emitted from a light emitter can be automatically oscillated by a device. In an example, an angle of light emitted from a light energy emitter can be adjusted automatically (in an iterative manner) by a device in order to more accurately measure a biometric parameter level for a specific person, for a specific type of activity, or for a specific configuration of the device relative to the person's body surface.

In another example, beams of light emitted from different light emitters can hit the surface of a body member (e.g. finger, wrist, and/or arm) at different angles and/or vectors in order to scan different tissue depths and/or regions. In an example, pairs of light emitters and light receivers in different (e.g. opposite) quadrants can be activated at different times to scan a body member (e.g. finger, wrist, or arm) along different vectors.

In another example, a beam of light emitted by a light emitter can be automatically moved by using an actuator to automatically move a light guide through which this beam is transmitted. In an example, this biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one orientation (and/or angle) sensor, and at least one electromagnetic actuator which automatically moves the optical sensor set.

In another example, a biometric wearable device (e.g. finger ring or smart watch) can comprise: light emitters which direct light toward a person's body; light receivers which receive this light after it has been transmitted through or reflected by body tissue; and actuators (e.g. electromagnetic, pneumatic, or hydraulic actuators) which change the angles between the light emitters and the surface of the person's body and/or between light receivers and the surface of the person's body. In an embodiment, a device can include a sensor adjustment mechanism (e.g. an actuator) which moves a sensor relative to a body member (e.g. finger, wrist, or arm) to enable good optical communication (e.g. good optical contact between the sensor and the body member).

In a variation on this design, a light emitter can be automatically rotated by an actuator. In an example, a light emitter on a device can be automatically moved by an actuator relative to a wearable housing which holds it. In an example, a light receiver on a device can be automatically tilted, rotated, raised, or lowered by an actuator. In an example, an optical sensor (e.g. light emitter, light detector, or both) on a device can be moved by an actuator to enable good optical communication between the sensor and a body member (e.g. finger, wrist, or arm).

In an example, a biometric wearable device (e.g. finger ring or smart watch) can have a plurality of light emitter optical modules (e.g. sets), wherein each module includes multiple light emitters. In another example, a device for measuring one or more of a person's biometric parameters can comprise: a housing which is configured to be worn on a person's wrist, arm, or finger; and an array of light emitting optical modules (e.g. sets) and light receivers on the housing, wherein light emitted from the light emitters is transmitted through or reflected by the person's body tissue and received by the light receivers, and wherein attributes of the light received by the light receivers are analyzed to measure one or more biometric parameters of the person.

In an example, an optical module (e.g. set) can comprise two light emitters and a movable light guide (e.g. mirror), wherein the light guide is between the two light emitters. In another example, an optical module (e.g. set) can have multiple light emitters and one light receiver. In an example, an optical module (e.g. set) can have two light emitters and one light receiver. In another example, an optical module (e.g. set) can include one light receiver and at least four light emitters which are evenly-distributed around the light receiver. In an example, an optical module (e.g. set) can include one light emitter and at least four light receivers which are evenly-distributed around the light emitter.

In an example, an optical module (e.g. set) can include one light emitter and a plurality of light receivers distributed around the light emitter. In an example, an optical module (e.g. set) of light receivers in an array of light receivers can comprise two or more light receivers. In an embodiment, modules in a first module (e.g. set) can include light emitters and modules in a second module (e.g. set) of light emitters can include light receivers. In an embodiment, there can be three or more light emitters in each light emitter module (e.g. set). In an example, a light receiver can receive light from a light emitter which is located in a different optical module (e.g. set) than the light receiver.

In another example, a movable light guide in an optical module (e.g. set) can have a circular, elliptical, or oval shape. In a variation on this design, an optical module (e.g. set) can comprise a light receiver, a movable light guide, a first light emitter to one side of the light guide, and a second light emitter to the other side (e.g. opposite side) of the light guide, wherein light from the first light emitter is reflected by a first side of the light guide toward a body member (e.g. finger, wrist, or arm), and wherein light from the second light emitter is reflected by a second (e.g. opposite) side of the light guide toward the body member (e.g. finger, wrist, or arm). In another example, an optical module (e.g. set) can comprise: a first light emitter; a second light emitter; a light receiver; and a movable light guide (e.g. movable light reflector or refractor). In an example, an optical module (e.g. set) can include a movable light guide. In another example, an optical module (e.g. set) can include both a light emitter and a movable light guide.

In a variation on this design, a biometric wearable device (e.g. finger ring or smart watch) can comprise a optical modules (e.g. modules or sets having light emitters and light receivers), wherein different optical modules are activated at different times. In an example, a biometric wearable device (e.g. finger ring or smart watch) can have light emitters which emit light in a non-simultaneous (e.g. sequential) manner. In an example, a first light at a first polar coordinate can be activated to emit light at a first time and second light at a second polar coordinate can be activated to emit light at a second time. In an example, a first light emitter of a device can emit light at a first time and a second light emitter of the device can emit light at a second time.

In an example, activating different subsets of light emitters at different times can enable a light receiver to separately analyze light beams which have been reflected from, or transmitted through, body tissue along different pathways. In another example, an optical (e.g. spectroscopic) sensor can operate with time-based multiplexing. In an example, data from a sequentially-activated annular array of light emitters and light receivers can be used to create a two-dimensional image showing variation in biometric parameter levels within a virtual cross-section of a body member (e.g. finger, wrist, or arm). In another example, different combinations of light emitters in a circumferential or annular array can be activated at different times in order to measure combined effects of light reflected from, or having passed through, the body along different light pathways.

In an embodiment, different optical modules (e.g. sets) can be activated at different times to isolate different optical pathways. In another example, light emitters can be selectively and sequentially activated via time-based multiplexing. In an example, light emitters in a circumferential, annular, and/or circular array can be activated to shine, one light at a time. In an example, optical modules (e.g. sets) in an array of optical modules (e.g. sets) can be activated in a circumferential sequence. In an example, the lengths of time wherein light emitters are activated can be changed and/or adjusted to refine measurement of biometric parameter levels. In an example, there can be pauses between the times when different subsets of light emitters are activated in a circumferential array.

In an example, a biometric wearable device (e.g. finger ring or smart watch) can comprise: a wearable device worn around a body member (e.g. finger, wrist, and/or arm); electromagnetic energy sensors around the inner perimeter of the device; light emitters; wherein a selected subset of the plurality of light emitters are activated based on data from the electromagnetic energy sensors; and one or more light receivers on the device which receive light beams emitted by the light emitters after light beams have been transmitted through or reflected by the body member.

In another example, a biometric wearable device can comprise: a wearable device (e.g. finger ring or smart watch) worn around a body member (e.g. finger, wrist, and/or arm); a motion and/or orientation sensor; and light emitters; wherein a selected subset of the light emitters are activated to emit light beams based on the motion and/or orientation of the wearable device; and at least one light receiver on the device which receives light beams emitted by a light emitter after the light beams have been transmitted through or reflected by the body member. In an example, different emitters in an array can be activated to emit light based on biometric parameters or physiological conditions. In another example, the first light emitter can emit light during a first environmental condition and the second light emitter can emit light during a second environmental condition.

In a variation on this design, a first light emitter can emit a pulse of light with a first duration and a second light emitter can emit a pulse of light with a second duration, wherein the second duration is greater than the first duration. In another example, a light emitter can be a pulsatile laser. In an embodiment, a light emitter can emit light via Alternating Current Electroluminescence (ACEL).

In an example, a biometric wearable device (e.g. finger ring or smart watch) can comprise an optical (e.g. spectroscopic) sensor which emits a sequence of light at different frequencies. In an example, this biometric wearable device (e.g. finger ring or smart watch) can further comprise one or more optical filters or lenses which change the frequency, color, and/or spectrum of light emitted by a light emitter. In an example, a first light emitter which emits light in a first color can emit light with a first oscillation frequency and a second light emitter which emits light in a second color can emit light with a second oscillation frequency. In another example, a frequency, color, and/or spectrum of a light beam emitted from a light energy emitter can be changed over time to create a chronological sequence of beams of light with different frequencies, colors, and/or spectrums.

In another example, a light emitter can emit light with a first light wavelength (or wavelength range or spectral distribution) during a first time period and can emit light with a second light wavelength (or wavelength range or spectral distribution) during a second time period in response to changing environmental conditions. In another example, a light emitter can emit light with a frequency and/or spectrum which changes over time. In an example, a light emitter in a wearable device (e.g. finger ring or smart watch) can emit light with a first wavelength, color, and/or spectrum at a first time and emit light with a second wavelength, color, and/or spectrum at a second time. In an example, a light emitter of an optical (e.g. spectroscopic) sensor can emit light with a frequency which changes over time.

In another example, different emitters can emit light with different wavelengths or wavelength ranges based on when a person is engaged in different types of activities. In an example, the frequency and/or spectrum of light emitted by a light emitter can be changed over time. In another example, the frequency, color, and/or spectrum of light emitted from a light emitter can be adjusted automatically (in an iterative manner) by a device in order to more accurately measure biometric parameter level for a specific person, for a specific type of activity, or for a specific configuration of the device relative to the person's body surface.

In an embodiment, the frequency, color, and/or spectrum of light emitted from the light emitter can be adjusted automatically to maintain accurate measurement of body oxygenation, heart rate, heart rate variability, body hydration level, and/or blood glucose level even if the device shifts and/or moves relative to the person's body surface. In an example, the wavelength, color, and/or spectrum of light emitted by a light emitter can be automatically oscillated and/or iteratively-varied by a device in order to scan body tissue at different depths and/or locations. In an example, the wavelengths and/or frequencies of light from light emitters can be shifted up and down in a repeated pattern. In an example, the wavelengths and/or frequencies of light from light emitters can be changed in a sequential manner.

In a variation on this design, a biometric wearable device (e.g. finger ring or smart watch) can comprise: a wearable device worn around a body member (e.g. finger, wrist, and/or arm); one or more sensors on the device selected from the group consisting of motion sensor, muscle function monitor, near-infrared spectroscopic (e.g. optical) sensor, neural impulse monitor, neurosensor, optical sensor, and optoelectronic sensor; an arcuate array of light emitters around the device, wherein the power level of light beams emitted from the light emitters are changed based on data from the one or more sensors; and an arcuate array of light receivers around the device which receive light beams from the light emitters after the light beams have been transmitted through or reflected by the body member.

In another example, a first module (e.g. set) of light emitters can emit light at a first intensity or amplitude level (or at a first time) and a second module (e.g. set) of light emitters can emit light at a second intensity or amplitude level (or at a second time). In an example, a power or intensity of a light beam emitted from a light energy emitter can be changed over time to create a chronological sequence of beams of light with different power or intensity levels. In another example, the power and/or intensity of a light beam emitted from a light emitter can be changed in response to specific environmental conditions (e.g. temperature or humidity) and/or specific activities in which the person wearing a device is engaged (e.g. high level of movement, eating, sleeping, etc.) in order to more accurately measure a biometric parameter level.

In an example, the power and/or intensity of light emitted from the light emitter can be adjusted automatically (in an iterative manner) by a device in order to more accurately measure body oxygenation, heart rate, heart rate variability, body hydration level, and/or blood glucose level for a specific person, for a specific type of activity, or for a specific configuration of the device relative to the person's body surface. In another example, the power and/or intensity of light emitted from the light emitter can be adjusted. In an example, the coherence, polarization, and/or phase of light emitted from the light emitter can be adjusted in order to more accurately measure a biometric parameter level.

In an embodiment, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the plurality of optical sensor sets collectively span at least two-thirds of the circumference of the body member; and wherein each optical sensor set further comprises: at least one red-light (e.g. infrared or visible red) emitter, at least one green-light emitter, at least one light receiver, and at least one microhydraulic (or micropneumatic) actuator which automatically adjusts the distance (or proximity or pressure) between the optical sensor set and the body member to maintain a selected distance (or proximity or pressure) between the optical sensor set and the body member if the device moves relative to the body member.

In an example, this biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the plurality of optical sensor sets collectively span at least two-thirds of the circumference of the body member; and wherein each optical sensor set further comprises: at least one red-light (e.g. infrared or visible red) emitter, at least one green-light emitter, at least one light receiver, at least one motion sensor, and at least one electromagnetic actuator which automatically moves the set to maintain a selected distance (or proximity or pressure) between the optical sensor set and the body member if the device moves relative to the body member.

In an embodiment, a distance and/or pressure between a light emitter and a person's body can be automatically changed and/or oscillated by the device. In an example, a light emitter on a device can be automatically raised or lowered by an actuator. In an embodiment, the distance and/or pressure between a light emitter relative to the person's body can be automatically changed over time by the device. In an example, varying the distance between a light receiver and different light emitters at different times can measure analyte concentration at different tissue levels and locations in a body member (e.g. finger, wrist, or arm).

In an embodiment, a biometric wearable device (e.g. finger ring or smart watch) can automatically vary the location of a light emitter to scan through a range of tissue depths, locations, and/or types in order to obtain more accurate measurement of biometric parameter level. In another example, a biometric wearable device can comprise: a wearable device (e.g. finger ring or smart watch) worn around a body member (e.g. finger, wrist, and/or arm); a light emitter on a first side of the body member which slides along a circumferential track on the device; a light receiver on a second side of the body member which slides along the circumferential track on the device, wherein the second side is opposite the first side; wherein a light receiver receives light beams from a light emitter after the light beams have been transmitted through or reflected by the body member.

In an example, a biometric wearable device can comprise: a wearable device (e.g. finger ring or smart watch) worn around a body member (e.g. finger, wrist, and/or arm); an arcuate track, channel, or slot around (a portion of) the circumference of the wearable device; a light emitter which slides along the arcuate track, channel, or slot, wherein the light beams are directed toward the body member at a first angle at a first time and a second angle at a second time; wherein the second angle differs from the first angle by between 20 and 90 degrees; a light receiver on the device which receives light beams emitted by a light emitter after the light beams have been transmitted through or reflected by the body member.

In another example, a biometric wearable device can comprise: a wearable device (e.g. finger ring or smart watch) worn on a body member (e.g. finger, wrist, and/or arm); a first movable housing which can be moved to different locations on the circumference of the wearable device; a second movable housing which can be moved (independently of the first movable housing) to different locations on the circumference of the wearable device; wherein each movable housing has a light emitter and a light receiver, and wherein a light receiver on a housing receives light beams from a light emitter on the housing after the light beams have been transmitted through or reflected by the body member.

In an example, a light emitter on a body member (e.g. finger, wrist, or arm) can be automatically moved (e.g. rotated) by the device from one circumferential quadrant of the body member (e.g. finger, wrist, or arm) to another circumferential quadrant of the body member (e.g. finger, wrist, or arm). In another example, the circumferential (e.g. polar, compass, or clock-hour) location of a light emitter on the circumference of the body member (e.g. finger, wrist, or arm) can be automatically changed over time by the device. In an example, the depth, breadth, location, and/or type of body tissue or fluid through which light passes can be changed by adjusting the location or shape of a light emitter. In an example, the location or shape of a light emitter can be adjusted.

In a variation on this design, a biometric wearable device (e.g. finger ring or smart watch) can comprise: a device worn around a body member (e.g. finger, wrist, and/or arm); a motion sensor; an arcuate array of spectroscopic (e.g. optical) sensors around the device; wherein a spectroscopic (e.g. optical) sensor further comprises a light emitter, a microlens, and a light receiver; wherein the focal length of light beams from a light emitter in a spectroscopic (e.g. optical) sensor is automatically adjusted by a microlens in the spectroscopic (e.g. optical) sensor in order to maintain focus at a selected tissue depth in the body member even if the device shifts relative to the body member as detected by the motion sensor; and wherein a light receiver in a spectroscopic (e.g. optical) sensor receives light beams from a light emitter in the spectroscopic (e.g. optical) sensor after the light beams have been focused by a microlens in the spectroscopic (e.g. optical) sensor and transmitted through or reflected by the body member.

In an example, a biometric wearable device (e.g. finger ring or smart watch) can comprise: a wearable device worn around a body member (e.g. finger, wrist, and/or arm); a motion sensor; an actuator which automatically tightens the fit of the wearable device around the body member when the motion sensor detects vigorous movement; and an array of light emitters and light receivers around the wearable device; wherein light receivers which receive light beams from the light emitters after the light beams have been transmitted through or reflected by the body member.

In an example, a biometric wearable device (e.g. finger ring or smart watch) can comprise: a wearable device worn around a body member (e.g. finger, wrist, and/or arm); one or more sensors on the device selected from the group consisting of motion sensor, muscle function monitor, near-infrared spectroscopic (e.g. optical) sensor, neural impulse monitor, neurosensor, optical sensor, optoelectronic sensor, oximetry sensor, pH level sensor, photochemical sensor, photodetector, photoelectric sensor, photoplethysmographic (PPG) sensor, piezocapacitive sensor, piezoelectric sensor, piezoresistive sensor, plethysmographic sensor, pressure sensor, and pulse sensor; an arcuate array of light emitters around the device, wherein the operation of the array of light emitters is adjusted based on data from the one or more sensors; and an arcuate array of light receivers around the device which receive light beams from the light emitters after the light beams have been transmitted through or reflected by the body member.

In an example, a biometric wearable device (e.g. finger ring or smart watch) can comprise: an arcuate band (or ring) which is configured to be worn around a body member (e.g. finger, wrist, and/or arm); at least three optical sensor sets which are held in proximity to the body member, wherein the optical sensor sets collectively span at least two-thirds of the circumference of the body member, and wherein each optical sensor set further comprises at least one red-light (e.g. infrared or visible red) emitter, at least one green-light emitter, and at least one light receiver, at least one motion sensor, and at least one electromagnetic actuator which automatically moves the optical set in response to data from the motion sensor.

In an example, a biometric wearable device (e.g. finger ring or smart watch) can comprise: a device worn around a body member (e.g. finger, wrist, and/or arm); an electromagnetic energy sensor on the device; a circumferential array of light emitters around the wearable device, wherein the projection vectors of light beams emitted from the circumferential array of light emitters are changed based on data from the electromagnetic energy sensor; and one or more light receivers which receive light beams from the light emitters after the light beams have been transmitted through or reflected by the body member.

In another example, a biometric wearable device (e.g. finger ring or smart watch) can comprise: a wearable device worn around a body member (e.g. finger, wrist, and/or arm); a circumferential array of electromagnetic energy sensors around the wearable device; a circumferential array of light emitters around the wearable device, and wherein the projection vectors of the light beams emitted from the circumferential array of light emitters are changed based on data from the electromagnetic energy sensor; and one or more light receivers which receive light beams from the light emitters after the light beams have been transmitted through or reflected by the body member.

In an example, this biometric wearable device can comprise: a wearable device (e.g. finger ring or smart watch) worn around a body member (e.g. finger, wrist, and/or arm); an electromagnetic energy sensor on the device; an arcuate array of light emitters on the device, wherein a subset of light emitters in the arcuate array of light emitters are selected to emit light at a given time based on data from the electromagnetic energy sensor; one or more light receivers which receive light beams from the light emitters after the light beams have been transmitted through or reflected by the body member.

In another example, a biometric wearable device (e.g. finger ring or smart watch) can comprise: a finger ring which is configured to be worn around a person's finger; and at least three optical sensor sets which are held in proximity to the person's finger, wherein the plurality of optical sensor sets collectively span at least two-thirds of the circumference of the person's finger; and wherein each optical sensor set further comprises: at least one red-light (e.g. infrared or visible red) emitter, at least one green-light emitter, at least one light receiver, at least one orientation (and/or angle) sensor, and at least one actuator which automatically moves the optical sensor set.

In an example, a biometric wearable device (e.g. finger ring or smart watch) can comprise: a wearable device worn around a body member (e.g. finger, wrist, and/or arm); one or more sensors on the device selected from the group consisting of oximetry sensor, pH level sensor, photochemical sensor, photodetector, photoelectric sensor, photoplethysmographic (PPG) sensor, piezocapacitive sensor; an arcuate array of light emitters around the device, wherein the projection or incidence vectors of light beams emitted from the light emitters are changed based on data from the one or more sensors; and an arcuate array of light receivers around the device which receive light beams from the light emitters after the light beams have been transmitted through or reflected by the body member.

In another example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one orientation (and/or angle) sensor, and at least one piezoelectric actuator which automatically moves the optical sensor set to maintain a selected orientation (and/or angle) between the optical sensor set and the body member if the device moves relative to the body member.

In an example, this biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one orientation (and/or angle) sensor which measures the orientation (and/or angle) of the optical sensor set relative to the surface of the body member, and at least one microhydraulic (or micropneumatic) actuator which automatically adjusts the orientation (and/or angle) of the optical sensor set relative to the surface of the body member to maintain a selected orientation (and/or angle) between the optical sensor set and the body member if the device moves relative to the body member.

In an example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one orientation (and/or angle) sensor which measures the orientation (and/or angle) of the optical sensor set relative to the surface of the body member, and at least one piezoelectric actuator which automatically adjusts the orientation (and/or angle) of the optical sensor set relative to the surface of the body member.

In an embodiment, a biometric wearable device (e.g. finger ring or smart watch) can comprise: an arcuate band (or ring) which is configured to be worn around a body member (e.g. finger, wrist, and/or arm); at least three optical sensor sets which are held in proximity to the body member, wherein the optical sensor sets collectively span at least two-thirds of the circumference of the body member, and wherein each optical sensor set further comprises at least one red-light (e.g. infrared or visible red) emitter, at least one green-light emitter, and at least one light receiver, at least one orientation (and/or angle) sensor, and at least one piezoelectric actuator which moves the optical set relative to the rest of the arcuate band (or ring) in response to data from the orientation (and/or angle) sensor.

In an example, a biometric wearable device (e.g. finger ring or smart watch) can further comprise a chemical sensor, electromagnetic sensor, microphone, motion sensor, or photoplethysmography (PPG) sensor. In an example, a biometric wearable device (e.g. finger ring or smart watch) can include a photoplethysmography (PPG) sensor. In an example, a device or system can further comprise one or more other types of biometric or environmental sensors in addition to the primary light emitters and light receivers. In another example, a device or system can further comprise one or more sensors selected from the group consisting of: thermal energy sensor, electroporation sensor, thermistor, galvanic skin response (GSR) sensor, tissue impedance sensor, chemoreceptor sensor, pulmonary function sensor, and gyroscope.

In an example, a projection angle of a light beam emitted from a light energy emitter can be changed in response to specific environmental conditions (e.g. temperature or humidity) and/or specific activities in which the person wearing a device is engaged (e.g. high level of movement, eating, sleeping, etc.) in order to more accurately measure a biometric parameter level. In another example, a shape of a sensor can be adjusted when a person first wears the sensor in order to calibrate it to the specific anatomy and physiology of that person. In a variation on this design, an angle and/or vector of a light beam emitted from a light emitter can be automatically changed by the device based on data from the one or more distance and/or pressure sensors.

In another example, a biometric wearable device (e.g. finger ring or smart watch) can comprise: (a) a housing (e.g. finger ring or smart watch housing) which is worn on a body member (e.g. finger, wrist, or arm); an array of light emitting optical modules (e.g. sets) and light receivers on the housing; wherein light emitted from the light emitters is transmitted through or reflected by the person's body tissue and received by the light receivers; wherein attributes (e.g. the spectral distribution) of light received by the light receivers are analyzed to measure one or more biometric parameters and/or detect one more physiological conditions of the person; wherein the array has a circular, approximately-circular polygonal (e.g. hexagonal or octagonal), annular, or circumferential shape; wherein there is an alternating pattern of light emitting optical modules and light receivers around the perimeter of the array; wherein there are a plurality (e.g. three or more) of light emitters in each light emitter module; wherein different light emitters in an optical module emit light with different colors, wavelengths, and/or frequencies; and wherein at least one light emitter in an optical module emits red light, at least one light emitter in an optical module emits infrared light, and at least one light emitter in an optical module emits green light; and (b) one or more compressible, compliant, and/or elastomeric opaque light barriers surrounding one or more light receivers; wherein the one or more light barriers reduce or eliminate transmission of light from the light emitters to the light receivers which has not been reflected by or transmitted through the person's body tissue; and/or wherein the one or more light barriers reduce or eliminate transmission of ambient light to the light emitters.

In an example, a biometric wearable device (e.g. finger ring or smart watch) can include a circular, annular, circumferential, and/or polygonal light barrier between (sets of) light emitters in the device and light receivers in the device so that light from light emitters only reaches light receivers after it has been reflected by or transmitted through body tissue. In a variation on this design, a biometric wearable device (e.g. finger ring or smart watch) can include a plurality of light barriers and a plurality of light receivers, wherein there is one light barrier for each light receiver. In an example, a biometric wearable device (e.g. finger ring or smart watch) can include one or more light barriers (e.g. light shields, light blockers, cladding, and/or opaque barriers) between one or more light emitters and one or more light receivers which reduce the transmission of light energy directly from the light emitter to the light receiver (without intended light transmission through body tissue).

In an example, this biometric wearable device (e.g. finger ring or smart watch) can include two light barriers: one light barrier between light emitters in the device and light receivers in the device; and one light barrier between ambient light and light receivers in the device. In an example, a light barrier between a light emitter and a light receiver can be compressible, flexible, and/or elastic. In an example, a light barrier can be made from a compressible, compliant, and/or elastomeric opaque material. In an embodiment, a light barrier can be made from an opaque elastomeric silicone-based polymer. In another example, a light barrier can be made from opaque ink.

In an example, a light barrier can comprise a circular and/or annular opaque ring around a light receiver. In another example, a light barrier can comprise a polygon (e.g. quadrilateral, hexagon, or octagon shaped member) of opaque material between a light emitter and a light receiver (or module or set of light receivers). In an example, a light barrier can comprise a polygon (e.g. quadrilateral, hexagon, or octagon shaped member) of opaque material around a light receiver. In another example, a light barrier can comprise a ring of compressible, compliant, and/or elastomeric opaque material around a light receiver. In an example, a light barrier can comprise a ring of opaque material around a light receiver. In an example, a light barrier can encircle two or more light receivers.

In an example, a light barrier can have a circular, elliptical, or annular shape. In an example, a light barrier can have a polygonal (e.g. square, hexagonal, or octagonal) shape, wherein a light receiver is at the center of this shape. In an example, a light barrier can surround a perimeter around a light single emitter. In an example, a light barrier can surround a perimeter around a subset (e.g. two or more) of light receivers. In an embodiment, all light receivers in a wearable device can be optically isolated from ambient light by the same light barrier. In another example, each light barrier can surround a single light receiver.

In an example, each light receiver in a wearable device can be optically isolated from direct transmission (e.g. not through body tissue) of light from one or more light emitters by a circular and/or annular light barrier. In another example, light barriers can reduce or eliminate transmission of ambient light to the light emitters. In an example, subsets of one or more light receivers can be optically isolated from direct transmission (e.g. not through body tissue) of light from one or more light emitters by the same light barrier. In another example, there can be a circular and/or annular light barrier around each light receiver in a wearable device. In an example, there can be an opaque partition (e.g. light barrier) between a light emitter and a light receiver. In an example, a biometric wearable device (e.g. finger ring or smart watch) can further comprise one or more expandable chambers which are expanded by being filled with a flowable substance (e.g. air or a liquid).

In a variation on this design, this biometric wearable device can comprise: a ring which is configured to be worn around a person's finger, wherein the ring spans at least two-thirds of the circumference of the person's finger, wherein the ring has a plurality of radial undulations; and at least three optical sensor sets which are held in proximity to the person's finger, wherein the optical sensor sets are located on portions of the ring which protrude toward the surface of the person's finger, wherein the optical sensor sets collectively span at least two-thirds of the circumference of the person's finger, wherein each optical sensor set further comprises at least one red-light (e.g. infrared or visible red) emitter, at least one green-light emitter, and at least one light receiver.

In an example, a biometric wearable device can comprise: a ring which is worn on a person's finger; and at least three optical sensors, wherein the optical sensors are on portions of the ring which protrude toward the surface of the person's finger, and wherein an optical sensor comprises at least one infrared light emitter, red light emitter, green-light emitter, or light receiver. In a variation on this design, a biometric wearable device can comprise: a ring which is worn on a person's finger; inward-facing protrusions on portions of the ring; and optical sensors on the portions of the ring with protrusions, wherein an optical sensor comprises an infrared light emitter, a red light emitter, a green-light emitter, or a light receiver.

In an embodiment, a biometric wearable device can comprise: a wearable device (e.g. finger ring or smart watch) worn around a body member (e.g. finger, wrist, and/or arm); wherein the wearable device further comprises stretchable and/or elastic segments; and a plurality of light emitters and light receivers on the stretchable and/or elastic segments; wherein light receivers receive light beams from a light emitter after the light beams have been transmitted through or reflected by the body member. In an example, a first portion of a biometric wearable device (e.g. finger ring or smart watch) can have a first level of stretchability and a second portion of the device can have a second level of stretchability, wherein the second level is greater than the first level.

In an example, a first portion of a biometric wearable device (e.g. finger ring or smart watch) can have a first elasticity level and a second portion of the device can have a second elasticity level, wherein the second level is greater than the first level, and wherein optical modules (e.g. sets) (e.g. light emitters and receivers) are located on the second portion. In another example, a first portion of a biometric wearable device (e.g. finger ring or smart watch) can have a first level of stretchability and a second portion of the device can have a second level of stretchability, wherein the second value or level is greater than the first value or level.

In an example, a first portion of the circumference of a biometric wearable device (e.g. finger ring or smart watch) can have a first elasticity level and a second portion of the circumference of the device can have a second elasticity level, wherein the second level is greater than the first level, and wherein the first portion is larger than the second portion. In another example, a first portion of the circumference of a biometric wearable device (e.g. finger ring or smart watch) can have a first level of stretchability and a second portion of the circumference of the device can have a second level of stretchability, wherein the second level is greater than the first level, and wherein the first portion is between 20% and 40% of the circumference of the device.

In an example, a biometric wearable device (e.g. finger ring or smart watch) can include a data processor (e.g. central processing unit, microchip, and/or microprocessor). In another example, a device or system can further comprise a data processing unit or microprocessor. In an example, a biometric wearable device (e.g. finger ring or smart watch) can be a component of a system which includes a local data processor, a local data transmitter (which are contiguous parts of the device) and a remote (non-contiguous) data processor which receives data from the data transmitter. In an example, a biometric wearable device (e.g. finger ring or smart watch) can be in wireless communication with an external device selected from the group consisting of: a cell phone, an electronic tablet, electronically-functional eyewear, a home electronics portal, an implanted medical device, an internet portal, a laptop computer, a mobile computer, a mobile phone, a remote computer, a remote control unit, a smart phone, a smart utensil, a television set, and a wearable data processing hub. In an embodiment, a device or system can further comprise a augmented reality eyewear and/or smart eyewear. In an example, additional data processing and analysis can be done within an external device.

In an example, a biometric wearable device (e.g. finger ring or smart watch) can further comprise an energy source which powers a light emitter, a light receiver, a data processor, and/or a data transmitter. In an example, a device or system can further comprise a battery, energy transducer, or other power source. In an example, an energy source can transduce, harvest, and/or generate energy from body motion or kinetic energy. In another example, a biometric wearable device (e.g. finger ring or smart watch) can include an exterior indicator light. In an example, a biometric wearable device (e.g. finger ring or smart watch) can include a wireless data transmitter and/or wireless data receiver. In another example, a device or system can further comprise a keypad or buttons. In an example, the opposite (outward-facing) side of a device can comprise a computer display and/or screen.

In another example, data from a biometric wearable device (e.g. finger ring or smart watch) can be analyzed using Raman scattering to measure a biometric parameter level in a body member (e.g. finger, wrist, or arm). In an embodiment, data from a biometric wearable device (e.g. finger ring or smart watch) can be analyzed using Diffuse Optical Imaging (DOI) to measure a biometric parameter level in a body member (e.g. finger, wrist, or arm). In an example, data from a biometric wearable device (e.g. finger ring or smart watch) can be analyzed using Frequency Domain (FD) optical analysis. In an embodiment, data from a light receiver can be analyzed to measure a biometric parameter level using one or more methods selected from the group consisting of: Analysis of Variance (ANOVA), Artificial Neural Network (ANN), Auto-Regressive (AR) Modeling, Bayesian Analysis, Bonferroni Analysis (BA), Carlavian Curve Analysis (CCA), Centroid Analysis, Chi-Squared Analysis, Cluster Analysis, Correlation, Covariance, and Data Normalization (DN).

In an example, data from a light receiver can be analyzed to measure a biometric parameter level using one or more methods selected from the group consisting of: Inter-Band Power Ratio, Inter-Channel Power Ratio, Inter-Montage Power Mean, Inter-Montage Ratio, Kalman Filter (KF), Kernel Estimation, Laplacian Filter, Laplacian Montage Analysis, Least Squares Estimation, Linear Regression, Linear Transform, and Logit Model. In an example, data from a light receiver can be analyzed to measure a biometric parameter level using one or more methods selected from the group consisting of: Signal Averaging, Signal Decomposition, Sine Wave Compositing, Singular Value Decomposition (SVD), Spine Function, Support Vector and/or Machine (SVM), time Domain Analysis, time Frequency Analysis, time Series Model, Trained Bayes Classifier, Variance, Waveform Identification, Wavelet Analysis, and Wavelet Transformation.

In an example, a device with light emitters and light receivers for measuring a biometric parameter can be embodied in a smart watch (e.g. the watch housing, the watch strap, or both the housing and the strap). In a variation on this design, a device with light emitters and receivers for measuring a biometric parameter can be embodied in a wrist band (e.g. a fitness band). In an example, the biometric parameter level which is measured and/or monitored by a biometric wearable device (e.g. finger ring or smart watch) can be blood pressure. In another example, the biometric parameter level which is measured and/or monitored by a biometric wearable device (e.g. finger ring or smart watch) can be heart rate variability. In an example, the biometric parameter level which is measured and/or monitored by a biometric wearable device (e.g. finger ring or smart watch) can be pulse rate.

In another example, a light emitter can be a laser LED. In an example, a light emitter can be a Light Emitting Diode (LED). In another example, a light emitter can be a MicroLED. In another example, a light emitter can be a Nanoscale LED. In an example, a light emitter can be a Resonant Cavity Light Emitting Diode (RCLED). In an example, a light emitter can be a Super-Luminescent Light Emitting Diode (SLED). In an example, a light emitter can be an Active Matrix Organic Light-Emitting Diode (AMOLED). In an example, a light emitter can emit ultraviolet light. In an example, a light emitter can emit red light and/or be a red-light laser. In an example, one or more light emitters in a biometric wearable device (e.g. finger ring or smart watch) can be multi-wavelength lasers. In an embodiment, one or more light emitters in a biometric wearable device (e.g. finger ring or smart watch) can be Light-Emitting Electrochemical Cells (LECs).

In an example, a first light emitter in a wearable device (e.g. finger ring or smart watch) can be a red LED and a second light emitter in the device can be an infrared LED. In an example, a first light emitter in a wearable device (e.g. finger ring or smart watch) can emit red light and a second light emitter in the device can emit infrared light. In another example, a light emitter can emit red visible light. In an example, a light emitter can emit near-infrared light. In another example, one light emitter in a device can be a red LED, a second light emitter in a device can be an infrared LED, and a third light emitter in a device can be a green LED. In an example, one or more light emitters in a device can be a green LED. In another example, one or more light emitters in a device can emit green light.

In an example, this biometric wearable device (e.g. finger ring or smart watch) can have a plurality of light emitter optical modules (e.g. sets), wherein each module includes different light emitters which emit light with different colors, wavelengths, and/or frequencies, respectively. In an example, a biometric wearable device (e.g. finger ring or smart watch) can comprise an (approximately-circular) polygonal array of three optical modules (e.g. sets) of red, infrared, and green light emitters and three light receivers on the body-facing side of the housing of a wearable device. In an example, this biometric wearable device (e.g. finger ring or smart watch) can comprise a plurality of optical (e.g. spectroscopic) sensors which simultaneously emit light at different frequencies.

In an example, a biometric wearable device (e.g. finger ring or smart watch) can comprise at least three light emitters which emit light of different colors. In an embodiment, a biometric wearable device (e.g. finger ring or smart watch) can comprise: a device which is configured to be worn around a body member (e.g. finger, wrist, and/or arm), wherein the device spans at least two-thirds of the circumference of the body member; and at least three optical sensor sets which are held in proximity to the body member by the device, wherein the optical sensor sets collectively span at least two-thirds of the circumference of the body member, and wherein each optical sensor set further comprises at least one red-light (e.g. infrared or visible red) emitter, at least one green-light emitter, at least one light receiver, and at least one electromagnetic actuator which automatically adjusts the distance and/or motion, orientation, and/or angle of the optical sensor set relative to the surface of the body member.

In an example, a biometric wearable device (e.g. finger ring or smart watch) can comprise: a device which is configured to be worn around a body member (e.g. finger, wrist, and/or arm), wherein the device spans at least two-thirds of the circumference of the body member; and at least three optical sensor sets which are held in proximity to the body member by the device, wherein the optical sensor sets collectively span at least two-thirds of the circumference of the body member, and wherein each optical sensor set further comprises at least one red-light (e.g. infrared or visible red) emitter, at least one green-light emitter, and at least one light receiver.

In an example, a biometric wearable device (e.g. finger ring or smart watch) can comprise: a finger ring which is configured to be worn around a person's finger, wherein the finger ring spans the circumference of the person's finger; and at least eight optical sensor sets which are held in proximity to the person's finger by the finger ring, wherein the optical sensor sets collectively span the circumference of the person's finger, and wherein each optical sensor set further comprises at least one red-light (e.g. infrared or visible red) emitter, at least one green-light emitter, and at least one light receiver.

In another example, a biometric wearable device (e.g. finger ring or smart watch) can comprise: a finger ring which is configured to be worn around a person's finger, wherein the finger ring spans the circumference of the person's finger; and at least two optical sensor sets which are held in proximity to the person's finger by the finger ring, wherein the optical sensor sets collectively span the circumference of the person's finger, and wherein each optical sensor set further comprises at least one red-light (e.g. infrared or visible red) emitter, at least one green-light emitter, at least one light receiver, and at least one electromagnetic actuator which automatically adjusts the distance and/or motion, orientation, and/or angle of the optical sensor set relative to the surface of the person's finger.

In an example, a biometric wearable device (e.g. finger ring or smart watch) can comprise: a first light emitter which emits light at a wavelength in the range of 400 nm to 600 nm; and a second light emitter which emits light at a wavelength in the range of 680 nm to 880 nm. In another example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, and at least one electromagnetic actuator which automatically adjusts the orientation (and/or angle) of the optical sensor set relative to the surface of the body member to maintain a selected orientation (and/or angle) between the optical sensor set and the body member if the device moves relative to the body member.

In an example, a biometric wearable device (e.g. finger ring or smart watch) can comprise: at least three optical sensor sets which are held in proximity to the body member, wherein the optical sensor sets collectively span at least two-thirds of the circumference of the body member, and wherein each optical sensor set further comprises at least one red-light (e.g. infrared or visible red) emitter, at least one green-light emitter, at least one light receiver, and an adjustable telescoping cylinder (e.g. microscale shock absorber) between the optical sensor set and the rest of the device, wherein the telescoping cylinder. In another example, a biometric wearable device can comprise: a wearable device (e.g. finger ring or smart watch) worn around a body member (e.g. finger, wrist, and/or arm); a first ring of light emitters which emit light with a first spectral range; a second ring of light emitters which emit light with a second spectral range; and a ring of light receivers, wherein light receivers receive light beams from the light emitters after the light beams have been transmitted through or reflected by the body member.

In a variation on this design, a first light emitter can emit light with a first frequency and/or spectrum and a second light emitter can emit light with a second frequency and/or spectrum, wherein the second frequency and/or spectrum is different than the first frequency and/or spectrum. In an example, a first light emitter can emit light with a wavelength in the range of 650 to 700 nm; a second light emitter can emit light with a wavelength in the range of 700 nm to 750 nm; and a third light emitter can emit light with a wavelength in the range of 750 nm to 800 nm. In an example, a first light emitter can emit near-infrared light and a second light emitter can emit red light. In an example, a first light emitter in a wearable device (e.g. finger ring or smart watch) can emit light with a first wavelength, color, and/or spectrum and a second light emitter in the wearable ring of biometric sensors can emit light with a second wavelength, color, and/or spectrum.

In an embodiment, a light emitter can emit light with a wavelength in the range of 400 to 700 nanometers. In an example, a wearable device (e.g. finger ring or smart watch) can comprise at least three light emitters which emit light energy of different colors. In an example, an optical (e.g. spectroscopic) sensor can comprise a plurality of light emitters which emit light in different wavelength ranges. In an example, different light emitters in an optical module (e.g. set) can emit light with different colors, wavelengths, and/or frequencies, respectively. In another example, there can be a repeating sequence of two light emitters and a light detector around a perimeter of a biometric wearable device (e.g. finger ring or smart watch), wherein the two light emitters emit light at different wavelengths. In an example, a first light emitter can emit light with a first light power and/or intensity and a second light emitter can emit light with a second light power and/or intensity.

In another example, a light receiver can be a photoconductor. In an example, a light receiver can be a photodiode. In another example, a light receiver can be an organic photodiode. In an example, a light receiver can be selected from the group consisting of: photodiode, photomultiplier, photoconductor, avalanche photodiode, organic photodiode, organic photo-detector, silicon photodiode, photon multiplier, polarization-sensitive photodetector, Charge-Coupled Device (CCD), and Silicon Photo-Multiplier (SiPM).

In an example, a biometric wearable device (e.g. finger ring or smart watch) can comprise one or more near-infrared light optical (e.g. spectroscopic) sensors. In an example, a biometric wearable device (e.g. finger ring or smart watch) can comprise spectroscopic and microwave energy sensors. In a variation on this design, this biometric wearable device (e.g. finger ring or smart watch) can comprise: a wearable device for the arm with a close-fitting biometric sensor comprising: (a) an attachment member, such as a strap or band, which is configured to span at least a portion of the circumference of a body member (e.g. finger, wrist, and/or arm); (b) an enclosure which is part of (or attached to) the attachment member; and (c) a rotating light-projecting spectroscopic (e.g. optical) sensor, wherein this sensor can be rotated relative to the enclosure and wherein rotation of this sensor relative to the enclosure changes the angle at which the sensor projects light onto the surface of the body member. In an embodiment, a combination of one or more light emitters and one or more light receivers used for such analysis can be called a spectroscopic sensor or spectroscopy sensor. In an example, a spectroscopic (e.g. optical) sensor can be rotated relative to the rest of a device.

In an example, a spectroscopic sensor can be selected from the group consisting of: ambient light spectroscopic sensor, analytical chromatographic sensor, backscattering spectrometry sensor, spectroscopic camera, chemiluminescence sensor, chromatographic sensor, coherent light spectroscopic sensor, colorimetric sensor, fiber optic spectroscopic sensor, fluorescence sensor, gas chromatography sensor, infrared light sensor, infrared spectroscopic sensor, ion mobility spectroscopic sensor, laser spectroscopic sensor, liquid chromatography sensor, mass spectrometry sensor, near infrared spectroscopic sensor, optoelectronic sensor, photocell, photochemical sensor, photodetector, photoplethysmography (PPG) sensor, Raman spectroscopic sensor, spectral analysis sensor, spectrographic sensor, spectrometric sensor, spectrometry sensor, spectrophotometer, spectroscopic body hydration sensor, spectroscopic oximeter, ultraviolet light sensor, ultraviolet spectroscopic sensor, visible light spectroscopic sensor, and white light spectroscopic sensor. In an example, a spectroscopic sensor can further comprise one or more light emitters which emit light along time-varying vectors.

In another example, an angle between a housing and light emission from a light emitter (e.g. LED) which is part of a spectroscopic (e.g. optical) sensor can be adjusted. In an example, an optical (e.g. spectroscopic) sensor can comprise a plurality of light emitters in a polygonal configuration around a light receiver. In another example, an optical (e.g. spectroscopic) sensor can comprise a polygonal array with at least one light emitter and at least one light receiver. In an example, an optical (e.g. spectroscopic) sensor can comprise one light emitter and two light receivers.

In another example, changes in light from a light emitter which are caused by interaction with a body member (e.g. finger, wrist, or arm) can be analyzed to measure and/or monitor a biometric parameter level. In an example, changes in the spectral distribution of this light caused by this differential absorption can, in turn, be used to measure one or more biometric parameters. In an example, data from an optical (e.g. spectroscopic) sensor can be analyzed to determine how the spectral distribution of light has been changed by reflection from, or passage through, body tissue, organs, and/or fluid.

In an embodiment, one or more light emitters and one or more light receivers can comprise a spectroscopic sensor selected from the group consisting of: backscattering spectrometry sensor, infrared spectroscopy sensor, ion mobility spectroscopic sensor, mass spectrometry sensor, Near Infrared Spectroscopy sensor (NIS), Raman spectroscopy sensor, spectrometry sensor, spectrophotometer, spectroscopy sensor, ultraviolet spectroscopy sensor, and white light spectroscopy sensor. In an example, spectroscopic analysis of light transmitted through or reflected by body tissue can enable measurement of a biometric parameter. In an example, a light receiver can receive light from a light emitter after this light has been transmitted through or reflected by a body member (e.g. finger, wrist, or arm).

In a variation on this design, a light receiver can receive light from a light emitter which is located in a different quadrant of a biometric wearable device (e.g. finger ring or smart watch) than the light receiver. In an example, optical modules (e.g. sets) an dorsal-right quadrant of a biometric wearable device (e.g. finger ring or smart watch) can be closer together than optical modules (e.g. sets) in other quadrants of the device. In another example, there can be more optical modules (e.g. sets) in an dorsal-right quadrant of a biometric wearable device (e.g. finger ring or smart watch) than in the ventral-left quadrant of the device.

In an example, a biometric wearable device (e.g. finger ring or smart watch) can comprise an array of light emitters and light receivers on the body-facing surface of the circumference of the device. In another example, a biometric wearable device (e.g. finger ring or smart watch) can have a first circumferential or annular array of light emitters and light receivers around a first circumferential axis and a second circumferential or annular array of light receivers around a second circumferential axis, wherein the first and second circumferential axes are parallel to each other. In an example, incorporating multiple light emitters around the circumference of the device provides data on biometric parameter levels at different locations and tissue depths. In an example, a finger ring can have an outer-circumferential inscription which only appears when the ring is heated. In an embodiment, light emitters and receivers in a biometric wearable device (e.g. finger ring or smart watch) can span between 50% and 75% of the perimeter of the device. In an example, light receivers can be positioned on a common circumferential line.

In an example, a biometric wearable device (e.g. finger ring or smart watch) can have an array of optical (e.g. spectroscopic) sensors which are distributed around the radially-inward-facing circumference of the device. In an example, a biometric wearable device (e.g. finger ring or smart watch) can comprise: a wearable device such as a wearable band or finger ring worn around a body member (e.g. finger, wrist, and/or arm); light emitters at different locations around the circumference of the wearable device, wherein the light emitters project light beams along radial vectors which converge at the cross-sectional center of the body member; and light receivers which receive light beams from the light emitters after the light beams have been transmitted through or reflected by the body member.

In an example, a biometric wearable device can comprise: a wearable device (e.g. finger ring or smart watch) worn around a body member (e.g. finger, wrist, and/or arm); an array of light emitters at different locations around the circumference of the wearable device, wherein the light emitters project light beams which reach the surface of the body member along vectors which are (substantially) perpendicular to the surface of the body member; and an array of light receivers which receive light beams from the light emitters after the light beams have been transmitted through or reflected by the body member. In an example, a module (e.g. set) of light receivers in a circumferential array of light receivers can be two or more laterally-proximal light receivers which share the same polar coordinates.

In another example, Also, having an arcuate array of light emitters and light receivers around the circumference of a body member (e.g. finger, wrist, and/or arm) can ensure that at least some of the light emitters and light receivers remain in close optical communication with a selected tissue region and/or tissue depth even if the device shifts and/or rotates relative to the body member. In a variation on this design, light receivers in an annular array can have polar coordinates which differ by 60 or 90 degrees. In another example, proximal pairs of light emitters in a circumferential array can have polar coordinates which differ by 15, 30, 40, 60, or 90 degrees. In an example, proximal pairs of optical modules (e.g. sets) of light emitters in a circumferential array can have polar coordinates which differ by 30 degrees. In another example, proximal pairs of optical modules (e.g. sets) of light emitters in a circumferential array can have polar coordinates which differ by 90 degrees.

In an embodiment, a biometric wearable device (e.g. finger ring or smart watch) can comprise a plurality of light emitters which emit light toward a person's body at a plurality of different angles, respectively. In an example, a biometric wearable device (e.g. finger ring or smart watch) can comprise: a wearable device worn around a body member (e.g. finger, wrist, and/or arm); an actuator; a light emitter whose light beams hit the body member at different incidence angles at different times, wherein the actuator changes the incidence angle of the light beams to different angles at different times; and a light receiver which receives light beams emitted by a light emitter after the light beams have been transmitted through or reflected by the body member.

In an example, a biometric wearable device can comprise: a wearable device (e.g. finger ring or smart watch) worn around a body member (e.g. finger, wrist, and/or arm); a convex array of light emitters around the wearable device; a convex array of microlenses around the wearable device, wherein the microlenses change the incidence angles at which light beams from the light emitters reach the surface of the body member; a convex array of light receivers around the wearable device which receive light beams from the light emitters after the light beams have passed through the microlenses and been transmitted through or reflected by the body member.

In an example, this biometric wearable device can comprise: a wearable device (e.g. finger ring or smart watch) worn around a body member (e.g. finger, wrist, and/or arm); actuators on the device; light emitters on the device, wherein the vectors along which light beams are emitted from the light emitters are automatically changed over time by the actuators to create a chronological sequence of beams with different projection and/or body incidence angles; and one or more light receivers which receive light beams from the light emitters after the light beams have been transmitted through or reflected by the body member. In an example, a first light emitter can emit beams of light which reach the surface of a person's body at a first angle and/or vector with respect to the surface of the person's body and a second light emitter can emit beams of light which reach the surface of the person's body at a second angle and/or vector with respect to the surface of the person's body.

In an example, a first light emitter can emit light at a first angle with respect to a wearable device and a second light emitter can emit light at a second angle with respect to the wearable device, wherein the second angle is different than the first angle. In an example, a light emitter can emit light along a first vector and a light receiver can receive light along a second vector. In an example, different emitters can emit light at different angles with respect to a body surface. In another example, different light emitters in a wearable device can emit beams of light which reach the surface of a person's body at different angles and/or along different vectors with respect to the surface of the person's body. In an embodiment, optical modules (e.g. sets) in a ring can be sequentially-activated (e.g. in a clockwise sequence around the ring) to transmit pulses of light into a body member (e.g. finger, wrist, or arm) along different vectors at different times.

In another example, a biometric wearable device (e.g. finger ring or smart watch) can have an array, matrix, or grid of four or more optical modules (e.g. sets) of light emitters, each of which is separated from the nearest other module by a distance within the range of 2 mm to 5 cm. In another example, a biometric wearable device (e.g. finger ring or smart watch) can have an array, matrix, or grid of four or more light emitters, each of which is separated from the nearest other light emitter by a (polar and/or angular) distance within the range of 2 degrees to 60 degrees. In an example, proximal pairs of light emitters in a circumferential array on a wearable device (e.g. finger ring or smart watch) can be separated by the same number of polar degrees and/or the same distance. In a variation on this design, there can be a constant distance between (proximal or adjacent) light receivers in an array and/or configuration of light receivers.

In an example, a biometric wearable device (e.g. finger ring or smart watch) can further comprise an alternating sequence of light emitters and light receivers around the device. In an example, this biometric wearable device (e.g. finger ring or smart watch) can further comprise a repeating (e.g. e1-e2-r) sequence of light emitters and light receivers around (a portion of) the perimeter of the device, wherein (e1) is a near-infrared light emitter, (e2) is a red light emitter, and (r) is a light receiver. In an example, a biometric wearable device (e.g. finger ring or smart watch) can further comprise a repeating (e.g. e1-e2-r) sequence of light emitters and light receivers around (a portion of) the perimeter of the device, wherein (e1) is a light emitter with first wavelength, (e2) is a light emitter with second wavelength, and (r) is a light receiver. In an example, there can be a repeating sequence of three different light wavelengths and/or colors in an arcuate array of light emitters around (at least half of) the circumference of a body member (e.g. finger, wrist, or arm).

In an example, a biometric wearable device (e.g. finger ring or smart watch) can comprise an array of alternating optical modules (e.g. sets) of red, infrared, and green light emitters and light receivers on the body-facing side of the device. In an embodiment, a biometric wearable device (e.g. finger ring or smart watch) can comprise a circular or elliptical array, grid, and/or matrix of alternating light emitters and receivers. In an example, a biometric wearable device (e.g. finger ring or smart watch) can comprise a sunburst and/or radial-spoke array, grid, and/or matrix of alternating light emitters and receivers.

In an example, a biometric wearable device (e.g. finger ring or smart watch) can comprise an annular and/or circular alternating (e.g. emitter then receiver) array of light emitters and light receivers on the body-facing surface of the circumference of the device. In another example, a biometric wearable device (e.g. finger ring or smart watch) can comprise: a wearable device worn around a body member; two or more nested arcuate arrays (e.g. rings) of light emitters and light receivers around the device, wherein each arcuate array comprises an alternating sequence of light emitters and light receivers around the device, wherein the light receivers receive light beams from the light emitters after the light beams have been transmitted through or reflected by the body member.

In an example, a plurality of light receivers can be configured in a linear array including a light emitter. In another example, an array of light emitters and light receivers can have a helical shape. In an example, an array of light emitters and light receivers can have a square or rectangular shape. In another example, light receivers can be configured in a radial or hub-and-spoke array and/or configuration. In a variation on this design, a biometric wearable device (e.g. finger ring or smart watch) can comprise a circular, annular, and/or octagonal array of light emitters and/or light receivers. In an example, a plurality of light emitters can be configured in a circular or other arcuate array including a light receiver. In an example, a plurality of light emitters in an optical module (e.g. set) can be distributed around a light receiver in a circular or polygonal pattern. In an embodiment, a plurality of light receivers can be configured in a polygonal array around a light emitter.

In an example, a plurality of light receivers in an optical module (e.g. set) can be distributed around a light emitter in a circular or polygonal pattern. In an example, an array of light emitters and light receivers can have a circular shape. In an embodiment, light emitters can be configured in a hexagonal or octagonal array and/or configuration. In an example, light receivers can be configured in a circular, annular, and/or nested array and/or configuration. In an embodiment, optical modules (e.g. sets) of light emitters can be configured in a polygonal array and/or configuration. In an example, the array can be a circular, annular, or circumferential array.

In another example, a biometric wearable device (e.g. finger ring or smart watch) can have an array, matrix, or grid of optical modules (e.g. sets), wherein each optical module further comprises at least one light emitter and at least one light receiver. In an example, a biometric wearable device (e.g. finger ring or smart watch) can comprise a linear array, grid, and/or matrix of light emitters and light receivers. In another example, a biometric wearable device (e.g. finger ring or smart watch) can comprise a three-dimensional stacked array, grid, and/or matrix of light emitters and light receivers.

In another example, a biometric wearable device (e.g. finger ring or smart watch) can comprise: a wearable device worn around a body member (e.g. finger, wrist, and/or arm); a first light emitter which emits first light beams; a second light emitter which emits second light beams; and a light receiver which receives light beams emitted by the light emitters after the light beams have been transmitted through or reflected by the body member; wherein a biometric parameter level is measured by changes in the spectra of the light beams; and wherein the first light beams and the second light beams change over time with respect to one or more characteristics selected from the group consisting of: beam projection vector, beam body incidence vector, beam breadth or size, and distance from light receiver.

In an example, a biometric wearable device can comprise: a wearable device (e.g. finger ring or smart watch) worn around a body member (e.g. finger, wrist, and/or arm); a first light emitter on the device which directs first light beams toward the body member, wherein the first light beams are directed toward the body member at a first time at a first angle relative to the surface of the wearable device, and wherein the first light beams are directed toward the body member at a second time at a second angle relative to the surface of the wearable device, wherein the second angle differs from the first angle; a second light emitter on the device which directs second light beams toward the body member, wherein the second light beams are directed toward the body member at a first time at a third angle relative to the surface of the wearable device, and wherein the second light beams are directed toward the body member at a second time at a fourth angle relative to the surface of the wearable device, wherein the fourth angle differs from the third angle; a light receiver on the device which receives the first light beams and/or second light beams after the first light beams and/or the second light beams have been transmitted through or reflected by the body member.

In an example, this biometric wearable device can comprise: a wearable device (e.g. finger ring or smart watch) worn around a body member (e.g. finger, wrist, and/or arm); a light emitter which emits light beams directed toward the body member at a first angle at a first time and at a second angle at a second time; wherein the second angle differs from the first angle by between 20 and 90 degrees; a light receiver which receives light beams emitted by a light emitter after the light beams have been transmitted through or reflected by the body member. In a variation on this design, a biometric wearable device can comprise: a wearable device (e.g. finger ring or smart watch) worn around a body member (e.g. finger, wrist, and/or arm); light emitters which emit light beams along changing projection vectors so that the light beams are reflected from the body member at different tissue depths at different times; and light receivers which receive light beams emitted by the light emitters after the light beams have been reflected by the body member.

In an example, a device can automatically change the angle and/or vector of light beams in order to maintain the same angle and/or vector of incidence with respect to the surface of a person's body. In an example, a light emitter can be automatically tilted, rotated, raised, or lowered when the wearable housing which holds it moves relative to the body surface on which it is worn. In another example, a light receiver can be automatically tilted, rotated, raised, or lowered if a wearable housing which holds it moves relative to the body surface on which it is worn. In another example, an angle and/or vector of light emitted from a light emitter can be automatically changed over time by a device. In another example, an angle between a device and light emission from a light emitter (e.g. LED) can be automatically adjusted. In an example, an angle of light emitted from the light energy emitter can be adjusted automatically to maintain accurate measurement of a biometric parameter level even if the device shifts and/or moves relative to the person's body surface.

In an example, an electronic device worn on a person's finger (e.g. a finger ring) can include light emitters and light receivers, wherein angles between the light emitters and the surface of the person's body are adjusted and/or wherein angles between light receivers and the surface of the person's body are adjusted. In an example, automatic adjustment by the device of the location, angle, and/or distance of light emitters in an array can help to ensure that light emitters and light receivers in the array remain in close optical communication with the surface of a body member (e.g. finger, wrist, and/or arm) even if the device shifts and/or rotates relative to the body member. In another example, different emitters in this array can emit light at different angles based on different environmental parameters or conditions. In another example, the angle at which light is emitted from a light emitter can be changed over time. In another example, the angle of a light beam emitted from a light emitter can be changed over time to create a chronological sequence of beams of light with different projection and/or body incidence angles.

In an embodiment, a biometric wearable device (e.g. finger ring or smart watch) can comprise: a device worn around a body member (e.g. finger, wrist, and/or arm); a motion sensor; light emitters; light guides, wherein light beams from the light emitters are redirected (e.g. reflected or refracted) by the light guides, and wherein the orientations of the light guides are automatically changed by electromagnetic, hydraulic, or pneumatic actuators based on data from the motion sensor; and light receivers which receive light beams from the light emitters after the light beams have been redirected by the light guides and transmitted through or reflected by the body member.

In an example, a biometric wearable device (e.g. finger ring or smart watch) can comprise: a wearable device worn on a body member (e.g. finger, wrist, and/or arm); a motion sensor on the device; light emitters on the device; moving light guides on the device, wherein the light guides change the vectors along which light beams from the light emitters travel, and wherein the light guides are moved based on data from the motion sensor so as to keep light beams from the light emitters directed toward one or more selected locations on the body member despite shifting or rotation of the wearable device relative to the body member; and light receivers on the device which receive light beams from the light emitters after the light beams have been transmitted through or reflected by the body member.

In another example, a biometric wearable device can comprise: a wearable device (e.g. finger ring or smart watch) worn around a body member (e.g. finger, wrist, and/or arm); a convex array of light emitters around the wearable device; a convex array of light guides around the wearable device, wherein the light guides change the incidence angles at which light beams from the light emitters reach the surface of the body member; and a convex array of light receivers around the wearable device which receive light beams from the light emitters after the light beams have passed through the light guides and been transmitted through or reflected by the body member. In an example, a device can include light emitters, light detectors, and optical components (e.g. movable mirrors or lenses) which redirect light beams emitted from the light emitters, thereby enabling adjustment of the vectors along which they light beams are transmitted through a body member (e.g. finger, wrist, or arm).

In another example, a device can include movable light guides (e.g. mirrors or lenses) which change the direction of light beams emitted from light emitters to scan a body member (e.g. finger, wrist, or arm) along a selected vector or along a selected sequence of vectors. In an example, a device which uses spectroscopic analysis to measure one or more biometric parameters can include one or more light guides, wave guides, and/or optical fibers which change the vectors of light beams emitted from light emitters. In another example, a light beam emitted by a light emitter can be automatically moved by using an actuator to automatically move a light guide through which this beam is transmitted. In an example, a light guide, wave guide, or optical fiber can direct light from a light emitter toward body tissue, organs, and/or fluid.

In an example, a movable light guide can reflect and/or refract light from a first light emitter and/or a second light emitter at different angles (or along different vectors) toward a body member (e.g. finger, wrist, or arm) as the light guide pivots and/or rotates. In an embodiment, movement (e.g. pivoting and/or rotation) of a light guide can change the vector along which light from an optical module (e.g. set) is transmitted through or reflected by a body member (e.g. finger, wrist, or arm). In a variation on this design, the angles of light beams emitted from light emitters can be changed by movable lenses or mirrors in order to change the optical paths (e.g. transmission vectors) taken by the light beams as they are transmitted through a body member (e.g. finger, wrist, or arm). In an example, a light emitter can emit a beam of light toward a light guide along a vector which is substantially parallel to a side of an optical module (e.g. set) and the light guide can redirect (e.g. reflect) this beam of light toward a body member (e.g. finger, wrist, or arm). In an example, a light guide can refract light from a light emitter.

In an example, a biometric wearable device (e.g. finger ring or smart watch) can comprise: a wearable device such as a wearable band or finger ring worn around a body member (e.g. finger, wrist, and/or arm); a circumferential array of light emitters around the wearable device; a circumferential array of light guides around the wearable device, wherein the light guides are made from one or more materials selected from the group consisting of optical-pass material, polycarbonate, polyethylene, polymer, polyurethane, resin, sapphire, and transparent polymer; a circumferential array of light receivers which receive light beams from the light emitters after the light beams have been transmitted through or reflected by the body member. In another example, a light guide can be made from one or more materials selected from the group consisting of: acrylic, crystal, elastomeric light-transmissive material, glass, high-durometer plastic, low-durometer plastic, optical-pass material, polycarbonate, polyethylene, polymer, polyurethane, resin, sapphire, and transparent polymer. In an example, a smart ring can be used to make payments while shopping, thus becoming "one ring to rule the mall." In another example, a light guide can direct light reflected from, or having passed through, body tissue, organs, and/or fluid toward a light receiver.

In an example, a movable light guide can reflect and/or refract light from a first light emitter toward a body member (e.g. finger, wrist, or arm) when the light guide is in a first configuration and can reflect and/or refract light from a second light emitter toward the body member (e.g. finger, wrist, or arm) when the light guide is in a second configuration. In another example, a beam of light emitted by a light emitter can be automatically moved by using an actuator to automatically rotate, tilt, raise, or lower a light reflector (such as a mirror) from which this beam is reflected. In an example, a biometric wearable device (e.g. finger ring or smart watch) can comprise: a device worn around a body member (e.g. finger, wrist, and/or arm); a light emitter and an automatically-moving micromirror on the device, wherein light beams from a light emitter are directed by the micromirror toward the body member at a first angle at a first time and at a second angle at a second time; and a light receiver on the device which receives light beams emitted by a light emitter after the light beams have been reflected by the micromirror and have been transmitted through or reflected by the body member.

In an embodiment, a biometric wearable device (e.g. finger ring or smart watch) can comprise: a device worn around a body member (e.g. finger, wrist, and/or arm); an array of light emitters and moving micromirrors, wherein the light beams are directed by the micromirrors toward the body member along a first plurality of vectors at a first time and along a second plurality of vectors at a second time; and light receivers which receive light beams emitted by the light emitters after the light beams have been transmitted through or reflected by the body member.

In an example, a biometric wearable device (e.g. finger ring or smart watch) can comprise: a device worn around a body member (e.g. finger, wrist, and/or arm); scanning light emitters on the device; moving micromirrors on the device; wherein light beams from the light emitters are directed (back and forth) along changing vectors (in a circular or elliptical pattern) by the moving micromirrors; and light receivers on the device which receive light beams from the light emitters after the light beams have been transmitted through or reflected by the body member.

In an example, a biometric wearable device (e.g. finger ring or smart watch) can comprise: a wearable device such as a wearable band or finger ring worn around a body member (e.g. finger, wrist, and/or arm); a circumferential array of moving micromirrors; a circumferential array of light emitters, wherein light emitters in the array of light emitters direct light beams toward the body along vectors which are changed over time by reflection from the array of micromirrors; and a circumferential array of light receivers which receive light beams from the light emitters after the light beams have been reflected by the array of micromirrors and (or passed through) a portion of the body member.

In an example, a biometric wearable device (e.g. finger ring or smart watch) can comprise: a wearable device worn around a body member (e.g. finger, wrist, and/or arm); light emitters and moving micromirrors, wherein the light beams are directed by the micromirror array along a first set of projection vectors at a first time and a second set of projection vectors at a second time based on shifting or rotation of the wearable device relative to the body member and wherein the light beams reach the body member at the same set of incidence vectors at the first and second times despite shifting or rotation of the wearable device relative to the body member; and light receivers which receive light beams emitted by the light emitters after the light beams have been transmitted through or reflected by the body member.

In an example, a biometric wearable device (e.g. finger ring or smart watch) can comprise: a wearable device worn on a body member (e.g. finger, wrist, and/or arm); a moving micromirror; at least one light emitter on the device whose light beams are reflected by the moving micromirror toward the body member; and at least one light receiver which receives light beams emitted by a light emitter after the light beams have been transmitted through or reflected by the body member. In an example, this biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member, and wherein each optical sensor set further comprises at least one red-light (e.g. infrared or visible red) emitter, at least one green-light emitter, at least one light receiver, at least one micromirror, and at least one actuator which moves the at least one micromirror to scan light beams from light emitters through different tissue depths of the body member.

In an example, a biometric wearable device can comprise: a wearable device (e.g. finger ring or smart watch) worn around a body member (e.g. finger, wrist, and/or arm); a convex array of light emitters around the wearable device; a convex array of moving micromirrors around the wearable device, wherein the micromirrors change the incidence angles at which light beams from the light emitters reach the surface of the body member; a convex array of light receivers around the wearable device which receive light beams from the light emitters after the light beams have passed through the micromirrors and been transmitted through or reflected by the body member.

In another example, a biometric wearable device can comprise: a wearable device (e.g. finger ring or smart watch) worn around a body member (e.g. finger, wrist, and/or arm); a motion sensor; an actuator; a mirror, wherein the mirror is moved by the actuator; a light emitter, wherein light beams from a light emitter are reflected by the mirror; wherein the vector along which light beams from a light emitter hit the body member is maintained even if the wearable device shifts or rotates around the body member by adjustment of the orientation of the mirror by the actuator; a light receiver which receive light beams from a light emitter after the light beams have been reflected by the mirror and transmitted through or reflected by the body member. In another example, a device which uses spectroscopic analysis to measure one or more biometric parameters can include one or more micromirrors which change the vectors of light beams emitted from light emitters.

In an example, a light beam emitted by a light emitter can be automatically moved by using an actuator to automatically move a light reflector (such as a mirror) from which this beam is reflected. In another example, a light beam emitted by a light emitter can be automatically moved by using an actuator to automatically rotate, tilt, raise, or lower a light reflector (such as a mirror) from which this beam is reflected. In an embodiment, angles and/or vectors of light which has been emitted from light emitters can be automatically changed over time by movement of micromirrors, microprisms, or microlenses. In a variation on this design, the angle and/or vector of light which has been emitted from a light emitter can be automatically changed over time by movement of a micromirror, microprism, or microlens. In an example, the angles at which an array of optical modules (e.g. sets) (e.g. including light emitters) direct light into a body member (e.g. finger, wrist, or arm) can be changed (e.g. controlled) by an array of movable micromirrors.

In an example, a light guide can be a mirror (e.g. micromirror). In an example, a movable light guide can be a digital micromirror biometric wearable device. In an example, a beam of light emitted by a light emitter can be automatically moved by using an actuator to automatically rotate, tilt, raise, or lower a lens through which this beam is transmitted. In an example, a device can include one or more optical filters or lenses which change the projection and/or body incidence angle of a light beam emitted by a light energy emitter. In an embodiment, a light beam emitted from a light emitter can be automatically moved by using an actuator to automatically change the focal distance of a lens through which this beam is transmitted. In an example, the angle at which light is emitted from a light emitter leaves a device and/or the angle at which the light intersects the surface of a person's body can be automatically changed over time by moving a lens, prism, or lightguide through which the light is transmitted. In an example, a light guide can be a prism.

In another example, a biometric wearable device (e.g. finger ring or smart watch) can comprise: a wearable device worn around a body member (e.g. finger, wrist, and/or arm); a moving component (e.g. sphere or ball) on the device; a light emitter on the moving component whose light beams are directed toward the body member at a first angle at a first time and at a second angle at a second time; and a light receiver which receives light beams emitted by a light emitter after the light beams have been transmitted through or reflected by the body member. In an example, a device can include a rotating component (e.g. ball) with a light emitter, wherein rotating the component changes the angle at which the light emitter projects light onto the surface of a body member (e.g. finger, wrist, and/or arm).

In another example, a light guide can be a moving (e.g. pivoting or rotating) mirror (e.g. micromirror) which is moved by interaction with a changing electromagnetic field. In an example, a light guide can be pivoted and/or rotated by changes in an electromagnetic field. In another example, an optical module (e.g. set) can further comprise a movable reflective light guide which is moved by interaction with a changing electromagnetic field. In an example, an optical module (e.g. set) can further comprise two electrodes, wherein changing the power and/or polarity of electrical energy transmitted through the electrodes changes an electromagnetic field which moves (e.g. pivots or rotates) a light guide.

In an example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one motion sensor, and at least one piezoelectric actuator which automatically adjusts the orientation (and/or angle) of the optical sensor set relative to the surface of the body member.

In an example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one motion sensor, and at least one microhydraulic (or micropneumatic) actuator which automatically adjusts the orientation (and/or angle) of the optical sensor set relative to the surface of the body member.

In an embodiment, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one motion sensor, and at least one electromagnetic actuator which automatically adjusts the orientation (and/or angle) of the optical sensor set relative to the surface of the body member to maintain a selected orientation (and/or angle) between the optical sensor set and the body member if the device moves relative to the body member.

In an example, a biometric wearable device (e.g. finger ring or smart watch) can comprise: an arcuate band (or ring) which is configured to be worn around a body member (e.g. finger, wrist, and/or arm); at least three optical sensor sets which are held in proximity to the body member, wherein the optical sensor sets collectively span at least two-thirds of the circumference of the body member; and wherein each optical sensor set further comprises at least one red-light (e.g. infrared or visible red) emitter, at least one green-light emitter, and at least one light receiver; at least motion sensor; and at least one piezoelectric actuator which automatically adjusts the orientation (and/or angle) of one or more optical sensor sets relative to the body member.

In a variation on this design, a biometric wearable device (e.g. finger ring or smart watch) can comprise: an arcuate band (or ring) which is configured to be worn around a body member (e.g. finger, wrist, and/or arm); at least three optical sensor sets which are held in proximity to the body member, wherein the optical sensor sets collectively span at least two-thirds of the circumference of the body member; and wherein each optical sensor set further comprises at least one red-light (e.g. infrared or visible red) emitter, at least one green-light emitter, and at least one light receiver; at least motion sensor; and at least one microhydraulic (or micropneumatic) actuator which automatically adjusts the orientation (and/or angle) of one or more optical sensor sets relative to the body member.

In an example, a biometric wearable device (e.g. finger ring or smart watch) can comprise: one or more light emitters which direct light toward a person's body; one or more light receivers which receive this light after it has been transmitted through or reflected by body tissue; one or more motion sensors; and actuators (e.g. electromagnetic, pneumatic, or hydraulic actuators) which adjust the angles between the light emitters and the surface of the person's body and/or between light receivers and the surface of the person's body based on motion detected by the one or more motion sensors. In an example, a device can include a motion sensor and can automatically change the angle and/or vector of light beams based on data from the motion sensor in order to scan the same tissue depth even if the device shifts and/or rotates with respect to the person's body. In another example, an angle and/or vector of a light beam which has been emitted from a light emitter can be automatically changed by the device based on data from the one or more motion sensors.

In an example, a biometric wearable device (e.g. finger ring or smart watch) can comprise: a device worn around a body member (e.g. finger, wrist, and/or arm); scanning light emitters on the device; an array of moving microlenses on the device; wherein light beams from the light emitters are directed (back and forth) along changing vectors (in an iterative manner) by the moving microlenses; and light receivers on the device which receive light beams from the light emitters after the light beams have been transmitted through or reflected by the body member.

In another example, a biometric wearable device (e.g. finger ring or smart watch) can comprise: a device worn on a body member (e.g. finger, wrist, and/or arm); a scanning light emitter which directs light beams toward the body member along a first vector toward a first location on the body member during a first time interval and along a second vector toward a second location on the body member at during a second time interval; and a light receiver on the device which receives light beams emitted by the scanning light emitter after the light beams have been transmitted through or reflected by the body member.

In another example, a biometric wearable device (e.g. finger ring or smart watch) can comprise: a wearable device worn around a body member (e.g. finger, wrist, and/or arm); an actuator; a light emitter on the device; and a light receiver on the device which receives light beams emitted by a light emitter after the light beams have been transmitted through or reflected by the body member, wherein the actuator changes the vector along which a light emitter emits light beams in an iterative manner. In an example, this biometric wearable device (e.g. finger ring or smart watch) can comprise: a wearable device worn on a body member (e.g. finger, wrist, and/or arm); an actuator; a moving mirror which is tilted or rotated by the actuator; a light emitter whose light beams are reflected by the mirror toward the body member along different vectors at different times in order to scan different areas of the body member; and a light receiver which receives light beams emitted by a light emitter after the light beams have been transmitted through or reflected by the body member.

In an example, a biometric wearable device can comprise: a wearable device (e.g. finger ring or smart watch) worn around a body member (e.g. finger, wrist, and/or arm); a circumferential array of scanning light emitters whose light beams are directed along different projection and/or incidence vectors at different times; and a circumferential array of light receivers which receive light beams emitted by a light emitter after the light beams have been transmitted through or reflected by the body member. In an example, this biometric wearable device can comprise: a wearable device (e.g. finger ring or smart watch) worn around a body member (e.g. finger, wrist, and/or arm); a scanning light emitter which emits light beams which sweep over different depths of the body member along different vectors over time; and a light receiver on the device which receives light beams emitted by a light emitter after the light beams have been transmitted through or reflected by the body member.

In an embodiment, a biometric wearable device can comprise: a wearable device (e.g. finger ring or smart watch) worn around a body member (e.g. finger, wrist, and/or arm); light emitters, wherein the projection vectors of light beams from the light emitters vary over time in an iterative manner; and light receivers which receive light beams emitted by the light emitters after the light beams have been transmitted through or reflected by the body member. In an example, a device can automatically vary the angle of light from a light emitter to scan through a range of tissue depths, locations, and/or types in order to obtain more accurate measurement of a biometric parameter level. In an example, a movable light guide in an optical module (e.g. set) in a biometric wearable device (e.g. finger ring or smart watch) can move (e.g. pivot and/or rotate) in an intermittent manner, thereby causing a beam of light from a light emitter to scan through a body member (e.g. finger, wrist, or arm) at a sequence of discrete angles (e.g. discrete vectors).

In an example, a projection angle of light from a light emitter in an optical (e.g. spectroscopic) sensor can be changed in an automatic, iterative, and/or scanning manner. In an example, an angle and/or vector of light which has been emitted from a light emitter can be automatically oscillated and/or iteratively-varied by a device. In a variation on this design, as different light emitters are activated in an array on a body member (e.g. finger, wrist, or arm), cross-sectional (and/or volumetric) scanning of biometric parameter levels can be possible. In another example, different light emitter and light receiver pairs can be activated at different times to scan a body member (e.g. finger, wrist, or arm) along different vectors. In an example, the angle and/or vector of light which has been emitted from a light emitter can be automatically oscillated and/or iteratively-varied by the device. In another example, a biometric wearable device (e.g. finger ring or smart watch) can include a plurality of electromagnetic actuators which change the angles and/or focal vectors of light beams which scan through a body member (e.g. finger, wrist, or arm).

In an example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one orientation (and/or angle) sensor which measures the orientation (and/or angle) of the optical sensor set relative to the surface of the body member, and at least one electromagnetic actuator which automatically adjusts the orientation (and/or angle) of the optical sensor set relative to the surface of the body member.

In another example, a biometric wearable device (e.g. finger ring or smart watch) can comprise: light emitters which direct light toward a person's body; light receivers which receive this light after it has been transmitted through or reflected by body tissue; and actuators (e.g. electromagnetic, pneumatic, or hydraulic actuators) which change the angles between the light emitters and the surface of the person's body. In an embodiment, a device can include a sensor adjustment mechanism moved by an actuator which maintains good contact between the sensor and a body member (e.g. finger, wrist, or arm). In an example, a light emitter can be automatically tilted by an actuator. In an example, a light emitter on a device can be automatically rotated by an actuator. In an example, an optical sensor (e.g. light emitter, light detector, or both) on a device can be moved by an actuator. In an example, the angles at which an array of optical modules (e.g. sets) (e.g. including light emitters) direct light into a body member (e.g. finger, wrist, or arm) can be changed (e.g. controlled) by an array of electromagnetic actuators.

In an example, a biometric wearable device (e.g. finger ring or smart watch) can comprise an array of optical modules (e.g. modules or sets having light emitters and light receivers). In an example, a paired light emitter and light receiver can both be located on a line which is orthogonal to a circumferential line of the device. In another example, an optical module (e.g. set) can computer eight light emitters and a light receiver. In an example, an optical module (e.g. set) can have multiple light emitters and a light receiver which are configured in an arcuate array. In another example, an optical module (e.g. set) can include a light emitter and a light receiver.

In an example, an optical module (e.g. set) can include one light receiver and a plurality of light emitters which are evenly-distributed around the light receiver. In another example, an optical module (e.g. set) can include one light emitter and a plurality of light receivers. In a variation on this design, an optical module (e.g. set) can include only a light emitter. In an embodiment, each optical module (e.g. set) in a device can have a first light emitter which emits light with a first frequency and a second light emitter which emits light with a second frequency. In an example, optical modules (e.g. sets) of light emitters can be configured in a radial or hub-and-spoke array and/or configuration. In an embodiment, within an optical sensor module (e.g. set), a light receiver can be centrally located with respect to a plurality of light emitters.

In an example, a movable light guide in an optical module (e.g. set) in a biometric wearable device (e.g. finger ring or smart watch) can have a square or rectangular shape. In an example, a movable light guide in an optical module (e.g. set) can pivot and/or rotate around a central (longitudinal) axis. In an example, an optical module (e.g. set) can comprise a light receiver, a movable light guide, a first light emitter to one side of the light guide, and a second light emitter to the other side of the light guide. In an example, an optical module (e.g. set) can include a light emitter, a movable light guide, and a light receiver. In an example, an optical module (e.g. set) can include a movable reflective light guide.

In another example, a biometric wearable device (e.g. finger ring or smart watch) can comprise: a device worn around a body member (e.g. finger, wrist, and/or arm); at least ten light emitters which are distributed around the circumference of the wearable device, wherein the light emitters are activated to emit light beams in a sequential (clockwise or counter-clockwise) manner around the circumference of the wearable device; and at least one light receiver on the device which receives the light beams from the light emitters after the light beams have been transmitted through or reflected by the body member. In an example, a biometric wearable device (e.g. finger ring or smart watch) can comprise: an annular array which alternates between light emitters and light receivers around a device, wherein light emitters in the array are activated to emit light at different times in a clockwise (or counter-clockwise) sequence, and wherein light receivers receive light beams from light emitters after the light beams have been transmitted through or reflected by the body member.

In another example, a clockwise (or counter-clockwise) sequence of light emitters can be activated to cause a series of light emissions which encircle the circumference of a device around a finger, wrist, or arm. In an example, a first light emitter can emit light at a first time and a second light emitter can emit light at a second time. In another example, a first subset of light emitters can emit light at a first time and a second subset of light emitters can emit light at a second time. In an embodiment, activating light emitters in different locations around the circumferential or annular array can enable light beam triangulation to measure biometric parameter levels in specific (cross-sectional) areas of a body member (e.g. finger, wrist, or arm). In an example, an optical module (e.g. set) can comprise light emitters which emit light in a circular sequence around a light receiver.

In an example, data from a sequentially-activated circumferential array of light emitters and light receivers can be used to create a two-dimensional image showing variation in biometric parameter levels within a virtual cross-section of a body member (e.g. finger, wrist, or arm). In an example, different light emitters can emit energy at different times and/or in a chronological sequence. In an example, different optical modules (e.g. sets) can be activated at different times. In an example, light emitters in a circumferential array can be activated in a clockwise (or counter-clockwise) sequence.

In an example, light receivers can be configured to receive light from the first subset of light emitters at a first point in time after light from this subset has interacted with the person's body tissue and the light receivers can be configured to receive light from the second subset of light emitters at a second point in time after light from this subset has interacted with the person's body tissue. In another example, optical modules (e.g. sets) in an array of optical modules (e.g. sets) can be activated in a sequential manner. In a variation on this design, the speed with which light emitters in a circle around a finger, wrist, or arm are sequentially activated in a clockwise (or counter-clockwise) manner can be increased or decreased based on analysis of light spectra.

In another example, a biometric wearable device (e.g. finger ring or smart watch) can comprise: a device worn around a body member (e.g. finger, wrist, and/or arm); an array, grid, or matrix of light emitters and light receivers on the device; and a motion sensor on the device; wherein a subset of light emitters are activated at a given time based on the type of activity in which the person is engaged based on data from the motion sensor; and wherein light receivers receive light beams from light emitters after light beams have been transmitted through or reflected by the body member.

In an embodiment, a biometric wearable device (e.g. finger ring or smart watch) can comprise: a wearable device worn on a body member (e.g. finger, wrist, and/or arm); an accelerometer and gyroscope, wherein data from the accelerometer and gyroscope is analyzed to determine the motion and/or orientation of the device relative to the body member; and light emitters and light receivers; wherein a subset of light receivers and/or light receivers is activated at a given time based on the motion and/or orientation of the device relative to the body member; wherein light receivers receive light beams emitted by activated light emitters after the light beams have been transmitted through or reflected by the body member.

In another example, a biometric wearable device can comprise: a wearable device (e.g. finger ring or smart watch) worn around a body member (e.g. finger, wrist, and/or arm); an arcuate array of electromagnetic energy sensors, wherein data from the electromagnetic energy sensors is analyzed to determine the orientation of the device relative to the body member; an arcuate array of light emitters around the device; wherein a selected subset of the light emitters are activated based on the orientation of the device relative to the body member; and an arcuate array of light receivers around the device which receives light beams emitted by the light emitters after light beams have been transmitted through or reflected by the body member. In an example, different emitters in an array can be activated to emit light based on different environmental parameters or conditions.

In an example, a first light emitter at a first location in an optical module (e.g. set) can emit (a pulse of) light at a first time and a second light emitter at a second location in the optical module (e.g. set) can emit (a pulse of) light at a second time. In an example, different optical modules (e.g. sets) can be activated to transmit pulses of light into a body member (e.g. finger, wrist, or arm) along different vectors at different times. In an example, a light emitter can emit a first pulse of light with a first duration followed by a second pulse of light with a second duration, wherein the second duration is greater than the first duration.

In an example, a biometric wearable device (e.g. finger ring or smart watch) can automatically vary the frequency, color, and/or spectrum of light from a light emitter to scan through a range of tissue depths, locations, and/or types in order to obtain more accurate measurement of a biometric parameter level. In an example, a biometric wearable device (e.g. finger ring or smart watch) can comprise an optical (e.g. spectroscopic) sensor which emits light at different frequencies at different times. In an example, a biometric wearable device (e.g. finger ring or smart watch) can have a light emitter which emits light with a first light wavelength (or wavelength range or spectral distribution) during a first time period and emits light with a second light wavelength (or wavelength range or spectral distribution) during a second time period.

In an embodiment, a frequency and/or spectrum of light emitted by a light emitter can be changed over time. In another example, a light emitter can emit a sequence of light pulses at different selected frequencies. In an example, a light emitter can emit light with a first light wavelength (or wavelength range or spectral distribution) during a first time period and can emit light with a second light wavelength (or wavelength range or spectral distribution) during a second time period in response to changing biometric parameter results. In another example, a light emitter can emit light with scanning variation in frequencies and/or wavelength. In another example, a light emitter of an optical (e.g. spectroscopic) sensor can emit light in a sequentially-varying range of wavelengths. In an example, a light emitter of an optical (e.g. spectroscopic) sensor can emit light with a wavelength which changes over time.

In an example, the color and/or spectrum of light from light emitters can be changed and/or adjusted to refine measurement of biometric parameter levels. In an example, the frequency, color, and/or spectrum of a light beam emitted from a light emitter can be changed in response to specific environmental conditions (e.g. temperature or humidity) and/or specific activities in which the person wearing a device is engaged (e.g. high level of movement, eating, sleeping, etc.). In an example, the frequency, color, and/or spectrum of light emitted from the light emitter can be adjusted automatically (in an iterative manner) by a device in order to more accurately measure body oxygenation, heart rate, heart rate variability, body hydration level, and/or blood glucose level for a specific person, for a specific type of activity, or for a specific configuration of the device relative to the person's body surface.

In a variation on this design, the frequency, color, and/or spectrum of light emitted from the light emitter can be adjusted in order to more accurately measure a biometric parameter level. In an example, the wavelength, color, and/or spectrum of light emitted by a light emitter can be automatically oscillated and/or iteratively-varied by the device in order to scan body tissue at different spectral wavelengths. In an embodiment, the wavelengths and/or frequencies of light from light emitters can be changed. In a variation on this design, there can be changes in the wavelength, color, and/or spectrum of light emitted by the same light emitter over time.

In an example, a biometric wearable device can comprise: a wearable device (e.g. finger ring or smart watch) worn around a body member (e.g. finger, wrist, and/or arm); light emitters which emit light beams power levels which change over time; and light receivers on the device which receive light beams emitted by the light emitters after the light beams have been transmitted through or reflected by the body member; and wherein a biometric parameter level is measured by changes in the spectra of the light beams. In an example, a light emitter can emit intensity-modulated and/or amplitude-modulated light. In an example, a spectroscopic sensor can further comprise one or more light emitters which emit light with time-varying intensity levels.

In an example, the power and/or intensity of a light beam emitted from a light emitter can be changed in response to specific environmental conditions (e.g. temperature or humidity) and/or specific activities in which the person wearing a device is engaged (e.g. high level of movement, eating, sleeping, etc.). In an example, the power and/or intensity of light emitted from the light emitter can be adjusted automatically to maintain accurate measurement of body oxygenation, heart rate, heart rate variability, body hydration level, and/or blood glucose level even if the device shifts and/or moves relative to the person's body surface. In another example, the power or intensity of a light beam emitted from a light emitter can be changed over time to create a chronological sequence of beams of light with different power or intensity levels. In an example, the coherence, polarization, and/or phase of light emitted from the light emitter can be adjusted.

In another example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the plurality of optical sensor sets collectively span at least two-thirds of the circumference of the body member; and wherein each optical sensor set further comprises: at least one red-light (e.g. infrared or visible red) emitter, at least one green-light emitter, at least one light receiver, at least one motion sensor, and at least one piezoelectric actuator which automatically adjusts the distance (or proximity or pressure) between the optical sensor set and the body member to maintain a selected distance (or proximity or pressure) between the optical sensor set and the body member if the device moves relative to the body member.

In an embodiment, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the plurality of optical sensor sets collectively span at least two-thirds of the circumference of the body member; and wherein each optical sensor set further comprises: at least one red-light (e.g. infrared or visible red) emitter, at least one green-light emitter, at least one light receiver, and at least one electromagnetic actuator which automatically adjusts the distance (or proximity or pressure) between the optical sensor set and the body member to maintain a selected distance (or proximity or pressure) between the optical sensor set and the body member if the device moves relative to the body member.

In another example, a light emitter can be automatically raised or lowered by an actuator. In another example, a light receiver can be automatically tilted, rotated, raised, or lowered in order to maintain a selected distance (or distance range) from the surface of a person's body. In an example, the distance and/or pressure from a light emitter relative to the person's body can be automatically oscillated and/or iteratively-varied by the device. In an example, varying the distance between a light receiver and one or more light emitters at different times can measure analyte concentration at different tissue levels and locations in a body member (e.g. finger, wrist, or arm).

In another example, a biometric wearable device (e.g. finger ring or smart watch) can further comprise a track, channel, or slot along which a light emitter, a light receiver, or both can be moved. In another example, a biometric wearable device can comprise: a wearable device (e.g. finger ring or smart watch) worn around a body member (e.g. finger, wrist, and/or arm); an actuator; a movable light emitter which is automatically moved in a clockwise (or counter clockwise) manner around (a portion of) the circumference of the wearable device by the actuator; at least one light receiver on the device which receives light beams emitted by a light emitter after the light beams have been transmitted through or reflected by the body member.

In an example, a biometric wearable device can comprise: a wearable device (e.g. finger ring or smart watch) worn around a body member (e.g. finger, wrist, and/or arm); an arcuate track, channel, or slot around (a portion of) the circumference of the wearable device; a light emitter which slides along the arcuate track, channel, or slot, wherein the light beams are directed toward the body member at a first angle at a first time and a second angle at a second time; wherein the second angle differs from the first angle by between 5 and 25 degrees; a light receiver on the device which receives light beams emitted by a light emitter after the light beams have been transmitted through or reflected by the body member. In an example, a distance between a light emitter and a light receiver can be adjusted by moving a light emitter, a light receiver, or both along a track, channel, or slot around the circumference of a device.

In an example, an electronic device worn on a person's finger (e.g. a finger ring) can comprise: one or more light emitters which direct light into a person's body; one or more light receivers which receive this light after it has been transmitted through or reflected by the person's body; and one or more actuators (e.g. electromagnetic, pneumatic, or hydraulic actuators), wherein the one or more actuators change the radial and/or circumferential locations of the light emitters on the device; and/or wherein the one or more actuators change the radial and/or circumferential locations of light receivers on the device. In an example, the circumferential (e.g. polar, compass, or clock-hour) location of a light emitter on the circumference of the body member (e.g. finger, wrist, or arm) can be automatically shifted and/or moved by the device. In an example, the geometric configuration of a plurality of light emitters and a light receiver can be adjusted automatically.

In an embodiment, a biometric wearable device (e.g. finger ring or smart watch) can comprise: a device worn around a body member (e.g. finger, wrist, and/or arm); a motion sensor (e.g. accelerometer and/or gyroscope); an arcuate array of light emitters around the wearable device, wherein parameters (e.g. intensity, frequency or color, projection vector) of light energy from the light emitters are selected at a given time based on data from the motion sensor at that time; and one or more light receivers which receive light beams from the light emitters after the light beams have been transmitted through or reflected by the body member.

In a variation on this design, this biometric wearable device (e.g. finger ring or smart watch) can comprise: a wearable device worn around a body member (e.g. finger, wrist, and/or arm); a motion sensor on the device; an arcuate array of light emitters around the wearable device, wherein the projection vectors of light beams emitted from the light emitters are changed based on data from the motion sensor; and one or more light receivers which receive light beams from the light emitters after the light beams have been transmitted through or reflected by the body member.

In an example, a biometric wearable device (e.g. finger ring or smart watch) can comprise: a wearable device worn around a body member (e.g. finger, wrist, and/or arm); a motion sensor; an actuator which decreases the cross-sectional perimeter of the device during times of greater motion; an arcuate array of light emitters around the device; and an arcuate array of light receivers around the device, wherein light receivers receive light beams from the light emitters after the light beams have been transmitted through or reflected by the body member.

In an example, this biometric wearable device (e.g. finger ring or smart watch) can comprise: a wearable worn around a body member (e.g. finger, wrist, and/or arm); a motion sensor; an arcuate array of light emitters, wherein different light emitters direct light beams toward the body along vectors which are automatically changed over time based on data from the motion sensor; and an arcuate array of light receivers which receive light beams from the light emitters after the light beams have been transmitted through or reflected by the body member. In an example, a device can further comprise one or more motion sensors, wherein a motion sensor can further comprise an accelerometer and/or gyroscope.

In an example, a biometric wearable device (e.g. finger ring or smart watch) can comprise: a plurality of body-facing (e.g. radially-inward) sensors (e.g. electromagnetic sensors or optical sensors) around the inner surface (e.g. inner circumference) of the device; and a plurality of actuators (e.g. electromagnetic, pneumatic, or hydraulic actuators) which adjust the angles between the sensors and the surface of the person's body. In another example, a biometric wearable device (e.g. finger ring or smart watch) can comprise light and electromagnetic energy sensors.

In an example, a biometric wearable device (e.g. finger ring or smart watch) can comprise: a device which is worn on a body member (e.g. finger, wrist, and/or arm); an (environmental) sensor selected from the group consisting of ambient light sensor, humidity sensor, motion sensor, pressure sensor, sound sensor, and temperature sensor; and a plurality of light emitters; wherein the power level, spectral frequency, or projection vector of light beams from the plurality of light emitters is adjusted (e.g. changed) based on data from the sensor. In another example, a biometric wearable device (e.g. finger ring or smart watch) can comprise: a wearable device worn around a body member (e.g. finger, wrist, and/or arm); an arcuate array of light emitters around the wearable device; an arcuate array of light receivers which receive light beams from the light emitters after the light beams have been transmitted through or reflected by the body member; and an accelerometer or altimeter.

In another example, a biometric wearable device (e.g. finger ring or smart watch) can comprise: a wearable device worn around a body member (e.g. finger, wrist, and/or arm); one or more sensors on the device selected from the group consisting of piezoelectric sensor, piezoresistive sensor, plethysmographic sensor, pressure sensor, and pulse sensor; an arcuate array of light emitters around the device, wherein the projection or incidence vectors of light beams emitted from the light emitters are changed based on data from the one or more sensors; and an arcuate array of light receivers around the device which receive light beams from the light emitters after the light beams have been transmitted through or reflected by the body member.

In an example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one orientation (and/or angle) sensor, and at least one microhydraulic (or micropneumatic) actuator which automatically moves the optical sensor set.

In another example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one orientation (and/or angle) sensor which measures the orientation (and/or angle) of the optical sensor set relative to the surface of the body member, and at least one microhydraulic (or micropneumatic) actuator which automatically adjusts the orientation (and/or angle) of the optical sensor set relative to the surface of the body member in response to data from the orientation (and/or angle) sensor.

In an embodiment, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one orientation (and/or angle) sensor which measures the orientation (and/or angle) of the optical sensor set relative to the surface of the body member, and at least one piezoelectric actuator which automatically adjusts the orientation (and/or angle) of the optical sensor set relative to the surface of the body member in response to data from the orientation (and/or angle) sensor.

In an example, a biometric wearable device (e.g. finger ring or smart watch) can comprise: an arcuate band (or ring) which is configured to be worn around a body member (e.g. finger, wrist, and/or arm); at least three optical sensor sets which are held in proximity to the body member, wherein the optical sensor sets collectively span at least two-thirds of the circumference of the body member, and wherein each optical sensor set further comprises at least one red-light (e.g. infrared or visible red) emitter, at least one green-light emitter, and at least one light receiver, at least one orientation (and/or angle) sensor, and at least one microhydraulic (or micropneumatic) actuator which moves the optical set relative to the rest of the arcuate band (or ring) in response to data from the orientation (and/or angle) sensor. In an example, a biometric wearable device (e.g. finger ring or smart watch) can further comprise one or more sensors selected from the group consisting of: electrical resistance sensor, skin moisture sensor, accelerometer, neurosensor, blood pressure sensor, piezocapacitive sensor, electromagnetic resistance sensor, and stretch sensor.

In an example, a biometric wearable device can comprise: a wearable device (e.g. finger ring or smart watch) worn around a body member (e.g. finger, wrist, and/or arm); a motion and/or orientation sensor; a light emitter which emits light beams directed toward the body member at either a first angle or a second angle, depending on the motion and/or orientation of the device as detected by the motion and/or orientation sensor; and a light receiver on the device which receives light beams emitted by a light emitter after the light beams have been transmitted through or reflected by the body member. In an example, a device or system can further comprise one or more sensors selected from the group consisting of: camera, piezoelectric sensor, chemiluminescence sensor, pressure sensor, magnetic field sensor, ballistocardiographic sensor, pH level sensor, and inclinometer.

In a variation on this design, a device or system can further comprise one or more sensors selected from the group consisting of: ultrasonic sensor, Hall-effect sensor, variable impedance sensor, humidity sensor, variable resistance sensor, motion sensor, microphone, conductivity sensor, and skin conductance sensor. In an example, a shape of a sensor can be adjusted each time a person wears the device in order to calibrate it for differences in placement or other variables from one wearing to the next. In an example, a shape of a sensor can be automatically adjusted based on one or more parameters selected from the group consisting of: changes in the location on a person's body on which they are worn; changes their distance from the surface of the person's body; changes in the pressure and/or force which they apply to the person's body; changes in their angle and/or orientation relative to the person's body; changes in body temperature and/or ambient temperature; changes in body moisture level and/or ambient humidity; and body motion and/or speed. In an embodiment, an angle and/or vector of a light beam which has been emitted from a light emitter can be automatically changed by the device based on data from the one or more distance and/or pressure sensors.

In an example, a biometric wearable device (e.g. finger ring or smart watch) can comprise: (a) a housing (e.g. finger ring or smart watch housing) which is worn on a body member (e.g. finger, wrist, or arm); an array of light emitting optical modules (e.g. sets) and light receivers on the housing; wherein light emitted from the light emitters is transmitted through or reflected by the person's body tissue and received by the light receivers; wherein attributes (e.g. the spectral distribution) of light received by the light receivers are analyzed to measure one or more biometric parameters and/or detect one more physiological conditions of the person; wherein the array has a circular, approximately-circular polygonal (e.g. hexagonal or octagonal), annular, or circumferential shape; wherein there is an alternating pattern of light emitting optical modules and light receivers around the perimeter of the array; wherein there are a plurality (e.g. three or more) of light emitters in each light emitter module;

wherein different light emitters in an optical module emit light with different colors, wavelengths, and/or frequencies; and wherein at least one light emitter in an optical module emits red light, at least one light emitter in an optical module emits infrared light, and at least one light emitter in an optical module emits green light; and (b) one or more circular, annular, and/or circumferential opaque light barriers surrounding one or more light receivers; wherein the one or more light barriers reduce or eliminate transmission of light from the light emitters to the light receivers which has not been reflected by or transmitted through the person's body tissue; and/or wherein the one or more light barriers reduce or eliminate transmission of ambient light to the light emitters.

In another example, a biometric wearable device (e.g. finger ring or smart watch) can include a circular, annular, circumferential, and/or polygonal light barrier between light emitters in the device and light receivers in the device so that light from light emitters only reaches light receivers after it has been reflected by or transmitted through body tissue. In an example, a biometric wearable device (e.g. finger ring or smart watch) can include a plurality of light barriers and a plurality of light receivers, wherein there is one light barrier surrounding each light receiver. In another example, a biometric wearable device (e.g. finger ring or smart watch) can include two circular, annular, circumferential, and/or polygonal light barriers: one light barrier between light emitters in the device and light receivers in the device; and one light barrier between ambient light and light receivers in the device. In another example, a device can further comprise one or more opaque light barriers surrounding one or more light receivers.

In an example, a light barrier between a light emitter and a light receiver can be opaque. In another example, a light barrier can be made from an opaque compressible polymer. In an example, a light barrier can be made from an opaque material. In an example, a light barrier can comprise a circular and/or annular opaque ring between a light emitter and a light receiver (or module or set of light receivers). In an example, a light barrier can comprise a polygon (e.g. quadrilateral, hexagon, or octagon shaped member) of compressible, compliant, and/or elastomeric opaque material between a light emitter and a light receiver (or module or set of light receivers). In an example, a light barrier can comprise a polygon (e.g. quadrilateral, hexagon, or octagon shaped member) of opaque material between ambient light and a light receiver (or module or set of light receivers).

In an embodiment, a light barrier can comprise a ring of compressible, compliant, and/or elastomeric opaque material between a light emitter and a light receiver (or module or set of light receivers). In an example, a light barrier can comprise a ring of opaque material between a light emitter and a light receiver (or module or set of light receivers). In an example, a light barrier can comprise compressible foam. In a variation on this design, a light barrier can form a perimeter around a light receiver. In an example, a light barrier can have a linear shape. In an example, a light barrier can have a polygonal (e.g. square, hexagonal, or octagonal) shape. In another example, a light barrier can surround a perimeter around a light single receiver.

In an example, a light receiver can be optically isolated by a light barrier, shield, blocker, and/or cladding so that only light which reaches light receiver has been reflected from or transmitted through body tissue, organs, and/or fluid. In another example, all light receivers in a wearable device can be optically isolated from direct transmission (e.g. not through body tissue) of light from one or more light emitters by the same light barrier. In an example, each light receiver in a wearable device can be optically isolated from ambient light by a circular and/or annular light barrier. In another example, each light receiver in a wearable device can be optically isolated from direct transmission (e.g. not through body tissue) of light from one or more light emitters by a separate light barrier.

In an embodiment, one or more light barriers (e.g. light shields, light blockers, cladding, and/or opaque barriers) can reduce or eliminate such errors. In an example, the light barriers can reduce or eliminate transmission of light from the light emitters to the light receivers which has not been reflected by or transmitted through the person's body tissue. In an example, there can be a light barrier around each light emitter in a wearable device. In an example, there can be one light barrier which encircles all light emitters in a wearable device. In an example, this biometric wearable device (e.g. finger ring or smart watch) can one or more expandable (e.g. hydraulic, pneumatic, or inflatable) chambers which adjust the fit of the device on a body member (e.g. finger, wrist, or arm).

In an example, a biometric wearable device can comprise: a ring which is configured to be worn around a person's finger, wherein the ring has a plurality of radial undulations; and at least three optical sensor sets which are held in proximity to the person's finger, wherein the optical sensor sets are located on portions of the ring which protrude toward the surface of the person's finger, wherein each optical sensor set further comprises at least one red-light (e.g. infrared or visible red) emitter, at least one green-light emitter, at least one light receiver. In an example, this biometric wearable device can comprise: a ring which is worn on a person's finger; and at least three optical sensors, wherein the optical sensors are on portions of the ring with protrusions toward the surface of the person's finger, and wherein an optical sensor has an infrared light emitter, a red light emitter, a green-light emitter, or a light receiver. In another example, a biometric wearable device can comprise: a ring which is worn on a person's finger; inward-facing protrusions on portions of the ring; and light emitters on the portions of the ring with protrusions, wherein the light emitters include an infrared light emitter, a red light emitter, and a green-light emitter.

In an example, a biometric wearable device can comprise: a wearable device (e.g. finger ring or smart watch) worn on a body member (e.g. finger, wrist, and/or arm); a first plurality of segments or housings on the circumference of the wearable device, wherein the first plurality has a first elasticity level; a second plurality of segments or housings on the circumference of the wearable device, wherein the second plurality has a second elasticity level, wherein the second elasticity level is less than the first elasticity level; a plurality of light emitters and light receivers on the second plurality, wherein light receivers receive light beams from the light emitters after the light beams have been transmitted through or reflected by the body member.

In another example, a first portion of a biometric wearable device (e.g. finger ring or smart watch) can have a first elasticity level and a second portion of the device can have a second elasticity level, wherein the second level is greater than the first level, and wherein optical modules (e.g. sets) (e.g. light emitters and receivers) are located on the first portion. In an embodiment, a first portion of a biometric wearable device (e.g. finger ring or smart watch) can have a first level of stretchability and a second portion of the device can have a second level of stretchability, wherein the second level is greater than the first level, and wherein optical modules (e.g. sets) (e.g. light emitters and receivers) are located on the second portion. In another example, a first portion of the circumference of a biometric wearable device (e.g. finger ring or smart watch) can have a first elasticity level and a second portion of the circumference of the device can have a second elasticity level, wherein the second level is greater than the first level, and wherein the first portion is smaller than the second portion.

In an example, a first portion of the circumference of a biometric wearable device (e.g. finger ring or smart watch) can have a first level of stretchability and a second portion of the circumference of the device can have a second level of stretchability, wherein the second level is greater than the first level, and wherein the first portion is larger than the second portion. In an example, a first portion of the circumference of a biometric wearable device (e.g. finger ring or smart watch) can have a first elasticity level and a second portion of the circumference of the device can have a second elasticity level, wherein the second level is greater than the first level, and wherein the first portion is between 60% and 80% of the circumference of the device.

In a variation on this design, a biometric wearable device (e.g. finger ring or smart watch) can include a local data processor. In an example, the device can further comprise a data processor. In an example, a biometric wearable device (e.g. finger ring or smart watch) can further comprise a local data processer which is in wireless electronic communication with a remote data processor. In an example, a biometric wearable device (e.g. finger ring or smart watch) can be part of a system that includes data transmitter which is in electronic communication with a remote data processor. In an example, a device or system can further comprise a cell phone and/or mobile phone.

In an embodiment, a battery or other energy source can power one or more light emitters in a device. In another example, a biometric wearable device (e.g. finger ring or smart watch) can include a battery or other energy source. In an example, an energy source can transduce, harvest, and/or generate energy from ambient (e.g. solar) light. In another example, an energy source can transduce, harvest, and/or generate energy from body thermal energy.

In another example, a biometric wearable device (e.g. finger ring or smart watch) can further comprise one or more optical filters or lenses which change the coherence, polarization, and/or phase of light emitted by a light emitter. In an example, a device or system can further comprise a camera. In an example, a device or system can further include a computer-to-human interface which is selected from the group consisting of: auditory feedback (such as a voice message, alarm, buzzer, ring tone, or song); feedback via computer-generated speech; mild external electric charge or neural stimulation; periodic feedback at a selected time of the day or week; phantom taste or smell; phone call; pre-recorded audio or video message by the person from an earlier time; television-based messages; and tactile, vibratory, or pressure-based feedback.

In an example, a device for measuring one or more biometric parameters can have a plurality of light emitters which are selected from group consisting of: Light Emitting Diode (LED), Organic Light Emitting Diode (OLED), Laser Diode (LD), Superluminescent Light Emitting Diode (SLED), Resonant Cavity Light Emitting Diode (RCLED), coherent light source, infrared (IR) light emitter, laser, low-power laser, microplasma light emitter, multi-wavelength source, Quasi Monochromatic (QM) light, and Ultra Violet (UV) light emitter. In an example, data from a biometric wearable device (e.g. finger ring or smart watch) can be analyzed using Near-Infrared Spectroscopy (NIRS) to measure a biometric parameter level in a body member (e.g. finger, wrist, or arm). In an example, data from a biometric wearable device (e.g. finger ring or smart watch) can be analyzed using Time Domain (TD) optical analysis to measure a biometric parameter level in a body member (e.g. finger, wrist, or arm).

In another example, data from a biometric wearable device (e.g. finger ring or smart watch) can be analyzed using Continuous Wave (CW) optical analysis. In an example, data from a light receiver can be analyzed to measure a biometric parameter level using one or more methods selected from the group consisting of: Decision Tree Analysis (DTA), Discrete Fourier transform (DFT), Discriminant Analysis (DA), Empirical Mode Decomposition (EMD), Factor Analysis (FA), Fast Fourier Transform (FFT), Feature Vector Analysis (FVA), and Fisher Linear Discriminant. In another example, data from a light receiver can be analyzed to measure a biometric parameter level using one or more methods selected from the group consisting of: Machine Learning (ML), Markov Model, Maximum Entropy Modeling, Maximum Likelihood, Mean Power, Multi-Band Covariance Analysis, Multi-Channel Covariance Analysis, Multivariate Linear Regression, Multivariate Logit, Multivariate Regression, Naive Bayes Classifier, Neural Network, Non-Linear Programming, and Non-negative Matrix Factorization (NMF).

In an example, a device with light emitters and light receivers for measuring a biometric parameter can be embodied in a sleeve or cuff of a shirt (or other upper body garment). In a variation on this design, the biometric parameter level which is measured and/or monitored by a biometric wearable device (e.g. finger ring or smart watch) can be (blood) glucose level. In another example, the biometric parameter level which is measured and/or monitored by a biometric wearable device (e.g. finger ring or smart watch) can be body hydration level. In an example, the biometric parameter level which is measured and/or monitored by a biometric wearable device (e.g. finger ring or smart watch) can be lactic acid level. In another example, the biometric parameter level which is measured and/or monitored by a biometric wearable device (e.g. finger ring or smart watch) can be.

In an example, a light emitter can be a laser. In an embodiment, a light emitter can be a Light Emitting Diode (LED). In an example, a light emitter can be a Monochromatic LED (MLED). In an embodiment, a light emitter can be a Phosphorescent OLED (PHOLED). In an example, a light emitter can be a Side-Emitting polymer Optical Fiber (SEPOF). In an embodiment, a light emitter can be a tunable LED. In an example, a light emitter can be an Organic Light Emitting Diode (OLED). In another example, a light emitter can emit white light and/or be a white-light laser. In an example, a light receiver can be an avalanche photo diode (APDs) or PIN photodiode. In another example, one or more light emitters in a biometric wearable device (e.g. finger ring or smart watch) can be infrared light emitters.

In an example, a first light emitter can emit light with a first light coherence, polarization, and/or phase and a second light emitter can emit light with a second light coherence, polarization, and/or phase. In another example, a light emitter can emit polarized light. In an example, a first light emitter in a wearable device (e.g. finger ring or smart watch) can emit infrared light and a second light emitter in the device can emit green light. In an example, a light emitter can be a red-light laser. In an example, a light emitter can emit visible light. In a variation on this design, an optical (e.g. spectroscopic) sensor of a wearable device can comprise a light emitter which emits infrared light. In an embodiment, one light emitter in a device can emit red light, a second light emitter in a device can emit infrared light, and a third light emitter in a device can emit green light. In an example, one or more light emitters in a device can be a red LED. In an example, one or more light emitters in a device can emit infrared light.

In another example, a biometric wearable device (e.g. finger ring or smart watch) can have a plurality of light emitter optical modules (e.g. sets), wherein each module includes three light emitters which emit light in three different colors, wavelengths, and/or frequencies, respectively. In an example, a biometric wearable device (e.g. finger ring or smart watch) can comprise an array of optical modules (e.g. sets) of red, infrared, and green light emitters and light receivers on the body-facing side of the housing of the device. In another example, a biometric wearable device (e.g. finger ring or smart watch) can comprise an array of red, infrared, and green light emitters and light receivers on the body-facing side of the housing of the device.

In another example, a biometric wearable device (e.g. finger ring or smart watch) can comprise at least two light emitters which emit light of different colors, respectively. In an example, a biometric wearable device (e.g. finger ring or smart watch) can comprise: a device which is configured to be worn around a body member (e.g. finger, wrist, and/or arm), wherein the device spans at least two-thirds of the circumference of the body member; and at least six optical sensor sets which are held in proximity to the body member by the device, wherein the optical sensor sets collectively span at least two-thirds of the circumference of the body member, and wherein each optical sensor set further comprises at least one red-light (e.g. infrared or visible red) emitter, at least one green-light emitter, at least one light receiver, and at least one electromagnetic actuator which automatically adjusts the distance and/or motion, orientation, and/or angle of the optical sensor set relative to the surface of the body member.

In an example, a biometric wearable device (e.g. finger ring or smart watch) can comprise: a device which is configured to be worn around a body member (e.g. finger, wrist, and/or arm), wherein the device spans at least two-thirds of the circumference of the body member; and at least eight optical sensor sets which are held in proximity to the body member by the device, wherein the optical sensor sets collectively span at least two-thirds of the circumference of the body member, and wherein each optical sensor set further comprises at least one red-light (e.g. infrared or visible red) emitter, at least one green-light emitter, and at least one light receiver.

In an example, this biometric wearable device (e.g. finger ring or smart watch) can comprise: a finger ring which is configured to be worn around a person's finger, wherein the finger ring spans the circumference of the person's finger; and at least six optical sensor sets which are held in proximity to the person's finger by the finger ring, wherein the optical sensor sets collectively span the circumference of the person's finger, and wherein each optical sensor set further comprises at least one red-light (e.g. infrared or visible red) emitter, at least one green-light emitter, at least one light receiver, and at least one electromagnetic actuator which automatically adjusts the distance and/or motion, orientation, and/or angle of the optical sensor set relative to the surface of the person's finger.

In an example, a biometric wearable device (e.g. finger ring or smart watch) can comprise: a finger ring which is configured to be worn around a person's finger, wherein the ring spans at least two-thirds of the circumference of the person's finger, wherein the ring has a plurality of radial undulations; and at least three optical sensor sets which are held in proximity to the person's finger, wherein the optical sensor sets are located on portions of the band (or ring) which protrude toward the surface of the person's finger, wherein the optical sensor sets collectively span at least two-thirds of the circumference of the person's finger, wherein each optical sensor set further comprises at least one red-light (e.g. infrared or visible red) emitter, at least one green-light emitter, at least one light receiver.

In an embodiment, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, and at least one microhydraulic (or micropneumatic) actuator which automatically adjusts the orientation (and/or angle) of the optical sensor set relative to the surface of the body member to maintain a selected orientation (and/or angle) between the optical sensor set and the body member if the device moves relative to the body member.

In an example, this biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member, and wherein each optical sensor set further comprises at least one red-light (e.g. infrared or visible red) emitter, at least one green-light emitter, at least one light receiver, and at least one wavelength tuner which automatically modifies which wavelengths of light from the light emitters reach the body member. In an example, a biometric wearable device (e.g. finger ring or smart watch) can comprise: at least three optical sensor sets which are held in proximity to the body member, wherein the optical sensor sets collectively span at least two-thirds of the circumference of the body member, and wherein each optical sensor set further comprises at least one red-light (e.g. infrared or visible red) emitter, at least one green-light emitter, and at least one light receiver.

In another example, a device with two light emitters which emit light with two different colors and/or wavelengths can be used to measure a person's blood and/or tissue oxygenation level. In an example, a first light emitter can emit light with a first light frequency, color, and/or spectrum and a second light emitter can emit light with a second light frequency, color, and/or spectrum. In another example, a first light emitter can emit light with a wavelength in the range of 600 to 900 nm; a second light emitter can emit light with a wavelength in the range of 900 nm to 1200 nm; and a third light emitter can emit light with a wavelength in the range of 1200 nm to 1500 nm. In an example, a first light emitter can emit near-infrared light and a second light emitter can emit green light.

In another example, a first light emitter which emits light in a first color can emit light with a first intensity or power level and a second light emitter which emits light in a second color can emit light with a second intensity or power level. In a variation on this design, a light emitter of an optical (e.g.

spectroscopic) sensor can emit light in a sweeping series of wavelengths. In an example, a wearable device (e.g. finger ring or smart watch) can comprise: a first light emitter which emits light at a wavelength in the range of 400 nm to 600 nm; and a second light emitter which emits light at a wavelength in the range of 780 nm to 900 nm. In an example, at least one light emitter in an optical module (e.g. set) can emit red light, at least one light emitter in the optical module can emit infrared or near-infrared light, and at least one light emitter in the optical module can emit green light. In an embodiment, different light emitters in an optical module (e.g. set) can emit light at different frequencies. In an example, there can be alternation between two light wavelengths and/or colors in an arcuate array of light emitters around (at least half of) the circumference of a body member (e.g. finger, wrist, or arm).

In another example, a biometric wearable device (e.g. finger ring or smart watch) can comprise an array, grid, and/or matrix of light emitters which differ in one or more parameters selected from the group consisting of: location and/or distance from a light receiver; distance to body surface; light beam frequency, color, and/or spectrum; light beam coherence, polarity, and/or phase; light beam power and/or intensity; light beam projection and/or body incidence angle; light beam duration; light beam size; and light beam focal distance. In an example, a light receiver can be a photodetector which absorbs photons and generates electrical current, thereby converting light to electricity. In an example, a light receiver can be a photoreceptor. In another example, a light receiver can be an organic phototransistor. In another example, a light receiver can have an organic photoactive channel layer, a dielectric layer, and electrodes.

In an example, a biometric wearable device (e.g. finger ring or smart watch) can comprise one or more spectroscopic sensors selected from the group consisting of: near-infrared spectroscopic sensor; infrared spectroscopic sensor; white light spectroscopic sensor; and ultraviolet spectroscopic sensor. In an example, a biometric wearable device (e.g. finger ring or smart watch) can comprise: (a) an attachment member, such as a strap or band, which is configured to span at least a portion of the circumference of a body member (e.g. finger, wrist, and/or arm); (b) an enclosure which is part of (or attached to) the attachment member; and (c) a rotating light-projecting spectroscopic (e.g. optical) sensor, wherein this sensor can be rotated relative to the enclosure and wherein rotation of this sensor relative to the enclosure changes the angle at which the sensor projects light onto the surface of the body member.

In another example, a biometric wearable device (e.g. finger ring or smart watch) can comprise: an arcuate wearable device with a rotating light-projecting spectroscopic (e.g. optical) sensor, wherein rotation of this sensor changes the angle at which it projects light onto the surface of a body member (e.g. finger, wrist, and/or arm). In another example, a device which uses spectroscopic analysis to measure one or more biometric parameters can include a digital micromirror device in addition to light emitters and light receivers. In an example, a spectroscopic (e.g. optical) sensor can be rotated relative to the rest of a ring. In another example, a spectroscopic sensor can be selected from the group consisting of: spectroscopic sensor, spectrometry sensor, white light spectroscopic sensor, infrared spectroscopic sensor, near-infrared spectroscopic sensor, ultraviolet spectroscopic sensor, ion mobility spectroscopic sensor, mass spectrometry sensor, backscattering spectrometry sensor, and spectrophotometer.

In an example, a spectroscopic sensor can further comprise one or more light emitters which emit light at different wavelengths at different times. In another example, an optical (e.g. spectroscopic) sensor can comprise a circular or annular array with at least one light emitter and at least one light receiver. In an embodiment, an optical (e.g. spectroscopic) sensor can comprise a plurality of light emitters in a ring or circle around a light receiver. In an example, an optical (e.g. spectroscopic) sensor can comprise a ring of light emitters and receivers. In an example, an optical (e.g. spectroscopic) sensor can comprise two light emitters and one light receiver. In an example, changes in the intensity (e.g. amplitude) of light emitted from light emitters and received by light receivers which are caused by transmission of the light through a body member (e.g. finger, wrist, or arm) can be analyzed to measure and/or monitor a biometric parameter level.

In an example, changes in the spectrum (e.g. spectral distribution) of light emitted from light emitters and received by light receivers which are caused by transmission of the light through a body member (e.g. finger, wrist, or arm) can be analyzed to measure and/or monitor a biometric parameter level. In a variation on this design, having a rotating light-projecting spectroscopic (e.g. optical) sensor can enable a device to record spectroscopic measurements with substantially the same angle of incidence, even if it is tilted with respect to the surface of a body member (e.g. finger, wrist, and/or arm). In an example, optical (e.g. spectroscopic) sensors can be clustered on ventral and/or dorsal portions of the circumference of a wearable device.

In an example, a light emitter can emit light which is transmitted through or reflected by a body member (e.g. finger, wrist, or arm). In an embodiment, light emitters can be located on a first side of a biometric wearable device (e.g. finger ring or smart watch) and light receivers can be located on a second side (e.g. opposite the first side) of the device. In an example, light emitters can be closer together in the dorsal-right quadrant of a biometric wearable device (e.g. finger ring or smart watch). In another example, optical modules (e.g. sets) in an dorsal-right quadrant of a biometric wearable device (e.g. finger ring or smart watch) can be closer together than those in an dorsal-left quadrant of the device. In another example, there can be more optical modules (e.g. sets) in an dorsal-right quadrant of a biometric wearable device (e.g. finger ring or smart watch) than in the dorsal-left quadrant of the device.

In another example, a biometric wearable device (e.g. finger ring or smart watch) can comprise an annular and/or circular array of light emitters and light receivers on the body-facing side of the housing of a wearable device. In another example, a biometric wearable device (e.g. finger ring or smart watch) can have two or more circumferential or annular arrays of light emitters and light receivers around circumferential axes which are parallel to each other. In an example, light emitters and receivers in a biometric wearable device (e.g. finger ring or smart watch) can span the entire perimeter of the device. In an example, light emitters can be positioned on a common circumferential line. In an example, optical modules (e.g. sets) of light emitters can be positioned on a common line around the circumference of a device.

In another example, a biometric wearable device (e.g. finger ring or smart watch) can comprise: a finger ring; and a convex array of light emitters and light receivers around the inner (body-facing) circumference of the finger ring; wherein light receivers receive the light beams from the light emitters after the light beams have been transmitted through or reflected by the finger. In another example, a biometric wearable device (e.g. finger ring or smart watch) can comprise: a wearable device worn around a body member (e.g. finger, wrist, and/or arm); a convex array of light emitters and light receivers around the circumference of the wearable device; a convex array of beamsplitters around the circumference of the wearable device; wherein light receivers receive light beams emitted by the light emitters after the light beams have been passed through the beamsplitters and been transmitted through or reflected by the body member.

In another example, a biometric wearable device can comprise: a wearable device (e.g. finger ring or smart watch) worn around a body member (e.g. finger, wrist, and/or arm); and an annular array of light emitters and light receivers around the inner circumference of the device; wherein light receivers receive the light beams from the light emitters after the light beams have been transmitted through or reflected by the body member; and wherein a biometric parameter level is measured by changes in the spectra of the light beams. In an example, a subset of light emitters in a circumferential array of light emitters can be two or more circumferentially-proximal light emitters with different polar coordinates.

In an example, having an arcuate array of light emitters and light receivers around the circumference of a body member (e.g. finger, wrist, and/or arm) can ensure that at least some of the light emitters and light receivers are in close optical communication with the surface of the body member at any given time even if the device shifts and/or rotates relative to the body member. In an example, optical (e.g. spectroscopic) sensors can be evenly distributed along different locations around the circumference of a wearable device. In another example, proximal pairs of light receivers in a circumferential array can have polar coordinates which differ by 15, 30, 40, 60, or 90 degrees. In an embodiment, proximal pairs of optical modules (e.g. sets) of light emitters in a circumferential array can have polar coordinates which differ by 40 degrees.

In another example, a biometric wearable device (e.g. finger ring or smart watch) can comprise a first module (e.g. set) of light emitters of a first type and a second first module (e.g. set) of light emitters of a second type, wherein the first and second types of light emitters differ from each other by one or more characteristics selected from the group consisting of: light beam color and/or spectral frequency; light beam intensity and/or power; size and/or shape; angle of light beam projection; light coherence; and light polarity. In an example, a biometric wearable device (e.g. finger ring or smart watch) can comprise: a device worn around a body member (e.g. finger, wrist, and/or arm); a light emitter with an automatically-moving reflective component whose light beams are directed toward the body member at a first angle at a first time and at a second angle at a second time; wherein the second angle differs from the first angle by between 1 and 90 degrees; and a light receiver on the device which receives light beams emitted by a light emitter after the light beams have been transmitted through or reflected by the body member.

In another example, a biometric wearable device (e.g. finger ring or smart watch) can comprise: a wearable device worn on a body member (e.g. finger, wrist, and/or arm); light emitters around the wearable device, wherein the vectors along which light beams are emitted from the light emitters are automatically changed over time to create a chronological sequence of light beams with different projection and/or body incidence angles; and light receivers which receive light beams from the light emitters after the light beams have been transmitted through or reflected by the body member.

In an example, a biometric wearable device can comprise: a wearable device (e.g. finger ring or smart watch) worn around a body member (e.g. finger, wrist, and/or arm); a convex array of light emitters around the wearable device; a convex array of rotating microlenses around the wearable device, wherein the microlenses change the incidence angles at which light beams from the light emitters reach the surface of the body member; a convex array of light receivers around the wearable device which receive light beams from the light emitters after the light beams have passed through the microlenses and been transmitted through or reflected by the body member.

In another example, a biometric wearable device can comprise: a wearable device (e.g. finger ring or smart watch) worn around a body member (e.g. finger, wrist, and/or arm); an array of light emitters on the device which emit light beams at different angles relative to radial vectors extending outward from the cross-sectional center of the body member; and an array of light receivers which receive light beams from the light emitters after the light beams have been transmitted through or reflected by the body member. In a variation on this design, a first light emitter can emit light along a first angle and/or vector and a second light emitter can emit light along a second angle and/or vector. In an example, a first light emitter can emit light with a first light projection and/or body incidence angle and a second light emitter can emit light with a second light projection and/or body incidence angle.

In a variation on this design, an angle of a light beam emitted from a light energy emitter can be changed over time to create a chronological sequence of beams of light with different projection and/or body incidence angles. In an example, different light emitters can emit light toward a person's body at different angles with respect to a proximal surface of a person's body. In an example, light beams can be transmitted through or reflected by a body member (e.g. finger, wrist, or arm) along multiple vectors between pairs of light emitters and light receivers at different locations around the perimeter of a biometric wearable device (e.g. finger ring or smart watch). In an embodiment, the first light emitter can emit light at a first angle with respect to the surface of a person's body and the second light emitter can emit light at a second angle with respect to the surface of a person's body.

In an example, a biometric wearable device (e.g. finger ring or smart watch) can comprise an array, grid, and/or matrix of light receivers which differ in: location and/or distance from a light emitter; and/or distance to body surface. In an example, a biometric wearable device (e.g. finger ring or smart watch) can have an array, matrix, or grid of four or more light emitters, each of which is separated from the nearest other light emitter by a distance within the range of 2 mm to 5 cm. In an example, there can be a constant distance between (proximal or adjacent) optical modules (e.g. sets) of light emitters in an array and/or configuration of optical modules of light emitters. In another example, there can be a first distance and/or pressure between a first light emitter in the array and a person's body surface and a second distance and/or pressure between a second light emitter in the array and the person's body surface.

In an example, a biometric wearable device (e.g. finger ring or smart watch) can further comprise an alternating sequence of light emitters and light receivers around a cross-sectional perimeter of the device. In another example, a biometric wearable device (e.g. finger ring or smart watch) can further comprise a repeating (e.g. e1-e2-r) sequence of light emitters and light receivers around (a portion of) the perimeter of the device, wherein (e1) is a near-infrared light emitter, (e2) is a visible light emitter, and (r) is a light receiver. In another example, a biometric wearable device (e.g. finger ring or smart watch) can further comprise a repeating (e.g. e-r) sequence of light emitters and light receivers around (a portion of) the perimeter of the device, wherein (e) is a light emitter and (r) is a light receiver. In an example, there can be a repeating sequence of two different light wavelengths and/or colors in an arcuate array of light emitters around (at least half of) the circumference of a body member (e.g. finger, wrist, or arm).

In an example, this biometric wearable device (e.g. finger ring or smart watch) can comprise: a housing (e.g. finger ring or smart watch housing) which is worn on a body member (e.g. finger, wrist, or arm); an array of light emitting optical modules (e.g. sets) and light receivers on the housing; wherein light emitted from the light emitters is transmitted through or reflected by the person's body tissue and received by the light receivers; wherein attributes (e.g. the spectral distribution) of light received by the light receivers are analyzed to measure one or more biometric parameters and/or detect one more physiological conditions of the person; wherein the array has a circular, approximately-circular polygonal (e.g. hexagonal or octagonal), annular, or circumferential shape; wherein there is an alternating pattern of light emitting optical modules and light receivers around the perimeter of the array; wherein there are a plurality (e.g. three or more) of light emitters in each light emitter module; wherein different light emitters in an optical module emit light with different colors, wavelengths, and/or frequencies; and wherein at least one light emitter in an optical module emits red light, at least one light emitter in an optical module emits infrared light, and at least one light emitter in an optical module emits green light.

In an example, a biometric wearable device (e.g. finger ring or smart watch) can comprise a circular, annular, and/or octagonal array of alternating light emitters and light receivers. In an example, this biometric wearable device (e.g. finger ring or smart watch) can comprise a three-dimensional stacked array, grid, and/or matrix of alternating light emitters and receivers. In an embodiment, a biometric wearable device (e.g. finger ring or smart watch) can comprise an approximately-circular (polygonal, such as quadrilateral, hexagonal, or octagonal) alternating (e.g. emitter then receiver) array of light emitters and light receivers on the body-facing surface of the circumference of the device. In an example, there can be an alternating pattern of light emitting optical modules (e.g. sets) and light receivers in the array.

In an example, an array of light emitters and light receivers can have a conic section shape. In a variation on this design, an array of light emitters and light receivers can have a hexagonal shape. In an embodiment, an array of light emitters and light receivers can have a sunburst (e.g. radial spoke) shape. In an example, a biometric wearable device (e.g. finger ring or smart watch) can comprise a plurality of optical modules (e.g. modules or sets having light emitters and light receivers), wherein each module forms a vertex of a hexagon. In another example, a biometric wearable device (e.g. finger ring or smart watch) can comprise an approximately-circular (polygonal, such as quadrilateral, hexagonal, or octagonal) array of light emitters and light receivers on the body-facing side of the housing of the wearable device.

In an embodiment, a plurality of light emitters can be configured in a polygonal array around a light receiver. In another example, a plurality of light receivers can be configured in a circular or other arcuate array around a light emitter. In an example, a plurality of light receivers can be configured in a polygonal array in proximity to a light emitter. In another example, a sensor can comprise a polygonal array with at least one light emitter and at least one light receiver. In an example, light emitters can be arranged in an (approximately-circular) polygonal array around the central light receiver. In an example, light emitters can be configured in a polygonal array and/or configuration. In an example, light receivers can be configured in a hexagonal or octagonal array and/or configuration. In an example, optical modules (e.g. sets) of light emitters can be configured in a hexagonal or octagonal array and/or configuration. In an example, the array can be a hexagonal or octagonal array.

In an example, a biometric wearable device (e.g. finger ring or smart watch) can comprise a checkerboard array, grid, and/or matrix of light emitters and light receivers. In an example, a biometric wearable device (e.g. finger ring or smart watch) can comprise a rectangular array, grid, and/or matrix of light emitters and light receivers. In an example, a biometric wearable device (e.g. finger ring or smart watch) can have an array, matrix, or grid of light emitters and light receivers.

In an example, a biometric wearable device (e.g. finger ring or smart watch) can comprise: a wearable device worn on a body member (e.g. finger, wrist, and/or arm); light emitters whose light beams are directed toward the body member along different incidence vectors at different times; and light receivers which receive light beams emitted by a light emitter after the light beams have been transmitted through or reflected by the body member. In an embodiment, a biometric wearable device can comprise: a wearable device (e.g. finger ring or smart watch) worn around a body member (e.g. finger, wrist, and/or arm); a light emitter on the device which emits light beams directed toward the body member at a first angle at a first time and at a second angle at a second time; wherein the second angle differs from the first angle by between 1 and 10 degrees; a light receiver on the device which receives light beams emitted by a light emitter after the light beams have been transmitted through or reflected by the body member In a variation on this design, a biometric wearable device can comprise: a wearable device (e.g. finger ring or smart watch) worn around a body member (e.g. finger, wrist, and/or arm); an automatically-rotating light emitter on the device whose light beams are directed toward the body member at a first projection angle at a first time and a second projection angle at a second time; a light receiver on the device which receives light beams emitted by a light emitter after the light beams have been transmitted through or reflected by the body member. In another example, a biometric wearable device can comprise: a wearable device (e.g. finger ring or smart watch) worn on a body member (e.g. finger, wrist, and/or arm); light emitters on the device, wherein different light emitters in the array emit light beams along projection vectors which vary over time in a circular manner; and light receivers which receive light beams from the light emitters after the light beams have been transmitted through or reflected by the body member.

In an example, a light beam can be reflected from different regions and/or depths of body tissue by changing the angle and/or vector along which the light beam is emitted. In another example, a light emitter can be automatically tilted, rotated, raised, or lowered. In an example, a light receiver can be automatically tilted, rotated, raised, or lowered in order to maintain a selected angle (or angle range) with respect to the surface of a person's body. In another example, an angle and/or vector of light which has been emitted from a light emitter can be automatically changed over time by a device. In an example, an angle of light emitted from a light energy emitter can be adjusted in order to more accurately measure a biometric parameter level.

In an example, an angle of light emitted from the light energy emitter can be adjusted in order to more accurately measure a biometric parameter level. In an example, an electronic device worn on a person's finger (e.g. a finger ring) can include light emitters and light receivers, wherein angles between the light emitters the body-facing surface (e.g. inner circumference) of the device are adjusted and/or wherein angles between light receivers and the body-facing surface (e.g. inner circumference) of the device are adjusted. In an example, different emitters in this array can emit light at different angles based different types of activities in which a person is engaging.

In an embodiment, the angle and/or vector of light emitted from a light emitter can be automatically changed over time by the device. In an example, the angle at which light is emitted from a light emitter leaves a device and/or the angle at which the light intersects the surface of a person's body can be automatically changed over time in response to movement (e.g. shifting or rotation) of the device relative to the person's body. In an example, the depth, breadth, location, and/or type of body tissue or fluid from which light from a light energy emitter is reflected can be changed by adjusting the angle of light emitted from the light energy emitter.

In an example, a biometric wearable device (e.g. finger ring or smart watch) can comprise: a wearable device such as a wearable band or ring worn around a body member (e.g. finger, wrist, and/or arm); light emitters on the wearable device; light guides on the device, wherein the light guides change the vectors along which light beams from the light emitters travel; and light receivers on the device which receive light beams from the light emitters after the light beams have been transmitted through or reflected by the body member.

In an example, this biometric wearable device (e.g. finger ring or smart watch) can comprise: a wearable device worn on a body member (e.g. finger, wrist, and/or arm); light emitters around the wearable device; moving light guides on the device, wherein the light guides change the vectors along which light beams from the light emitters travel in an iterative (scanning) manner; and light receivers on the device which receive light beams from the light emitters after the light beams have been transmitted through or reflected by the body member.

In another example, a biometric wearable device can comprise: a wearable device (e.g. finger ring or smart watch) worn around a body member (e.g. finger, wrist, and/or arm); an arcuate array of light emitters around the wearable device; an arcuate array of light guides on the device which change the angles at which light beams from the light emitters hit the surface of the body member; and an arcuate array of light receivers on the device which receive light beams from the light emitters after the light beams have passed through the light guides and been transmitted through or reflected by the body member. In an example, a device can include light emitters, light detectors, and optical components (e.g. movable mirrors or lenses) which manipulate the direction of light beams from the light emitters, thereby enabling adjustment of the vectors along which they light beams are transmitted through a body member (e.g. finger, wrist, or arm).

In another example, a device can include one or more light guides which direct light beams from one or more light emitters from a first location, angle, and/or transmission vector to a second location, angle, and/or transmission vector. In an example, a light beam emitted by a light emitter can be automatically moved by using an actuator to automatically rotate, tilt, raise, or lower a light guide through which this beam is transmitted. In another example, a light beam emitted by a light emitter can be automatically moved by using an actuator to automatically rotate, tilt, raise, or lower a light guide through which this beam is transmitted.

In a variation on this design, a movable light guide can reflect and/or refract light from the light emitter at different angles (or along different vectors) toward a body member (e.g. finger, wrist, or arm) held by a biometric wearable device (e.g. finger ring or smart watch) as the light guide pivots and/or rotates. In an embodiment, light beams emitted from light emitters can be redirected (e.g. refracted or reflected) by movable lenses or mirrors in order to change the vectors along which the light beams are transmitted through a body member (e.g. finger, wrist, or arm). In an example, movement (e.g. pivoting and/or rotation) of a light guide can change the paths along which light beams from a light emitter travel through a body member (e.g. finger, wrist, or arm). In an example, the light beam from a light emitter can be automatically moved by using an actuator to automatically move a light guide through which this light is transmitted.

In an example, a light guide can redirect light from a light emitter. In an example, light from a light emitter can be redirected (e.g. reflected and/or refracted) by a light guide before it is transmitted through or reflected by a body member (e.g. finger, wrist, or arm). In an example, a light guide can be flexible. In an example, a light guide can be rigid. In an embodiment, a movable light guide can pivot and/or rotate around an axle. In an example, light from a first light emitter can reflected by a first side of a light guide toward a body member (e.g. finger, wrist, or arm) at a first time when the light guide is pivoted and/or rotated in a first direction and light from a second light emitter can be reflected by a second (e.g. opposite) side of the light guide toward the body member (e.g. finger, wrist, or arm) at a second time when the light guide is pivoted and/or rotated in a second direction.

In an example, a beam of light emitted by a light emitter can be automatically moved by using an actuator to automatically move a light reflector (such as a mirror) from which this beam is reflected. In another example, a biometric wearable device (e.g. finger ring or smart watch) can comprise: a device worn around a body member (e.g. finger, wrist, and/or arm); a motion sensor; a circumferential array of light emitters, micromirrors, electromagnetic actuators, and light receivers around the wearable device; wherein the micromirrors are automatically moved by the actuators based on data from the motion sensor; wherein light receivers receive light beams from the light emitters after the light beams have been reflected by the micromirrors and been transmitted through or reflected by the body member.

In an example, a biometric wearable device (e.g. finger ring or smart watch) can comprise: a device worn around a body member (e.g. finger, wrist, and/or arm); an array of light emitters and moving micromirrors, wherein the light beams are directed by the micromirrors along a first set of projection vectors at a first time and a second set of projection vectors at a second time, and wherein the light beams reach the body member at the same set of incidence vectors at the first and second times; light receivers which receive light beams emitted by the light emitters after the light beams have been transmitted through or reflected by the body member.

In another example, a biometric wearable device (e.g. finger ring or smart watch) can comprise: a device worn around a body member (e.g. finger, wrist, and/or arm); scanning light emitters on the device; moving micromirrors on the device; wherein light beams from the light emitters are directed (back and forth) along changing vectors (in a sinusoidal pattern) by the moving micromirrors; and light receivers on the device which receive light beams from the light emitters after the light beams have been transmitted through or reflected by the body member.

In an example, this biometric wearable device (e.g. finger ring or smart watch) can comprise: a wearable device worn around a body member (e.g. finger, wrist, and/or arm); a motion sensor; a circumferential array of light emitters, micromirrors, pneumatic actuators, and light receivers around the wearable device; wherein the micromirrors are automatically moved by the actuators based on data from the motion sensor; wherein light receivers receive light beams from the light emitters after the light beams have been reflected by the micromirrors and been transmitted through or reflected by the body member.

In another example, a biometric wearable device (e.g. finger ring or smart watch) can comprise: a wearable device worn around a body member (e.g. finger, wrist, and/or arm); moving micromirrors; scanning light emitters on the device, wherein light beams from the light emitters are directed along different vectors at different times by the micromirrors; and light receivers on the device which receive light beams from the light emitters after the light beams have been transmitted through or reflected by the body member. In an example, a biometric wearable device (e.g. finger ring or smart watch) can comprise: a wearable device worn on a body member (e.g. finger, wrist, and/or arm); a plurality of light emitters; a moving micromirror array; wherein light beams from the light emitters are reflected by the micromirror array toward the body member along different incidence vectors at different times; a plurality of light receivers which receive light beams emitted by a light emitter after the light beams have been reflected by the micromirror array and transmitted through or reflected by the body member.

In an example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member, and wherein each optical sensor set further comprises at least one red-light (e.g. infrared or visible red) emitter, at least one green-light emitter, and at least one light receiver; and a digital micromirror device (DMD) which scans light beams from light emitters across the surface of the body member.

In an embodiment, a biometric wearable device can comprise: a wearable device (e.g. finger ring or smart watch) worn around a body member (e.g. finger, wrist, and/or arm); a convex array of light emitters around the wearable device; a convex array of rotating micromirrors around the wearable device, wherein the micromirrors change the incidence angles at which light beams from the light emitters reach the surface of the body member; a convex array of light receivers around the wearable device which receive light beams from the light emitters after the light beams have passed through the micromirrors and been transmitted through or reflected by the body member. In a variation on this design, a biometric wearable device can comprise: a wearable device (e.g. finger ring or smart watch) worn around a body member (e.g. finger, wrist, and/or arm); light emitters and micromirrors, wherein the projection vectors of light beams from the light emitters and micromirrors vary over time in an iterative manner; and light receivers which receive light beams emitted by the light emitters after the light beams have been reflected by the micromirrors and transmitted through or reflected by the body member.

In an embodiment, a device which uses spectroscopic analysis to measure one or more biometric parameters can include one or more movable micromirrors which change the vectors of light beams emitted from light emitters. In an example, a light beam emitted by a light emitter can be automatically moved by using an actuator to automatically rotate, tilt, raise, or lower a light reflector (such as a mirror) from which this beam is reflected. In an embodiment, angles and/or vectors of light beams which are emitted by light emitters can be automatically changed one or more mechanisms selected from the group consisting of: electromagnetic actuators; moving micromirror or micromirror array; moving microlens or microlens array; and moving prism or microprism array. In an example, light rays emitted by a light emitter can be redirected by a micromirror array (e.g. a digital micromirror array). In an example, the angle at which a optical module (e.g. set) emits a beam of light into a body member (e.g. finger, wrist, or arm) can be changed by a movable light guide (e.g. a pivoting and/or rotating mirror) within the optical module (e.g. set).

In another example, a light guide can be a digital micromirror biometric wearable device. In an example, a light guide can be a moving (e.g. pivoting or rotating) prism. In another example, a movable light guide can be a movable micromirror. In an example, a beam of light emitted by a light emitter can be automatically moved by using an actuator to automatically move a lens through which this beam is transmitted. In another example, a light beam emitted by a light emitter can be automatically moved by using an actuator to automatically move a lens through which this beam is transmitted. In an example, a light beam from a light emitter can be automatically moved by using an actuator to automatically rotate, tilt, raise, or lower a lens through which this beam is transmitted. In an example, a light guide can be a lens.

In an example, a biometric wearable device (e.g. finger ring or smart watch) can include a rotating component (e.g. ball, sphere, or hemisphere) which holds a light emitter, a light receiver, or both. In an example, a device can include a component (e.g. ball) with a light emitter which can be rotated in different directions so that the range of possible projection beams from the emitter forms a conic or frustal shape in three-dimensional space.

In an example, a light guide (e.g. micromirror) in an optical module (e.g. set) can pivot and/or rotate around an axis (e.g. an axle) as it is exposed to an electromagnetic field. In an example, a light guide can be a moving (e.g. pivoting or rotating) micromirror array which is moved by interaction with a changing electromagnetic field. In an example, a light guide can be pivoted and/or rotated by changes in an electromagnetic field created by electrodes in the optical module (e.g. set). In an embodiment, an optical module (e.g. set) can further comprise electrodes, wherein transmission of electrical energy through the electrodes creates an electromagnetic field which moves (e.g. pivots or rotates) a movable light guide.

In a variation on this design, a biometric wearable device (e.g. finger ring or smart watch) can comprise: a wearable device worn on a body member (e.g. finger, wrist, and/or arm); a motion sensor; an actuator; a light emitter on the device; wherein the vector along which light beams from a light emitter travel is adjusted by the actuator based on data from the motion sensor in order to maintain the same incidence angle at which the light beams hit the body member, even when the wearable device shifts or rotates on the body member; and a light receiver which receives light beams from a light emitter after the light beams have been transmitted through or reflected by the body member.

In an example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one motion sensor, and at least one piezoelectric actuator which automatically adjusts the orientation (and/or angle) of the optical sensor set relative to the surface of the body member to maintain a selected orientation (and/or angle) between the optical sensor set and the body member if the device moves relative to the body member.

In an example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one motion sensor, and at least one electromagnetic actuator which automatically adjusts the orientation (and/or angle) of the optical sensor set relative to the surface of the body member.

In another example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one motion sensor, and at least one piezoelectric actuator which automatically moves the optical sensor set.

In an example, this biometric wearable device (e.g. finger ring or smart watch) can comprise: an arcuate band (or ring) which is configured to be worn around a body member (e.g. finger, wrist, and/or arm); at least three optical sensor sets which are held in proximity to the body member, wherein the optical sensor sets collectively span at least two-thirds of the circumference of the body member; and wherein each optical sensor set further comprises at least one red-light (e.g. infrared or visible red) emitter, at least one green-light emitter, and at least one light receiver; at least motion sensor; and at least one piezoelectric actuator which automatically adjusts the orientation (and/or angle) of one or more optical sensor sets relative to the body member in response to data from the motion sensor.

In another example, a biometric wearable device (e.g. finger ring or smart watch) can comprise: an arcuate band (or ring) which is configured to be worn around a body member (e.g. finger, wrist, and/or arm); at least three optical sensor sets which are held in proximity to the body member, wherein the optical sensor sets collectively span at least two-thirds of the circumference of the body member; and wherein each optical sensor set further comprises at least one red-light (e.g. infrared or visible red) emitter, at least one green-light emitter, and at least one light receiver; at least motion sensor; and at least one electromagnetic actuator which automatically adjusts the orientation (and/or angle) of one or more optical sensor sets relative to the body member in response to data from the motion sensor.

In an example, a device can include a motion sensor and can automatically change the angle and/or vector of light beams based on data from the motion sensor in order to maintain the same angle and/or vector of incidence with respect to the surface of a person's body even if the device shifts and/or rotates with respect to the person's body. In another example, a projection angle of a beam of light emitted from a light energy emitter can be changed in response to specific environmental conditions (e.g. temperature or humidity) and/or specific activities in which the person wearing a device is engaged (e.g. high level of movement, eating, sleeping, etc.) in order to more accurately measure a biometric parameter level. In an example, an angle of light emitted from a light energy emitter can be adjusted automatically (in an iterative manner) by a device in order to more accurately measure a biometric parameter level for a specific person, for a specific type of activity, or for a specific configuration of the device relative to the person's body surface.

In an example, a biometric wearable device (e.g. finger ring or smart watch) can comprise: a device worn around a body member (e.g. finger, wrist, and/or arm); scanning light emitters on the device; MEMS components on the device; wherein light beams from the light emitters are directed along different vectors at different times by the MEMS components; and light receivers on the device which receive light beams from the light emitters after the light beams have been transmitted through or reflected by the body member.

In an example, this biometric wearable device (e.g. finger ring or smart watch) can comprise: a wearable device such as a wearable band or finger ring worn around a body member (e.g. finger, wrist, and/or arm); a circumferential array of actuators around the wearable device; an array of micromirrors around the wearable device which are iteratively rotated and/or pivoted by the array of actuators; an array of light emitters around the device whose light beams are reflected by the array of micromirrors back and forth over different locations on the body member over time as the mirrors are rotated and/or pivoted; and one or more light receivers which receive light beams from the light emitters after the light beams have been transmitted through or reflected by the body member.

In an example, a biometric wearable device (e.g. finger ring or smart watch) can comprise: a wearable device worn on a body member (e.g. finger, wrist, and/or arm); a plurality of at least ten scanning light emitters on the device, wherein scanning light emitters emit light beams with projection vectors which change over time; and a light receiver on the device which receives the light beams from the light emitters after the light beams have been transmitted through or reflected by the body member. In an embodiment, a biometric wearable device (e.g. finger ring or smart watch) can comprise: a wearable device worn on a body member (e.g.

finger, wrist, and/or arm); an actuator; a moving mirror which is tilted or rotated in an iterative manner by the actuator; a light emitter whose light beams are reflected by the mirror toward the body member along different vectors at different times in order to scan different areas of the body member; and a light receiver which receives light beams emitted by a light emitter after the light beams have been transmitted through or reflected by the body member.

In an example, a biometric wearable device can comprise: a wearable device (e.g. finger ring or smart watch) worn around a body member (e.g. finger, wrist, and/or arm); a scanning light emitter which emits light beams which are reflected from different depths of the tissue of the body member over time; and a light receiver on the device which receives light beams emitted by a light emitter after the light beams have been transmitted through or reflected by the body member. In an example, a biometric wearable device can comprise: a wearable device (e.g. finger ring or smart watch) worn around a body member (e.g. finger, wrist, and/or arm); a scanning light emitter which emits light beams which sweep over the body member along different vectors over time; and a light receiver on the device which receives light beams emitted by a light emitter after the light beams have been transmitted through or reflected by the body member.

In an example, a biometric wearable device can comprise: a wearable device (e.g. finger ring or smart watch) worn on a body member (e.g. finger, wrist, and/or arm); light emitters on the device, wherein different light emitters emit light beams along projection vectors which vary over time in a sinusoidal manner; and light receivers which receive light beams from the light emitters after the light beams have been transmitted through or reflected by the body member. In another example, a device can include light emitters, light detectors, and optical components which redirect the vectors of light beams emitted from the light emitters, enabling adjustment of the optical path of these light beams through a body member (e.g. finger, wrist, or arm) and scanning a region of the body member via multiple optical paths.

In an example, a movable light guide in an optical module (e.g. set) in a biometric wearable device (e.g. finger ring or smart watch) can move (e.g. pivot and/or rotate) in a continuous manner, thereby causing a beam of light from a light emitter to smoothly sweep (e.g. scan) through a body member (e.g. finger, wrist, or arm) at different angles (e.g. along different vectors). In another example, an angle and/or vector along which a light emitter emits beams of light can be automatically oscillated and/or iteratively-varied to scan different regions and/or depths of body tissue. In an example, an angle of a beam of light emitted from a light energy emitter can be changed over time to create a chronological sequence of beams of light with different projection and/or body incidence angles.

In another example, beams of light can be emitted from different light emitters along different angles and/or vectors in order to scan different tissue depths and/or regions. In a variation on this design, movement (e.g. pivoting and/or rotation) of a light guide can cause beams of light from a light emitter to scan different sections and/or locations of a body member (e.g. finger, wrist, or arm) at different times. In another example, when a ring shifts and/or rotates on a finger, the ring device can automatically change the angle and/or vector of light beams emitted from one or more light emitters in order to maintain spectroscopic scanning of the same tissue region even when a device shifts and/or rotates.

In an example, a biometric wearable device (e.g. finger ring or smart watch) can comprise: a wearable device worn around a body member (e.g. finger, wrist, and/or arm); an actuator; a light emitter on the device; and a light receiver on the device which receives light beams emitted by the light emitter after the light beams have been transmitted through or reflected by the body member, wherein the actuator changes the vector along which a light emitter emits light beams.

In an example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one orientation (and/or angle) sensor which measures the orientation (and/or angle) of the optical sensor set relative to the surface of the body member, and at least one electromagnetic actuator which automatically adjusts the orientation (and/or angle) of the optical sensor set relative to the surface of the body member in response to data from the orientation (and/or angle) sensor.

In an embodiment, a biometric wearable device (e.g. finger ring or smart watch) can comprise: light emitters which direct light toward a person's body; light receivers which receive this light after it has been transmitted through or reflected by body tissue; and actuators (e.g. electromagnetic, pneumatic, or hydraulic actuators) which change the angles between light receivers and the surface of the person's body. In an example, a device can include an actuator which adjusts the orientation (and/or angle) of an optical sensor in order to maintain a selected orientation (and/or angle) of the sensor relative to a body member (e.g. finger, wrist, or arm).

In an example, a light emitter of this system can be automatically moved by an actuator relative to a housing which holds it. In an example, a light emitter on a device can be automatically tilted by an actuator. In an example, an optical sensor (e.g. light emitter, light detector, or both) on a device can be moved by an actuator to restore good optical communication between the sensor and a body member (e.g. finger, wrist, or arm) is that optical communication is impaired due to shifting of the device. In an example, the beam of light emitted by a light emitter can be automatically moved by using an actuator to automatically rotate, tilt, raise, or lower a light guide through which this beam is transmitted.

In an example, a biometric wearable device (e.g. finger ring or smart watch) can comprise a plurality of optical modules (e.g. modules or sets having light emitters and light receivers) which collectively span (at least half) of the circumference of a body member (e.g. finger, wrist, or arm), wherein light from one or more light emitters in an optical module is received by one or more light receivers in that module. In another example, an optical module (e.g. set) can comprise a triad of light emitters and light receivers. In an example, an optical module (e.g. set) can have multiple light emitters. In another example, an optical module (e.g. set) can have multiple light emitters and a light receiver which are configured in a straight line. In an embodiment, an optical module (e.g. set) can include one light receiver and a plurality of light emitters.

In another example, an optical module (e.g. set) can include one light receiver and a plurality of light emitters distributed around the light receiver. In an example, an optical module (e.g. set) can include one light emitter and a plurality of light receivers which are evenly-distributed around the light emitter. In an example, an optical module (e.g. set) of light emitters in an array of light emitters can comprise two or more light emitters. In a variation on this design, modules in a first module (e.g. set) can each comprise a light emitter and modules in a second module (e.g. set) of optical modules (e.g. sets) can each comprise a light receiver. In an example, some optical modules (e.g. sets) can include light emitters and some optical modules (e.g. sets) can include light receivers. In an example, a light receiver can receive light from a light emitter which is located in the same optical module (e.g. set) as the light receiver.

In an example, a movable light guide in an optical module (e.g. set) in a biometric wearable device (e.g. finger ring or smart watch) can have a circular, elliptical, or oval shape. In an example, an optical module (e.g. set) can comprise a first light emitter, a second light emitter, a movable light guide, and a light receiver. In an embodiment, an optical module (e.g. set) can comprise two light emitters, a light guide, and a light receiver, wherein all of the components are arranged in a line. In an example, an optical module (e.g. set) can include a light guide. In another example, an optical module (e.g. set) can include a movable refractive light guide.

In an example, this biometric wearable device (e.g. finger ring or smart watch) can comprise a plurality of optical modules (e.g. sets) containing light emitters and light receivers around the circumference of a body member (e.g. finger, wrist, or arm), wherein different optical modules are activated sequentially in a clockwise (or counter-clockwise) manner around the circumference of the body member (e.g. finger, wrist, or arm). In another example, a biometric wearable device (e.g. finger ring or smart watch) can have a circumferential, annular, and/or circular array of sequentially-activated light emitters. In an example, a first light at a first polar coordinate can be activated to emit light at a first time and second light at a second polar coordinate can be activated to emit light at a second time, wherein the second light is the light in the array which is clockwise (or counter-clockwise) most proximal to the first light.

In another example, a first light emitter can emit light with a wavelength in the range of 650 to 750 nm at a first time; a second light emitter can emit light with a wavelength in the range of 750 nm to 850 nm at a second time; and a third light emitter can emit light with a wavelength in the range of 850 nm to 950 nm at a third time. In an example, a first subset of one or more light emitters selected from an array of light emitters can have a first average polar coordinate and emit light at a first point in time and a second subset of one or more light emitters selected from an array of light emitters can have a second average polar coordinate and emit light at a second point in time.

In an example, an optical (e.g. spectroscopic) sensor can comprise a plurality of light emitters which are selectively and sequentially activated. In an example, an optical module (e.g. set) can have multiple light emitters which emit light at different times. In an example, different combinations of light emitters in a circumferential array can be activated in order to measure combined effects of light reflected from, or having passed through, the body along different pathways. In an embodiment, different optical modules (e.g. sets) can be activated to transmit light into a body member (e.g. finger, wrist, or arm) at different times. In a variation on this design, first and second light emitters can emit light in a selected chronological sequence and/or timing pattern.

In an example, light emitters in a circumferential array can be activated in a sequence, like moving lights on a theater marquee. In another example, optical modules (e.g. sets) in an array of optical modules (e.g. sets) can be activated in a linear sequence. In an example, the duration of activation of different subsets of light emitters in a circumferential array can be adjusted based on analysis of light spectra. In another example, there can be overlap in the times that different subsets of light emitters are activated in a circumferential array.

In an example, a biometric wearable device (e.g. finger ring or smart watch) can comprise: a wearable device worn around a body member (e.g. finger, wrist, and/or arm); a motion and/or orientation sensor; light emitters, wherein a subset of the light emitters are selected to emit light at a given time, wherein the subset is selected based on data from the motion and/or orientation sensor; and light receivers which receive light beams from the light emitters after the light beams have been transmitted through or reflected by the body member.

In another example, a biometric wearable device can comprise: a wearable device (e.g. finger ring or smart watch) worn around a body member (e.g. finger, wrist, and/or arm); a convex array of electromagnetic energy sensors, wherein data from the electromagnetic energy sensors is analyzed to determine the orientation of the device relative to the body member; a convex array of light emitters around the device; wherein a selected subset of the light emitters are activated based on the orientation of the device relative to the body member; and a convex array of light receivers around the device which receives light beams emitted by the light emitters after light beams have been transmitted through or reflected by the body member.

In an example, a biometric wearable device can comprise: a wearable device (e.g. finger ring or smart watch) worn around a body member (e.g. finger, wrist, and/or arm); one or more sensors selected from the group consisting of ballistocardiographic sensor, blood flow sensor, blood pressure sensor, body temperature sensor, Hall-effect sensor, heart rate sensor, heat sensor, humidity sensor, hygrometry sensor, photoplethysmography (PPG) sensor, sound sensor, and temperature sensor; an arcuate array of light emitters around the wearable device, wherein a selected subset of the light emitters are activated to emit light at a given time based on data from the one or more sensors; and one or more light receivers which receive light beams from the light emitters after the light beams have been transmitted through or reflected by the body member.

In an example, different emitters in an array can be activated to emit light when a person is engaged in different types of activities. In an example, a first light emitter at a first location on a biometric wearable device (e.g. finger ring or smart watch) can emit (a pulse of) light at a first time and a second light emitter at a second location on the device can emit (a pulse of) light at a second time. In an embodiment, a light emitter can be a laser with a narrow pulse width. In an example, a light emitter can emit light pulses.

In an example, this biometric wearable device (e.g. finger ring or smart watch) can comprise a plurality of optical (e.g. spectroscopic) sensors which sequentially emit light at different frequencies. In an example, a biometric wearable device (e.g. finger ring or smart watch) can comprise: a wearable device worn around (a portion of) a body member (e.g. finger, wrist, and/or arm); a circumferential array of light emitters around the wearable device, wherein light emitters in the array of light emitters emit light beams with spectral ranges, frequencies, and/or colors which vary over time; and one or more light receivers which receive light beams from the light emitters after the light beams have been transmitted through or reflected by the body member.

In an example, a first light emitter which emits light in a first color can emit light at a first time and a second light emitter which emits light in a second color can emit light at a second time. In a variation on this design, a frequency, color, and/or spectrum of a light beam emitted from a light energy emitter can be changed in response to specific environmental conditions (e.g. temperature or humidity) and/or specific activities in which the person wearing a device is engaged (e.g. high level of movement, eating, sleeping, etc.) in order to more accurately measure a biometric parameter level. In another example, a light emitter can emit light with a first light wavelength (or wavelength range or spectral distribution) during a first time period and can emit light with a second light wavelength (or wavelength range or spectral distribution) during a second time period.

In an example, a light emitter can emit light with a first light wavelength (or wavelength range or spectral distribution) during a first time period and can emit light with a second light wavelength (or wavelength range or spectral distribution) during a second time period in response to changing physiological conditions. In another example, a light emitter can emit light within a spectral range which varies over time. In another example, a light emitter of an optical (e.g. spectroscopic) sensor can emit light in a sweeping series of frequencies. In an example, different emitters can emit light with different wavelengths or wavelength ranges based in response to different environmental parameters or conditions.

In an embodiment, the depth, breadth, location, and/or type of body tissue or fluid from which light from a light emitter is reflected can be changed by adjusting the frequency, color, and/or spectrum of light emitted from the light emitter. In an example, the frequency, color, and/or spectrum of a light beam emitted from a light emitter can be changed over time to create a chronological sequence of beams of light with different frequencies, colors, and/or spectrums. In an example, the frequency, color, and/or spectrum of light emitted from the light emitter can be adjusted automatically to maintain accurate measurement of biometric parameter level even if the device shifts and/or moves relative to the person's body surface. In an example, the operation of an optical (e.g. spectroscopic) sensor can include frequency-based modulation. In an example, the wavelengths and/or frequencies of light from light emitters can be varied in a repeated pattern. In an example, the wavelengths and/or frequencies of light from light emitters can be changed in periodic manner.

In an example, this biometric wearable device (e.g. finger ring or smart watch) can automatically vary the power and/or intensity of light from a light emitter to scan through a range of tissue depths, locations, and/or types in order to obtain more accurate measurement of a biometric parameter level. In an example, a biometric wearable device can comprise: a wearable device (e.g. finger ring or smart watch) worn around a body member (e.g. finger, wrist, and/or arm); light emitters, wherein the power or intensity levels of light beams from the light emitters vary over time in an iterative manner; and light receivers which receive light beams emitted by the light emitters after the light beams have been transmitted through or reflected by the body member.

In an embodiment, a power and/or intensity of a light beam emitted from a light energy emitter can be changed in response to specific environmental conditions (e.g. temperature or humidity) and/or specific activities in which the person wearing a device is engaged (e.g. high level of movement, eating, sleeping, etc.) in order to more accurately measure a biometric parameter level. In another example, the depth, breadth, location, and/or type of body tissue or fluid from which light from a light emitter is reflected can be changed by adjusting the power and/or intensity of light emitted from the light emitter. In a variation on this design, the power and/or intensity of light emitted from the light emitter can be adjusted automatically (in an iterative manner) by a device in order to more accurately measure biometric parameter level for a specific person, for a specific type of activity, or for a specific configuration of the device relative to the person's body surface. In another example, the power and/or intensity of light emitted from the light emitter can be adjusted in order to more accurately measure a biometric parameter level.

In an example, a biometric wearable device (e.g. finger ring or smart watch) can automatically vary the coherence, polarization, and/or phase of light from a light emitter to scan through a range of tissue depths, locations, and/or types in order to obtain more accurate measurement of a biometric parameter level. In another example, the depth, breadth, location, and/or type of body tissue or fluid from which light from a light emitter is reflected can be changed by adjusting the coherence, polarization, and/or phase of light emitted from the light emitter.

In an example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the plurality of optical sensor sets collectively span at least two-thirds of the circumference of the body member; and wherein each optical sensor set further comprises: at least one red-light (e.g. infrared or visible red) emitter, at least one green-light emitter, at least one light receiver, at least one motion sensor, and at least one microhydraulic (or micropneumatic) actuator which automatically moves the set to maintain a selected distance (or proximity or pressure) between the optical sensor set and the body member if the device moves relative to the body member.

In an example, a biometric wearable device (e.g. finger ring or smart watch) can comprise: an arcuate band (or ring) which is configured to be worn around a body member (e.g. finger, wrist, and/or arm); at least three optical sensor sets which are held in proximity to the body member, wherein the plurality of optical sensor sets collectively span at least two-thirds of the circumference of the body member; and wherein each optical sensor set further comprises at least one red-light (e.g. infrared or visible red) emitter, at least one green-light emitter, and at least one light receiver; at least motion sensor; and at least one piezoelectric actuator which automatically adjusts the distance (or proximity or pressure) between one or more optical sensor sets and the body member in response to data from the motion sensor.

In an example, a light emitter can be automatically tilted, rotated, raised, or lowered in order to maintain a selected distance (or distance range) from the surface of a person's body. In an example, an electronic device worn on a person's finger (e.g. a finger ring) can include light emitters and light receivers, wherein distances between the light emitters and/or light receivers and the body-facing surface (e.g. inner circumference) of the device can be adjusted to customize the fit of the device to the size of the person's finger. In an example, the distance between a light emitter and a light receiver can be adjusted by rotating a member.

In an embodiment, a biometric wearable device (e.g. finger ring or smart watch) can automatically vary the geometric configuration of a plurality of light emitters and a light receiver in order to scan through a range of tissue depths, locations, and/or types in order to measure biometric parameter level more accurately. In an example, a biometric wearable device (e.g. finger ring or smart watch) can have an arcuate channel, groove, or track (around at least part of its circumference) along which a light emitter can be automatically moved (e.g. rotated) by an actuator in the device.

In an example, a biometric wearable device can comprise: a wearable device (e.g. finger ring or smart watch) worn around a body member (e.g. finger, wrist, and/or arm); an arcuate track, channel, or slot around (a portion of) the circumference of the wearable device; a light emitter which slides along the arcuate track, channel, or slot, wherein the light beams are directed toward the body member at a first angle at a first time and a second angle at a second time; wherein the second angle differs from the first angle by between 1 and 10 degrees; and a light receiver on the device which receives light beams emitted by a light emitter after the light beams have been transmitted through or reflected by the body member. In an example, a biometric wearable device can comprise: a wearable device (e.g. finger ring or smart watch) worn around a body member (e.g. finger, wrist, and/or arm); an arcuate track, channel, or slot around (a portion of) the circumference of the wearable device; a light emitter which is automatically moved clockwise (or counter clockwise) around the wearable device along the arcuate track, channel, or slot; a light receiver on the device which receives light beams emitted by a light emitter after the light beams have been transmitted through or reflected by the body member.

In another example, a light emitter can be moved (e.g. rotated) around at least half of the circumference of the device. In an example, movement of a light emitter, a light receiver, or both along a track, channel, or slot around the circumference of a device can enable customization of a device to the anatomy of a specific person for more accurate measurement of that person's biometric parameter. In another example, the circumferential location of a light emitter on the circumference of the body member (e.g. finger, wrist, or arm) can be automatically oscillated and/or iteratively-varied by a device. In an example, the location of a light emitter and/or a light receiver relative to a person's body can be adjusted by moving the light emitter, the light receiver, or both along a track, channel, or slot around the circumference of a device.

In another example, a biometric wearable device (e.g. finger ring or smart watch) can comprise: a device worn around a body member (e.g. finger, wrist, and/or arm); a motion sensor (e.g. accelerometer and/or gyroscope); an arcuate array of light emitters around the wearable device, wherein a subset of the light emitters is selected to emit light at a given time based on data from the motion sensor at that time; and one or more light receivers which receive light beams from the light emitters after the light beams have been transmitted through or reflected by the body member.

In a variation on this design, a biometric wearable device (e.g. finger ring or smart watch) can comprise: a wearable device worn around a body member (e.g. finger, wrist, and/or arm); a motion sensor; a circumferential array of light emitters around the wearable device; a circumferential array of microlenses around the wearable device, wherein light beams from the light emitters are redirected by the microlenses, and wherein the configurations of the microlenses are automatically changed by electromagnetic, hydraulic, or pneumatic actuators based on data from the motion sensor; a circumferential array of light receivers on the device which receive light beams from a light emitter after the light beams have been transmitted through or reflected by the body member.

In an example, this biometric wearable device (e.g. finger ring or smart watch) can comprise: a wearable device worn around a body member (e.g. finger, wrist, and/or arm); one or more sensors on the device selected from the group consisting of motion sensor, muscle function monitor, near-infrared spectroscopic (e.g. optical) sensor, neural impulse monitor, neurosensor, optical sensor, and optoelectronic sensor; an arcuate array of light emitters around the device, wherein the projection or incidence vectors of light beams emitted from the light emitters are changed based on data from the one or more sensors; and an arcuate array of light receivers around the device which receive light beams from the light emitters after the light beams have been transmitted through or reflected by the body member.

In an embodiment, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the plurality of optical sensor sets collectively span at least two-thirds of the circumference of the body member; and wherein each optical sensor set further comprises: at least one red-light (e.g. infrared or visible red) emitter, at least one green-light emitter, at least one light receiver, at least one motion sensor, and at least one piezoelectric actuator which automatically moves the optical sensor set.

In an example, a biometric wearable device (e.g. finger ring or smart watch) can comprise: a device worn around a body member (e.g. finger, wrist, and/or arm); a convex array of electromagnetic energy sensors around the device; a convex array of light emitters around the device, wherein the projection vectors of light beams emitted from the circumferential array of light emitters are changed based on data from the electromagnetic energy sensors; and one or more light receivers which receive light beams from the light emitters after the light beams have been transmitted through or reflected by the body member.

In an example, this biometric wearable device (e.g. finger ring or smart watch) can comprise: a plurality of body-facing (e.g. radially-inward) sensors (e.g. electromagnetic sensors or optical sensors) around the inner surface (e.g. inner circumference) of the device; and a plurality of actuators (e.g. electromagnetic, pneumatic, or hydraulic actuators) which selectively adjust the angles between a subset of the sensors and the surface of the person's body.

In an example, a biometric wearable device can comprise: a wearable device (e.g. finger ring or smart watch) worn around a body member (e.g. finger, wrist, and/or arm); an arcuate array of electromagnetic energy sensors around the body member; an arcuate array of light emitters around the body member, wherein different light emitters emit light beams along vectors which are automatically changed over time based on data from the array of electromagnetic energy sensors; and an arcuate array of light receivers which receive light beams from the light emitters after the light beams have been transmitted through or reflected by the body member.

In an example, a biometric wearable device (e.g. finger ring or smart watch) can comprise: a device worn around a body member (e.g. finger, wrist, and/or arm); a strain gauge or stretch sensor; an arcuate array of light emitters around the wearable device, wherein parameters (e.g. intensity, frequency or color, projection vector) of light energy from the light emitters are selected at a given time based on data from the strain gauge or stretch sensor at that time; and one or more light receivers which receive light beams from the light emitters after the light beams have been transmitted through or reflected by the body member.

In an example, a biometric wearable device (e.g. finger ring or smart watch) can comprise: a wearable device worn around a body member (e.g. finger, wrist, and/or arm); an environmental sensor on the device; an arcuate array of light emitters around the device, wherein the projection vectors of light beams emitted from the arcuate array of light emitters are changed based on data from the environmental sensor; and one or more light receivers which receive light beams from the light emitters after the light beams have been transmitted through or reflected by the body member.

In an example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the plurality of optical sensor sets collectively span at least two-thirds of the circumference of the body member; and wherein each optical sensor set further comprises: at least one red-light (e.g. infrared or visible red) emitter, at least one green-light emitter, at least one light receiver, at least one orientation (and/or angle) sensor, and at least one piezoelectric actuator which automatically moves the optical sensor set.

In an example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one orientation (and/or angle) sensor, and at least one microhydraulic (or micropneumatic) actuator which automatically moves the optical sensor set to maintain a selected orientation (and/or angle) between the optical sensor set and the body member if the device moves relative to the body member.

In another example, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one orientation (and/or angle) sensor which measures the orientation (and/or angle) of the optical sensor set relative to the surface of the body member, and at least one microhydraulic (or micropneumatic) actuator which automatically adjusts the orientation (and/or angle) of the optical sensor set relative to the surface of the body member.

In an embodiment, a biometric wearable device (e.g. finger ring or smart watch) can comprise: an arcuate band (or ring) which is configured to be worn around a body member (e.g. finger, wrist, and/or arm); and at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one orientation (and/or angle) sensor which measures the orientation (and/or angle) of the optical sensor set relative to the surface of the body member, and at least one piezoelectric actuator which automatically adjusts the orientation (and/or angle) of the optical sensor set relative to the surface of the body member to maintain a selected orientation (and/or angle) between the optical sensor set and the body member if the device moves relative to the body member.

In another example, a biometric wearable device (e.g. finger ring or smart watch) can comprise: at least three optical sensor sets which are held in proximity to the body member, wherein the optical sensor sets collectively span at least two-thirds of the circumference of the body member; and wherein each optical sensor set further comprises: at least one red-light (e.g. infrared or visible red) emitter, at least one green-light emitter, at least one light receiver, at least one orientation (and/or angle) sensor, and at least one actuator which automatically moves the optical sensor set. In an example, a biometric wearable device (e.g. finger ring or smart watch) can further comprise one or more sensors selected from the group consisting of: electrocardiographic (ECG) sensor, strain gauge, magnetometer, inertial sensor, electromagnetic sensor, sweat sensor, biochemical sensor, photochemical sensor, and electromyographic (EMG) sensor.

In another example, a device can further comprise one or more distance and/or pressure sensors. In an example, a device or system can further comprise one or more sensors selected from the group consisting of: capacitance hygrometry sensor, piezoresistive sensor, impedance sensor, and variable translucence sensor. In an example, a device worn on a person's finger (e.g. a finger ring) can include a photoplethysmography (PPG) sensor. In a variation on this design, a shape of a sensor can be adjusted in real time in order to maintain accurate measurement of intra-biometric parameter levels. In an example, a wearable biometric parameter-monitoring microwave sensor can further comprise one or more actuators which automatically adjust the shape of the sensor.

In an example, this biometric wearable device (e.g. finger ring or smart watch) can comprise: (a) a housing (e.g. finger ring or smart watch housing) which is worn on a body member (e.g. finger, wrist, or arm); an array of light emitting optical modules (e.g. sets) and light receivers on the housing; wherein light emitted from the light emitters is transmitted through or reflected by the person's body tissue and received by the light receivers; wherein attributes (e.g. the spectral distribution) of light received by the light receivers are analyzed to measure one or more biometric parameters and/or detect one more physiological conditions of the person; wherein the array has a circular, approximately-circular polygonal (e.g. hexagonal or octagonal), annular, or circumferential shape; wherein there is an alternating pattern of light emitting optical modules and light receivers around the perimeter of the array; wherein there are a plurality (e.g. three or more) of light emitters in each light emitter module; wherein different light emitters in an optical module emit light with different colors, wavelengths, and/or frequencies; and wherein at least one light emitter in an optical module emits red light, at least one light emitter in an optical module emits infrared light, and at least one light emitter in an optical module emits green light; and (b) one or more (compressible, compliant, and/or elastomeric) opaque light barriers surrounding one or more light receivers; wherein the one or more light barriers reduce or eliminate transmission of light from the light emitters to the light receivers which has not been reflected by or transmitted through the person's body tissue; and/or wherein the one or more light barriers reduce or eliminate transmission of ambient light to the light emitters.

In an example, a biometric wearable device (e.g. finger ring or smart watch) can comprise an alternating (emitter then receiver) array of light emitters and light receivers, wherein light receivers are surrounded by a light barrier which prevents light from light emitters from reaching the light receivers without first being reflected from, or transmitted through, body tissue. In an embodiment, a biometric wearable device (e.g. finger ring or smart watch) can include a plurality of light barriers and a plurality of light receivers, wherein each light barrier surrounds a subset of light receivers. In an example, a biometric wearable device (e.g. finger ring or smart watch) can include one or more light barriers (e.g. light shields, light blockers, cladding, and/or opaque barriers) between ambient light and one or more light receivers which reduce the transmission of light energy from the ambient light to the light receiver. In another example, a biometric wearable device (e.g. finger ring or smart watch) can include two light barriers: one light barrier between (sets of) light emitters in the device and light receivers in the device; and one light barrier between ambient light and light receivers in the device.

In an example, a device for measuring one or more of a person's biometric parameters can comprise: a housing which is configured to be worn on a person's wrist, arm, or finger; an array of light emitting optical modules (e.g. sets) and light receivers on the housing; wherein light emitted from the light emitters is transmitted through or reflected by the person's body tissue and received by the light receivers; wherein attributes of the light received by the light receivers are analyzed to measure one or more biometric parameters of the person; wherein there is an alternating pattern of light emitting optical modules and light receivers in the array; and wherein at least one light emitter in an optical module emits red light, at least one light emitter in the optical module emits infrared or near-infrared light, and at least one light emitter in the optical module emits green light; a data processor; and one or more opaque light barriers surrounding one or more light receivers, wherein the light barriers are compressible, compliant, and/or elastomeric. In another example, a light barrier can be an opaque ring around a light receiver.

In an example, a light barrier can be made from an opaque elastomeric polymer. In another example, a light barrier can be made from opaque foam. In an example, a light barrier can comprise a circular and/or annular opaque ring between ambient light and a light receiver (or module or set of light receivers). In an example, a light barrier can comprise a polygon (e.g. quadrilateral, hexagon, or octagon shaped member) of compressible, compliant, and/or elastomeric opaque material between ambient light and a light receiver (or module or set of light receivers). In a variation on this design, a light barrier can comprise a polygon (e.g. quadrilateral, hexagon, or octagon shaped member) of compressible, compliant, and/or elastomeric opaque material around a light receiver. In an example, a light barrier can comprise a ring of compressible, compliant, and/or elastomeric opaque material between ambient light and a light receiver (or module or set of light receivers).

In an embodiment, a light barrier can comprise a ring of opaque material between ambient light and a light receiver (or module or set of light receivers). In an example, a light barrier can encircle two or more light emitters. In an example, a light barrier can have a circular, elliptical, or annular shape, wherein a light receiver is at the center of this shape. In another example, a light barrier can have a longitudinal axis which is substantially parallel to the vector of (collimated or coherent) light beams from a light emitter. In an example, a light barrier can have an undulating and/or sinusoidal shape. In another example, a light barrier can surround a perimeter around a subset (e.g. two or more) of light emitters. In another example, a single light barrier can surround all of the light receivers.

In an example, an optical module (e.g. set) can further comprise an opaque light shield or barrier between a light emitter and a light receiver. In an example, each light receiver in a wearable device can be optically isolated from ambient light by a separate light barrier. In an example, light barriers can be compressible, compliant, and/or elastomeric. In a variation on this design, subsets of one or more light receivers can be optically isolated from ambient light by the same light barrier. In an embodiment, there can be a circular and/or annular light barrier around each light emitter in a wearable device. In an example, there can be a light barrier around each light receiver in a wearable device. In an example, there can be one light barrier which encircles all light receivers in a wearable device. In an example, this biometric wearable device (e.g. finger ring or smart watch) can further comprise one or more piezoelectric portions (e.g. bands) whose contraction helps the device to fit more snugly on a body member (e.g. finger, wrist, or arm).

In another example, a biometric wearable device can comprise: a ring which is configured to be worn around a person's finger, wherein the ring has a plurality of radial undulations; and at least three optical sensors which are held in proximity to the person's finger, wherein the optical sensors are located on portions of the ring which protrude toward the surface of the person's finger, wherein each optical sensor further comprises at least one red-light (e.g. infrared or visible red) emitter, at least one green-light emitter, or at least one light receiver. In another example, a biometric wearable device can comprise: a ring which is worn on a person's finger; and optical sensors on portions of the ring which protrusions extending toward the surface of the person's finger, wherein an optical sensor comprises an infrared light emitter, a red light emitter, a green-light emitter, or a light receiver.

In an example, a wearable biometric device can comprise: an arcuate band (or ring) which is configured to be worn around a person's wrist (or finger), wherein the arcuate band (or ring) spans at least two-thirds of the circumference of the person's wrist (or finger), wherein the arcuate band (or ring) has a plurality of radial undulations; and at least three optical sensor sets which are held in proximity to the person's wrist (or finger), wherein the optical sensor sets are located on portions of the band (or ring) which protrude toward the surface of the person's wrist (or finger), wherein the optical sensor sets collectively span at least two-thirds of the circumference of the person's wrist (or finger), wherein each optical sensor set further comprises at least one red-light (e.g. infrared or visible red) emitter, at least one green-light emitter, at least one light receiver.

In an example, a first portion of a biometric wearable device (e.g. finger ring or smart watch) can have a first elasticity level and a second portion of the device can have a second elasticity level, wherein the second level is greater than the first level. In an example, a first portion of a biometric wearable device (e.g. finger ring or smart watch) can have a first level of stretchability and a second portion of the device can have a second level of stretchability, wherein the second level is greater than the first level, and wherein optical modules (e.g. sets) (e.g. light emitters and receivers) are located on the first portion.

In an embodiment, a first portion of a biometric wearable device (e.g. finger ring or smart watch) can have a first Shore value and/or durometer level and a second portion of the device can have a second Shore value and/or durometer level, wherein the second value or level is greater than the first value or level. In an example, a first portion of the circumference of a biometric wearable device (e.g. finger ring or smart watch) can have a first level of stretchability and a second portion of the circumference of the device can have a second level of stretchability, wherein the second level is greater than the first level, and wherein the first portion is smaller than the second portion.

In an example, a first portion of the circumference of a biometric wearable device (e.g. finger ring or smart watch) can have a first elasticity level and a second portion of the circumference of the device can have a second elasticity level, wherein the second level is greater than the first level, and wherein the first portion is between 20% and 40% of the circumference of the device. In another example, a first portion of the circumference of a biometric wearable device (e.g. finger ring or smart watch) can have a first level of stretchability and a second portion of the circumference of the device can have a second level of stretchability, wherein the second level is greater than the first level, and wherein the first portion is between 60% and 80% of the circumference of the device.

In an example, a biometric wearable device (e.g. finger ring or smart watch) can further comprise a local data processor. In an example, a biometric wearable device (e.g. finger ring or smart watch) can include a data transmitter which transmits data from the light receivers to a remote data processor, wherein this data is analyzed in the remote data processor to measure a biometric parameter level. In an example, a biometric wearable device (e.g. finger ring or smart watch) can be in wireless communication with an external device selected from the group consisting of: a cell phone, an electronic tablet, electronically-functional eyewear, a home electronics portal, an internet portal, a laptop computer, a mobile phone, a remote computer, a remote control unit, a smart phone, a smart utensil, a television set, and a virtual menu system. In an example, a device or system can be in wireless communication with an external device. In another example, a system including a biometric wearable device can also include a desktop computer, an electronic tablet, or a laptop.

In an example, a biometric wearable device (e.g. finger ring or smart watch) can comprise: a wearable device such as a wearable band or finger ring worn around a body member (e.g. finger, wrist, and/or arm); a circumferential array of light emitters around the wearable device; one or more light receivers which receive light beams from a light emitter after the light beams have been transmitted through or reflected by the body member, and one or more additional components selected from the power source, power-transducing component, and display screen. In an example, a biometric wearable device (e.g. finger ring or smart watch) can include an energy source which powers a light emitter, a light receiver, a data processor, a data transmitter, and/or a charge coupled device. In an example, an energy source can transduce, harvest, and/or generate energy from ambient electromagnetic energy.

In another example, a biometric wearable device (e.g. finger ring or smart watch) can further comprise one or more other components selected from the group consisting of: power source (e.g. battery), flexible electroconductive wires and/or textile channels, data processor (local, remote, or both local and remote), wireless data transmitter, wireless data receiver, pressure sensors, motion sensors (e.g. accelerometer and gyroscope), inclinometer, mirrors (e.g. micromirror array), pump and/or impellor (e.g. air or liquid pump or impellor), tubes (e.g. air or liquid conducting tubes), air or liquid reservoir, and electromagnetic actuator. In an example, a biometric wearable device (e.g. finger ring or smart watch) can include a data transmitter and/or data receiver. In an example, a device or system can further comprise a display screen or touch screen. In an example, an optical (e.g. spectroscopic) sensor can further comprise one or more optical filters selected from the group consisting of: optical absorption filter; acousto-optic filter; Bragg filter; cascaded filter; dielectric thin-film filter; Fabry-Perot filter; hybrid filter; and optical interference filter.

In another example, data from a biometric wearable device (e.g. finger ring or smart watch) can be analyzed using time of flight Diffuse Optical Tomography (DOT) to measure a biometric parameter level in a body member (e.g. finger, wrist, or arm). In an example, data from a biometric wearable device (e.g. finger ring or smart watch) can be analyzed using Diffuse Optical Tomography (DOT) to measure a biometric parameter level in a body member (e.g. finger, wrist, or arm). In an example, data from a biometric wearable device (e.g. finger ring or smart watch) can be analyzed using one or more optical methods selected from the group consisting of: Diffuse Optical Imaging (DOI), Diffuse Optical Spectroscopic Imaging (DOSI), Diffuse Optical spectroscopy (DOS), Diffuse Optical Tomography (DOT), Frequency-Domain Photon Migration (FDPM), Functional Near-Infrared Spectroscopy (fNIRS), Near-Infrared Spectroscopy (NIRS), Raman spectroscopy, reflectance Diffuse Optical Tomography (RDOT), Transillumination Imaging (TI), and/or Transmittance Diffuse Optical Tomography (TDOT).

In an example, data from a biometric wearable device (e.g. finger ring or smart watch) can be analyzed using one or more methods selected from the group consisting of: Time Reversal Optical Tomography (TROT), changes in the frequency spectrum of light transmitted through the body member (e.g. finger, wrist, or arm), Diffuse Optical Imaging (DOI), Diffuse Optical Tomography (DOT), spectroscopic analysis, analysis of absorption and/or scattering of light transmitted through the body member (e.g. finger, wrist, or arm), Near-Infrared Spectroscopy (NIRS), functional Near-Infrared Spectroscopy (fNIRS), changes in the intensity or amplitude of light transmitted through the body member (e.g. finger, wrist, or arm), changes in the phase of light transmitted through the body member (e.g. finger, wrist, or arm), Diffuse Correlation spectroscopy (DCS), Carlavian Curve Analysis (CCA), machine learning, neural network analysis, broadband spectroscopy, and/or changes in the spectral distribution of light transmitted through the body member (e.g. finger, wrist, or arm).

Having concluded the introductory section, this disclosure now describes the examples shown in FIGS. 1 through 6. It is to be understood that variations discussed in the introductory section can be applied to these examples where relevant.

FIGS. 1 and 2 show two sequential cross-sectional views of a wearable device (e.g. finger ring or smart watch) wherein an angle of light which has been emitted from a light emitter is automatically changed by the device. FIG. 1 shows the device at a first time wherein a light emitter emits a beam of light at a first angle and/or along a first vector toward a first light receiver. FIG. 2 shows the device at a second time wherein the light emitter emits a beam of light at a second angle and/or along a second vector toward a second light receiver. In an example, a beam of light can be transmitted through or reflected by different regions and/or depths of body tissue by changing the angle and/or vector along which the beam of light is emitted. In an example, the angle and/or vector along which a light emitter emits beams of light can be automatically oscillated and/or iteratively-varied to scan different regions and/or depths of body tissue.

With respect to specific components, FIGS. 1 and 2 show two sequential cross-sectional views of an example of a wearable biometric device (e.g. finger ring) comprising: a wearable ring 101 which is configured to be worn on a person's finger, wrist, or arm; an array of light emitters (including light emitter 102) and light receivers (including light receivers 103 and 104) which are configured to be worn around the person's finger, wrist, or arm; wherein the array of light emitters and light receivers is configured to collectively span at least half of the circumference of the person's finger, wrist, or arm; and wherein light energy from the light emitters which has passed through the person's body tissue and/or been reflected from the person's body tissue and has been received by the light receivers is analyzed in order to measure one or more biometric parameters selected from the group consisting of the person's oxygenation level, hydration level, glucose level, pulse rate, heart rate variability, and blood pressure.

In this example, the angle and/or vector of light emitted from light emitter 102 is automatically changed over time by the device. FIG. 1 shows the ring at a first time wherein light emitter 102 emits a beam of light 105 at a first angle and/or vector. FIG. 2 shows the ring at a second time wherein light emitter 102 emits a beam of light 105 at a second angle and/or vector. Relevant variations discussed elsewhere in this disclosure or in priority-linked disclosures can also be applied to this example.

Figures 3, 4:
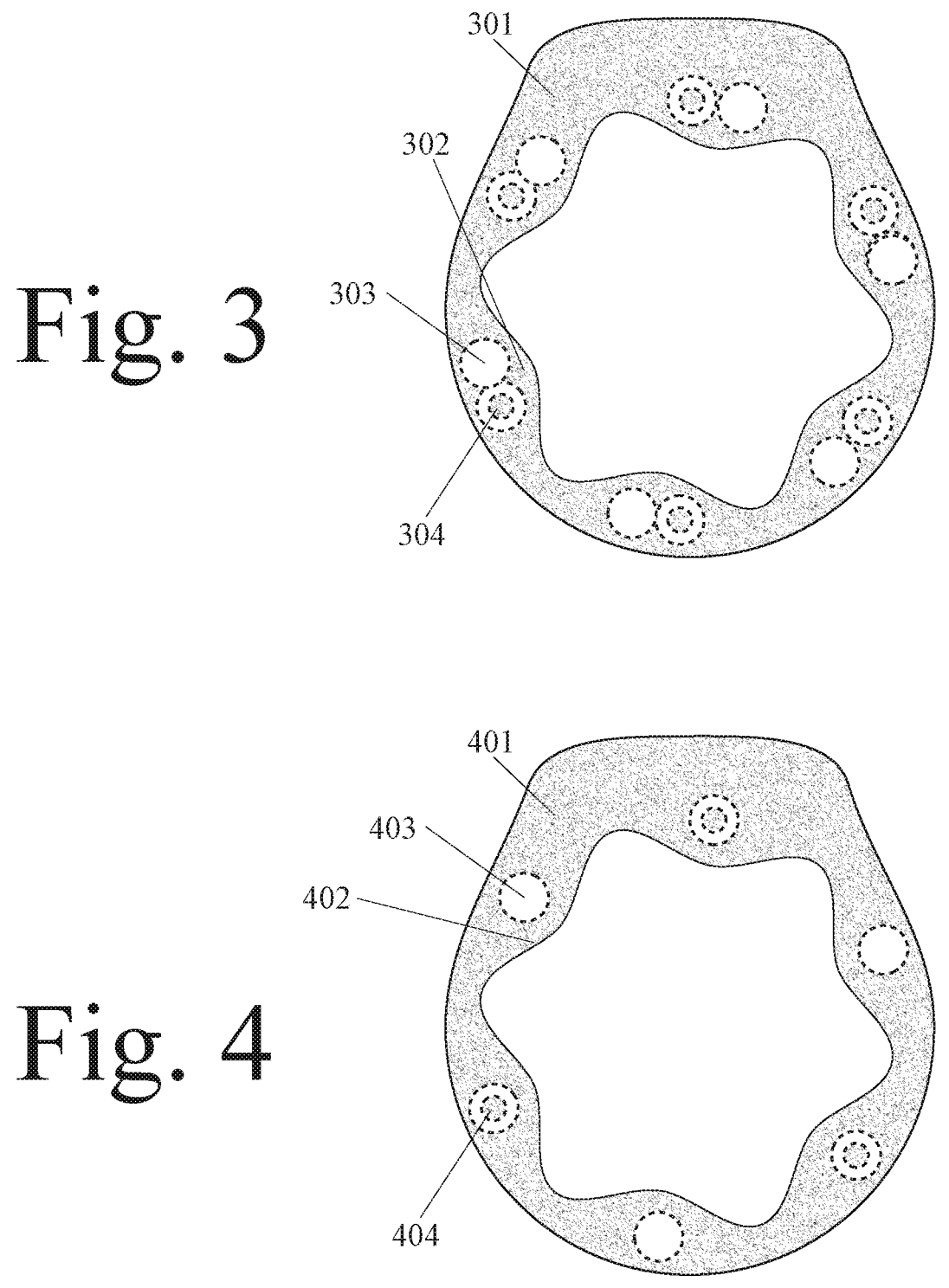

FIGS. 3 and 4 show two examples of a wearable biometric device (e.g. finger ring or smart watch) comprising: an arcuate ring which is configured to be worn around a person's body member (e.g. finger, wrist, or arm), wherein the arcuate ring spans at least two-thirds of the circumference of the person's body member and has a plurality of radial undulations; and at least three optical sensor sets which are held in proximity to the body member, wherein the optical sensor sets are located on portions of the ring which protrude toward the surface of the person's body member, wherein the optical sensor sets collectively span at least two-thirds of the circumference of the person's body member, and wherein each optical sensor set further comprises at least one red-light (e.g. infrared or visible red) emitter, at least one green-light emitter, at least one light receiver.

FIG. 3 shows a cross-sectional view of an example of a wearable biometric device (e.g. finger ring) comprising: an arcuate ring 301 which is configured to be worn around a person's finger, wherein the arcuate ring spans at least two-thirds of the circumference of the person's finger and has a plurality of radial undulations, including 302; and at least three optical sensor sets, including set 303 and 304, which are held in proximity to the person's finger, wherein the optical sensor sets are located on portions of the ring which protrude toward the surface of the person's finger, wherein the optical sensor sets collectively span at least two-thirds of the circumference of the person's finger, and wherein an optical sensor set further comprises at least one light emitter 303 and at least one light receiver 304. Relevant variations discussed elsewhere in this disclosure or in priority-linked disclosures can also be applied to this example.

FIG. 4 shows a cross-sectional view of an example of a wearable biometric device (e.g. finger ring) comprising: an arcuate ring 401 which is configured to be worn around a person's finger, wherein the arcuate ring spans at least two-thirds of the circumference of the person's finger and has a plurality of radial undulations, including 402; and at least three optical sensor sets, including sets 403 and 404, which are held in proximity to the person's finger, wherein the optical sensor sets are located on portions of the ring which protrude toward the surface of the person's finger, wherein the optical sensor sets collectively span at least two-thirds of the circumference of the person's finger, and wherein each optical sensor set further comprises at least one light emitter 403 or at least one light receiver 404. Relevant variations discussed elsewhere in this disclosure or in priority-linked disclosures can also be applied to this example.

Figures 5, 6:
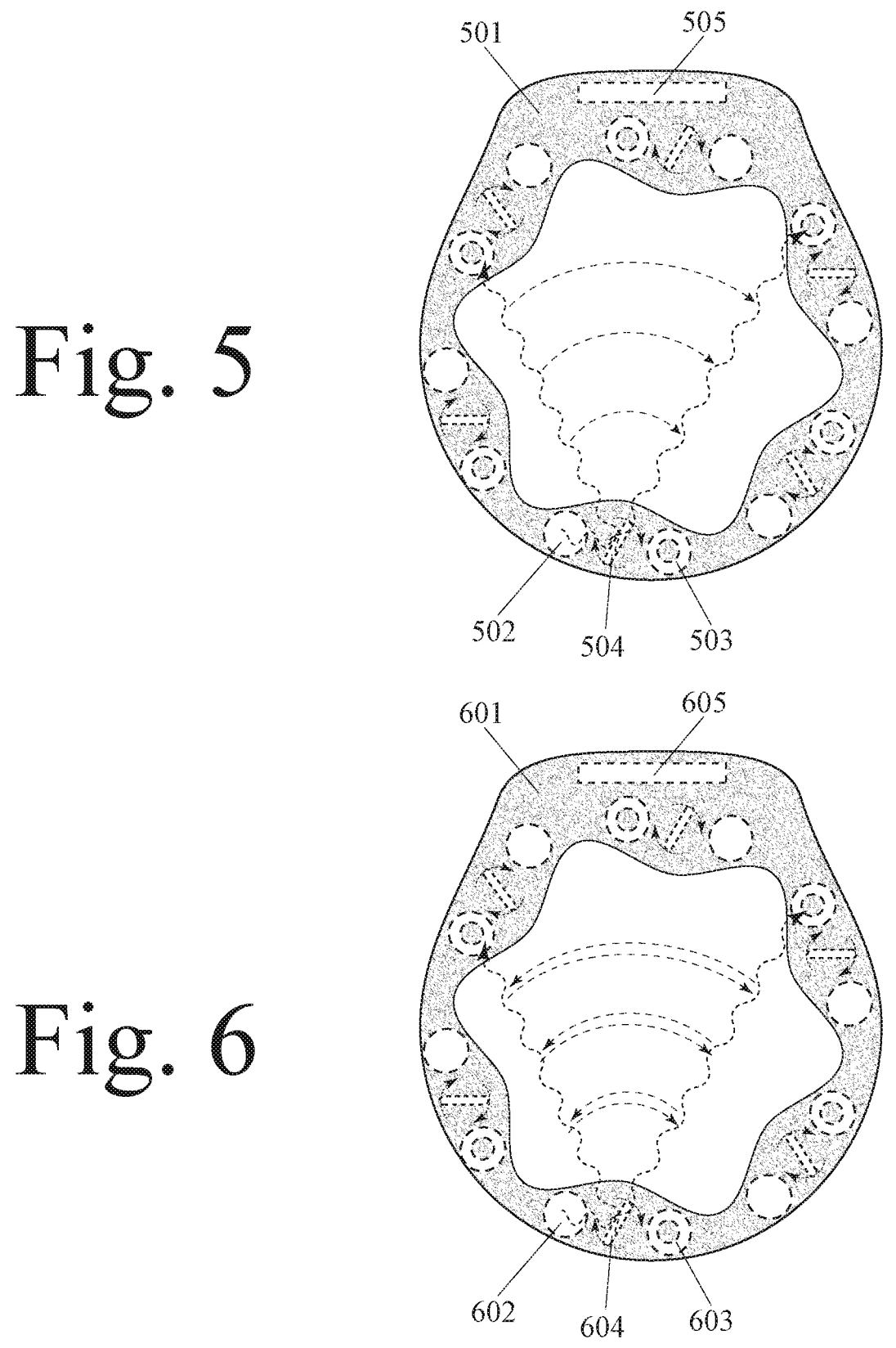

FIG. 5 shows a cross-sectional view of an example of a wearable biometric device (e.g. finger ring) comprising: an arcuate ring 501 which is configured to be worn around a person's finger, wherein the arcuate ring spans at least two-thirds of the circumference of the person's finger; at least three optical sensor sets on the ring, wherein an optical sensor set further comprises a light emitter 502 and a light receiver 503; wherein an angle or vector of light emitted from the light emitter is automatically changed over time in an intermittent manner by the device by moving a mirror or lens 504; and a data processor 505 which controls movement of the mirror or lens. Relevant variations discussed elsewhere in this disclosure or in priority-linked disclosures can also be applied to this example.

FIG. 6 shows a cross-sectional view of an example of a wearable biometric device (e.g. finger ring) comprising: an arcuate ring 601 which is configured to be worn around a person's finger, wherein the arcuate ring spans at least two-thirds of the circumference of the person's finger; at least three optical sensor sets on the ring, wherein an optical sensor set further comprises a light emitter 602 and a light receiver 603; and wherein angles or vectors along which the light emitter emits beams of light are automatically oscillated to scan different regions or depths of body tissue by moving a mirror or lens 604; and a data processor 605 which controls movement of the mirror or lens. Relevant variations discussed elsewhere in this disclosure or in priority-linked disclosures can also be applied to this example.

I claim:

1. A wearable biometric device comprising:

an arcuate ring configured to be worn around a person's finger, wherein the arcuate ring spans at least two-thirds of the circumference of the person's finger; a movable mirror or lens; and at least three optical sensor sets integrated with the arcuate ring and which are held in proximity to the person's finger, wherein an optical set comprises a light emitter and a light receiver, wherein an angle or vector of light emitted from the light emitter is automatically changed over time in an intermittent manner by the device by moving the mirror or lens; and a data processor which controls movement of the mirror or lens.

2. A wearable biometric device comprising:

an arcuate ring configured to be worn around a person's finger, wherein the arcuate ring spans at least two-thirds of the circumference of the person's finger; a movable mirror or lens; and at least three optical sensor sets integrated with the arcuate ring and which are held in proximity to the person's finger, wherein an optical set comprises a light emitter and a light receiver, and wherein angles or vectors along which the light emitter emits beams of light are automatically oscillated to scan different regions or depths of body tissue by moving the mirror or lens; and a data processor which controls movement of the mirror or lens.

* * * * *